United States Patent
Amit et al.

(10) Patent No.: US 11,485,971 B2
(45) Date of Patent: Nov. 1, 2022

(54) CRISP-SEQ, AN INTEGRATED METHOD FOR MASSIVELY PARALLEL SINGLE CELL RNA-SEQ AND CRISPR POOLED SCREENS

(71) Applicant: Yeda Research and Development Co. Ltd., Rehovot (IL)

(72) Inventors: Ido Amit, Rehovot (IL); Diego Jaitin, Rehovot (IL); David Lara-Astiaso, Rehovot (IL); Assaf Weiner, Rehovot (IL); Ido Yofe, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 161 days.

(21) Appl. No.: 16/330,774

(22) PCT Filed: Sep. 14, 2017

(86) PCT No.: PCT/IL2017/051043
§ 371 (c)(1),
(2) Date: Mar. 6, 2019

(87) PCT Pub. No.: WO2018/051347
PCT Pub. Date: Mar. 22, 2018

(65) Prior Publication Data
US 2019/0194653 A1 Jun. 27, 2019

Related U.S. Application Data

(60) Provisional application No. 62/394,324, filed on Sep. 14, 2016, provisional application No. 62/421,503, filed on Nov. 14, 2016, provisional application No. 62/427,325, filed on Nov. 29, 2016.

(51) Int. Cl.
| | | |
|---|---|---|
| *C12N 15/79* | (2006.01) | |
| *C07H 21/04* | (2006.01) | |
| *C12N 15/11* | (2006.01) | |
| *C12N 15/63* | (2006.01) | |
| *C12N 15/10* | (2006.01) | |
| *C12N 9/22* | (2006.01) | |
| *C12Q 1/6883* | (2018.01) | |
| *C12N 15/85* | (2006.01) | |
| *C07H 21/02* | (2006.01) | |

(52) U.S. Cl.
CPC ............... *C12N 15/11* (2013.01); *C12N 9/22* (2013.01); *C12N 15/102* (2013.01); *C12N 15/1093* (2013.01); *C12N 15/63* (2013.01); *C12Q 1/6883* (2013.01); *C07H 21/02* (2013.01); *C07H 21/04* (2013.01); *C12N 15/85* (2013.01); *C12N 2310/20* (2017.05); *C12N 2800/80* (2013.01)

(58) Field of Classification Search
CPC ........ C12N 15/79; C12N 15/85; C12N 15/86; C12N 2310/20; C07H 21/02; C07H 21/04
See application file for complete search history.

(56) References Cited

FOREIGN PATENT DOCUMENTS

| CA | 2932478 | 6/2015 |
|---|---|---|
| WO | WO 2018/051347 | 3/2018 |

OTHER PUBLICATIONS

Kim et al., 2019, US 20190136211 A1, effective filing date, Apr. 28, 2016.*
Glande et al., 2007, US 20070037251 A1.*
Blainey et al., 2018, US 20180080019 A1, effective filing date, Mar. 16, 2015.*
Communication Pursuant to Article 94(3) EPC dated May 4, 2020 From the European Patent Office Re. Application No. 17777660.6. (5 Pages).
International Preliminary Report on Patentability dated Mar. 28, 2019 From the International Bureau of WIPO Re. Application No. PCT/IL2017/051043. (7 Pages).
International Search Report and the Written Opinion dated Dec. 19, 2017 From the International Searching Authority Re. Application No. PCT/IL2017/051043. (15 Pages).
Guha et al. "Functional Characterization of A Novel Oncogene GNAS in Pancreatic Cancer Cells", 46th Annual Digestive Disease Week, DDW, Washington, DC, USA, May 16-19, 2015, Gastroenterology, XP002775747, 148(4/Suppl.1): S945, #Tu1957, Apr. 2015.
Jaitin et al. "Dissecting Immune Circuits by Linking CRISPR-Pooled Screens With Single-Cell RNA-Seq", Cell, XP029850714, 167(7): 1883-1896, Dec. 15, 2016.
Love et al. "Silencing Mutations in NOTCH1 Activate Calcium Signaling in B Cells", 56th Annual Meeting of the American Society of Hematology, San Francisco, CA, USA, Dec. 6-9, 2014, Blood, XP002775746, 124(21): 1696, Dec. 4, 2014. Para [0004].
Wong et al. "Multiplexed Barcoded CRISPR-Cas9 Screening Enabled by CombiGEM", Proc. Natl. Acad. Sci. USA, PNAS, XP002775745, 113(9): 2544-2549, Mar. 1, 2016. Figs.1, 2.
Communication Pursuant to Article 94(3) EPC dated Mar. 1, 2021 From the European Patent Office Re. Application No. 17777660.6. (4 Pages).

* cited by examiner

Primary Examiner — Shin Lin Chen

(57) ABSTRACT

An expression construct is disclosed which comprises:
(i) a DNA sequence which encodes at least one guide RNA (gRNA) operatively linked to a transcriptional regulatory sequence so as to allow expression of the gRNA in a target cell;
(ii) a barcode sequence for identification of the at least one gRNA operatively linked to a transcriptional regulatory sequence so as to allow expression of the barcode sequence in the target cell.

10 Claims, 26 Drawing Sheets
(26 of 26 Drawing Sheet(s) Filed in Color)
Specification includes a Sequence Listing.

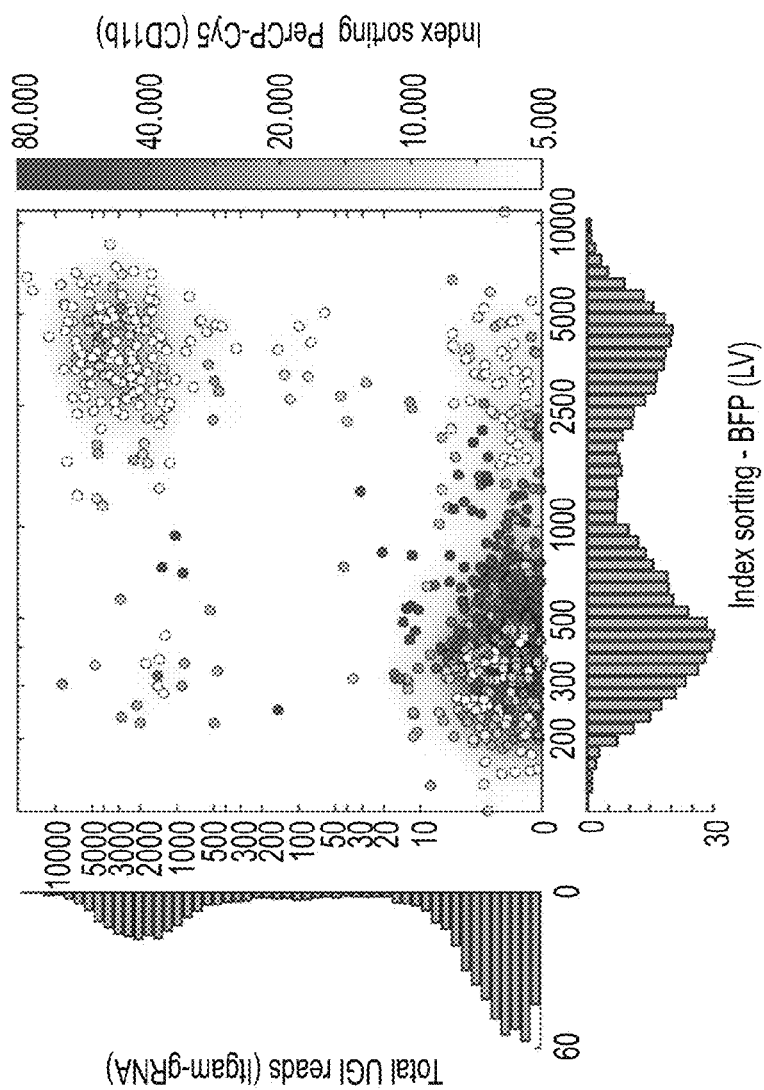
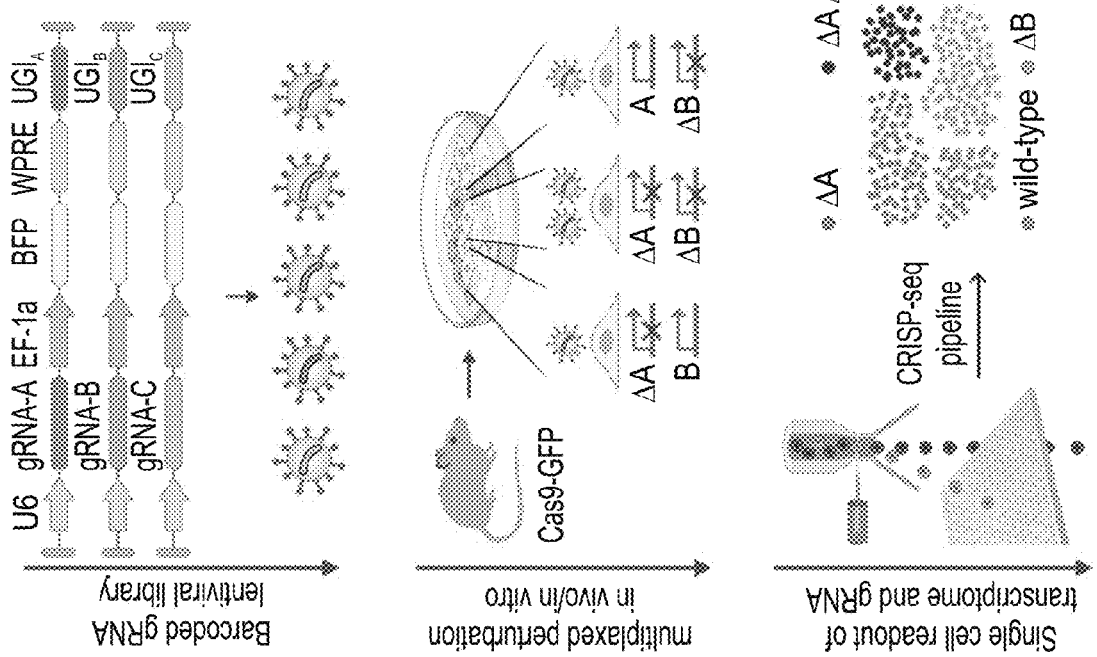
FIG. 1A
FIG. 1B

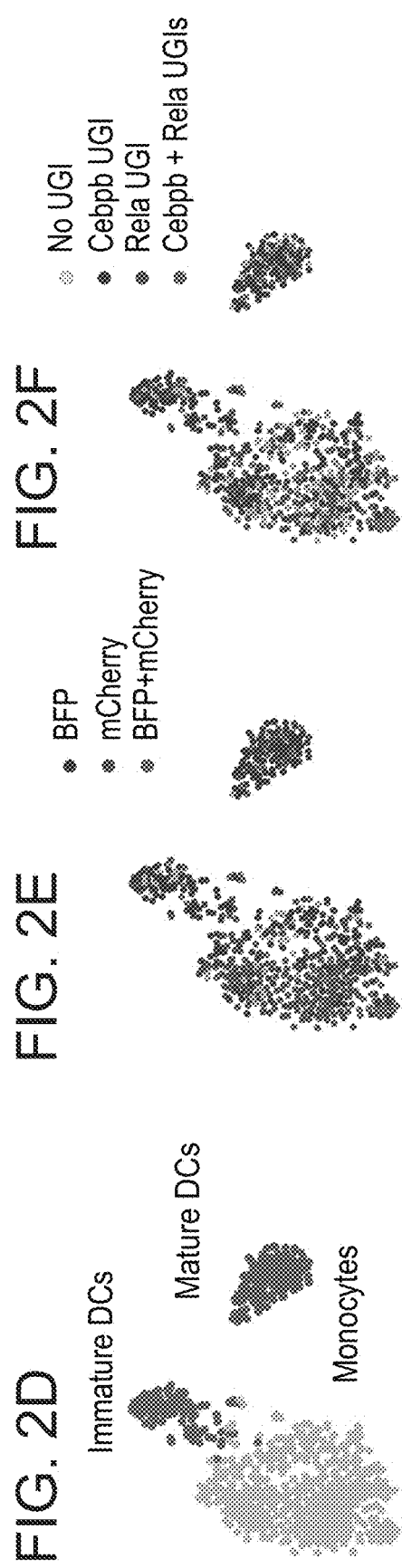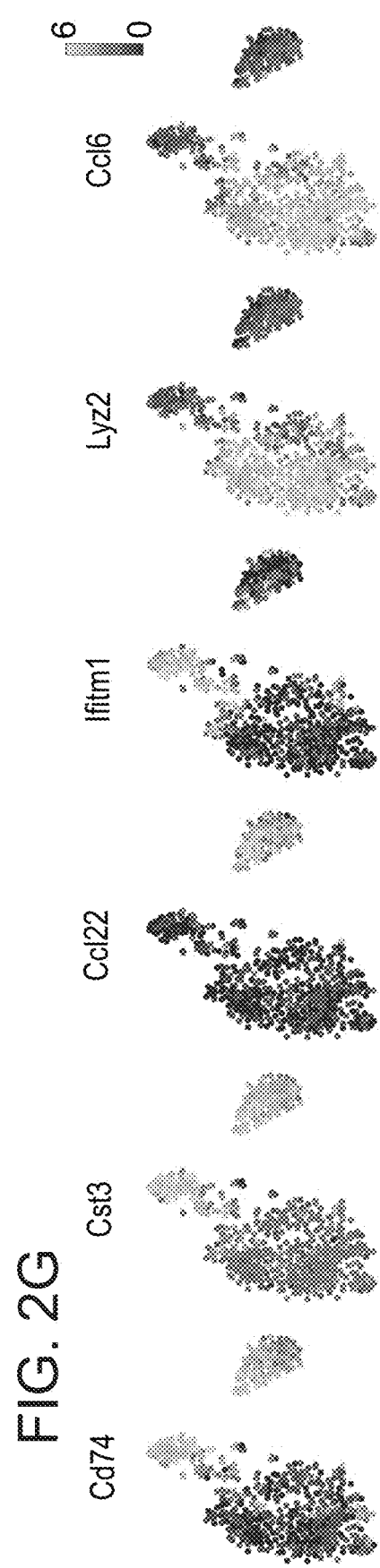

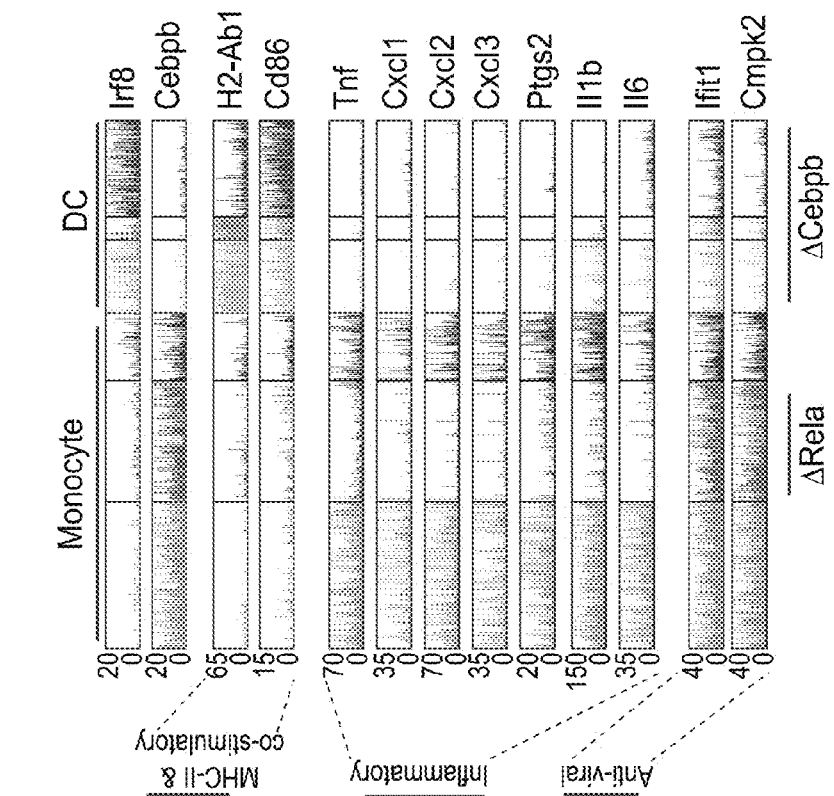
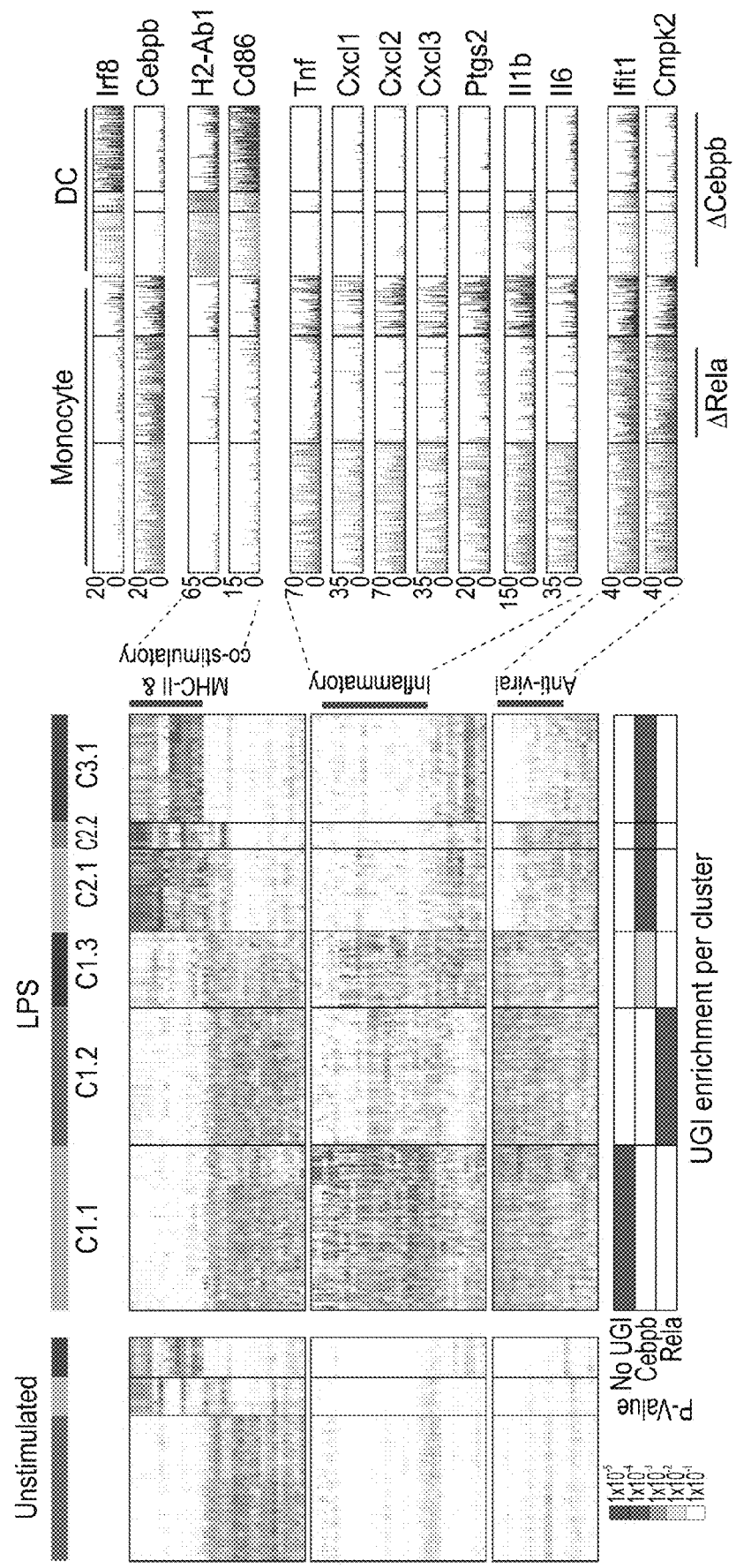
FIG. 3A
FIG. 3B

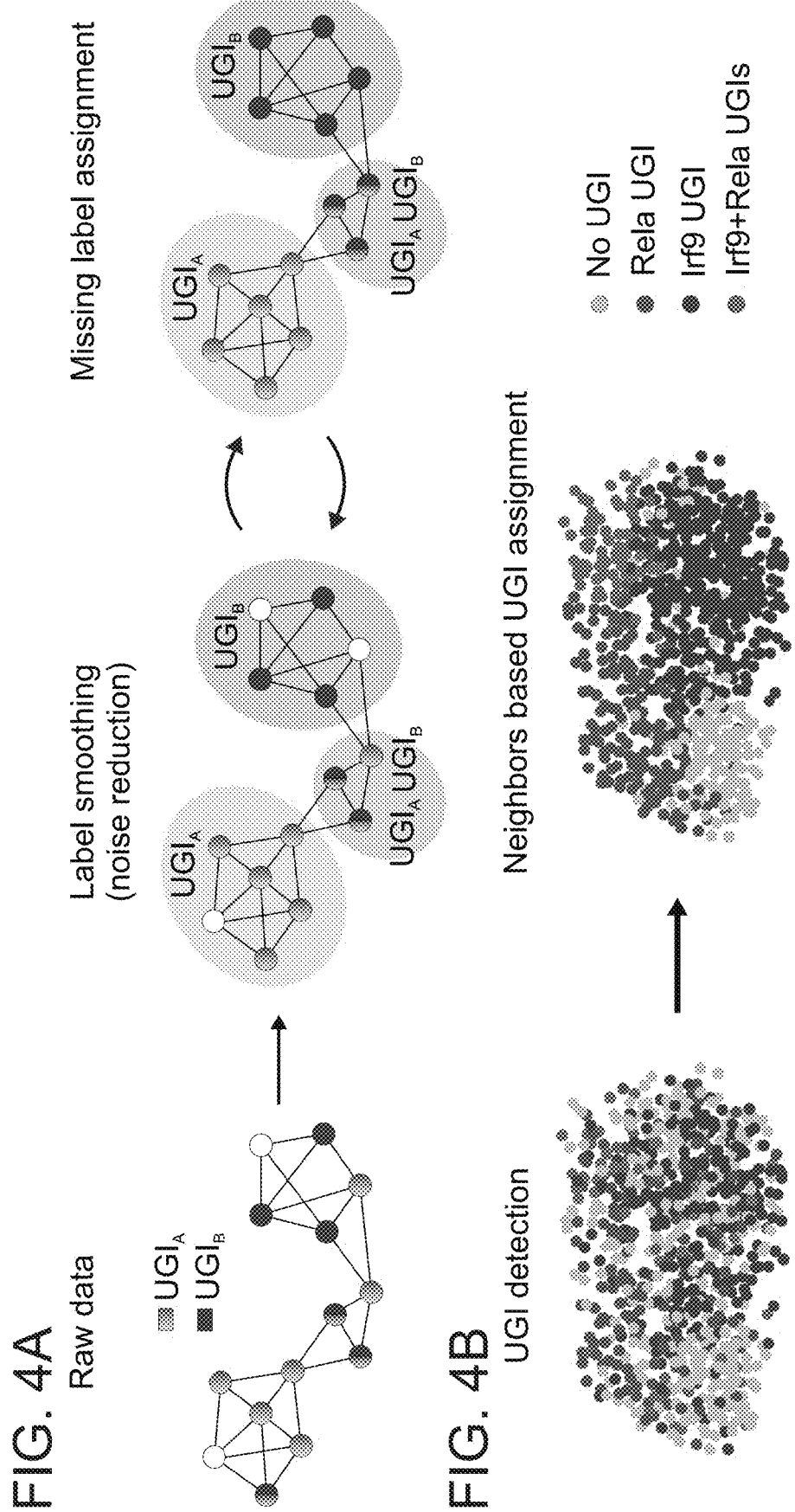

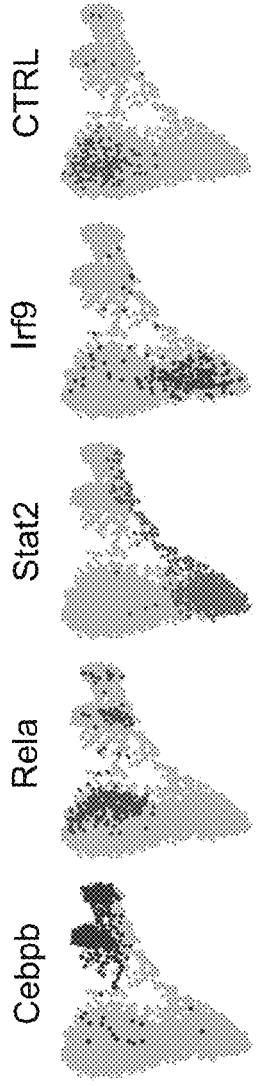
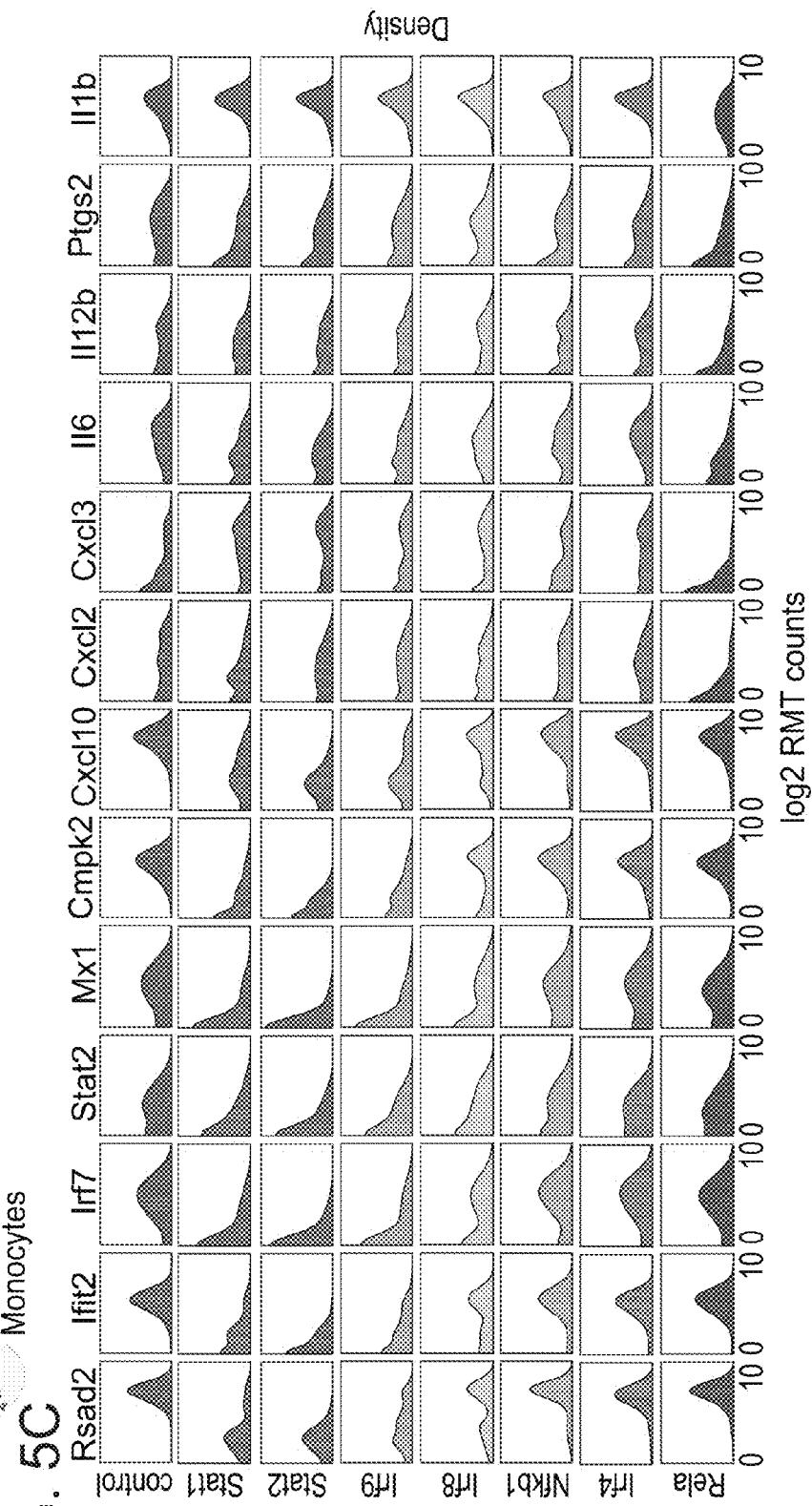

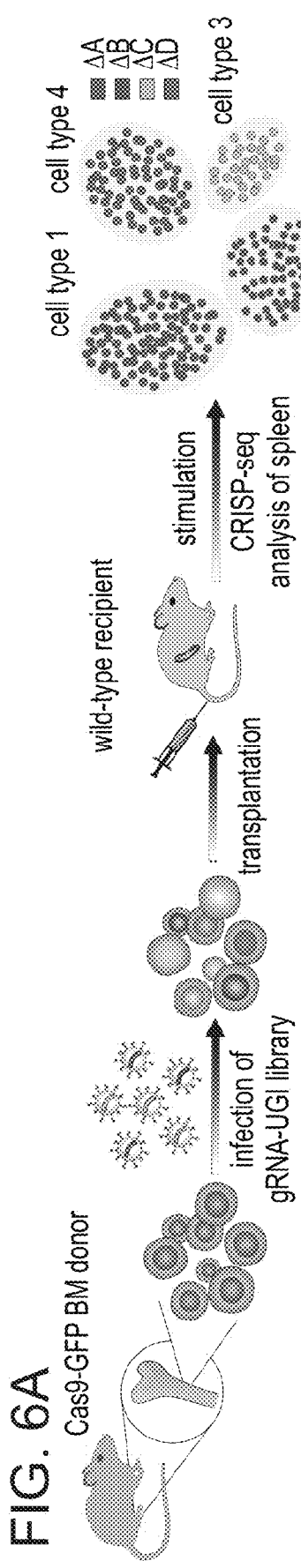
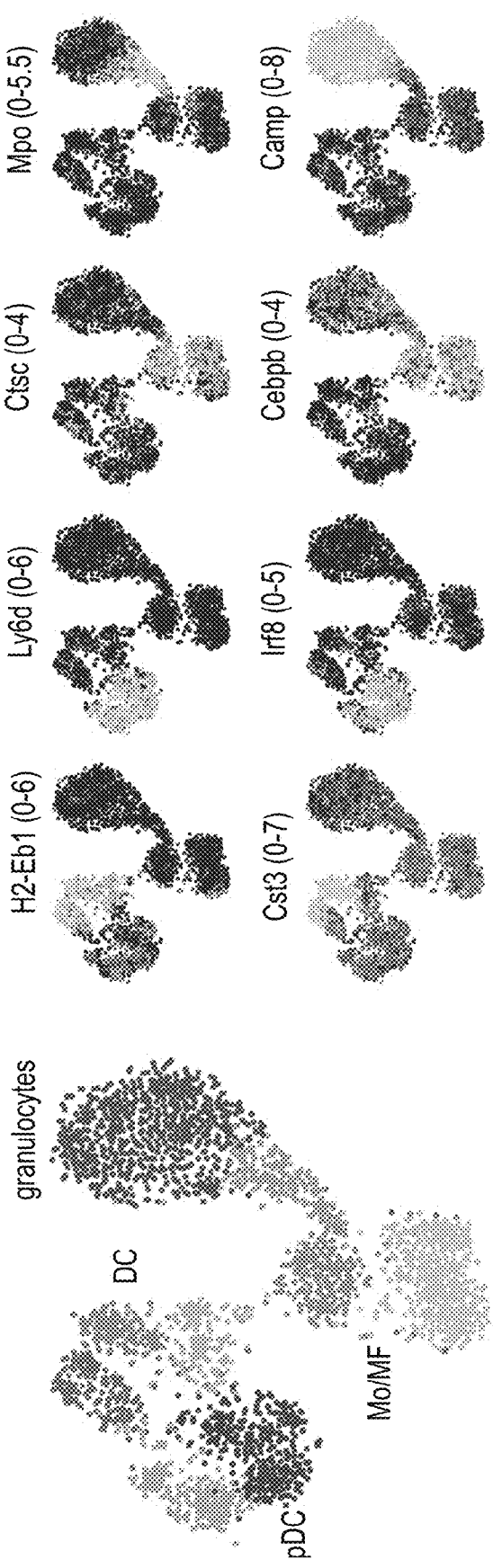
FIG. 6A
FIG. 6B
FIG. 6C

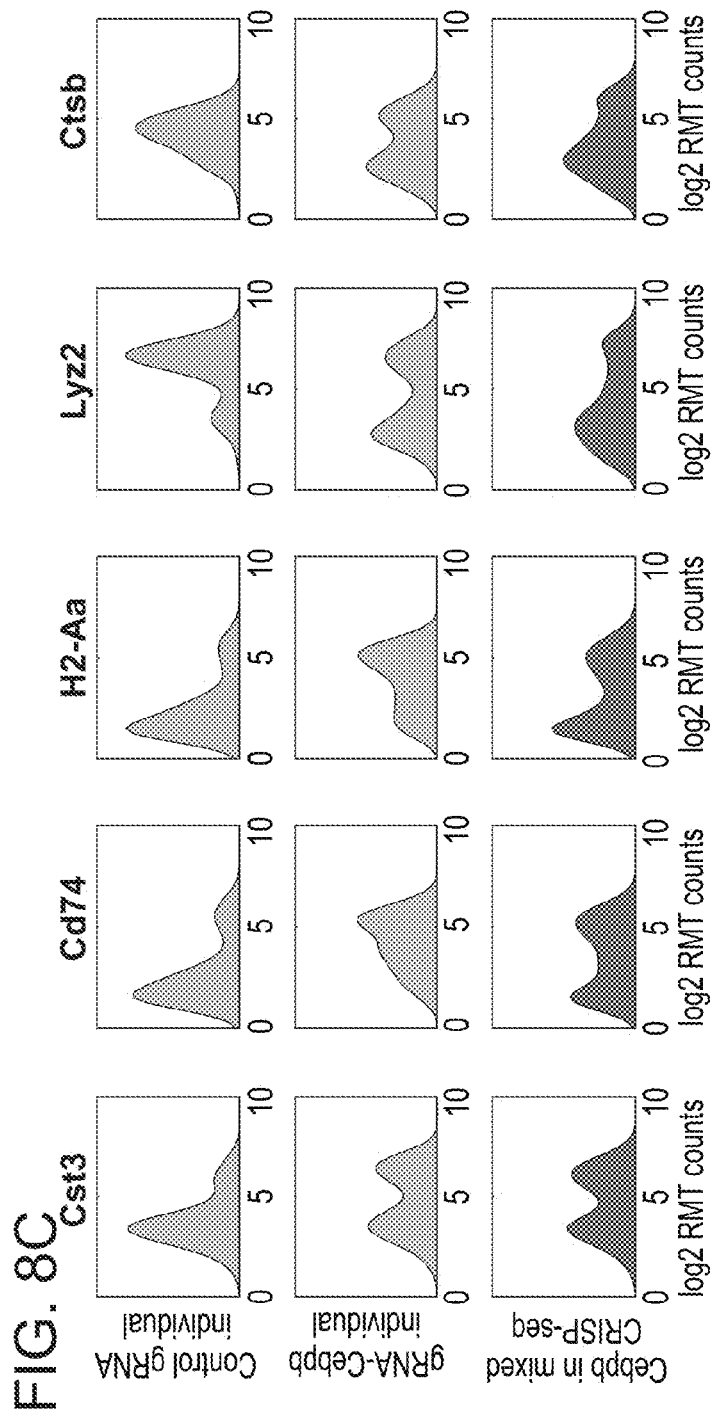
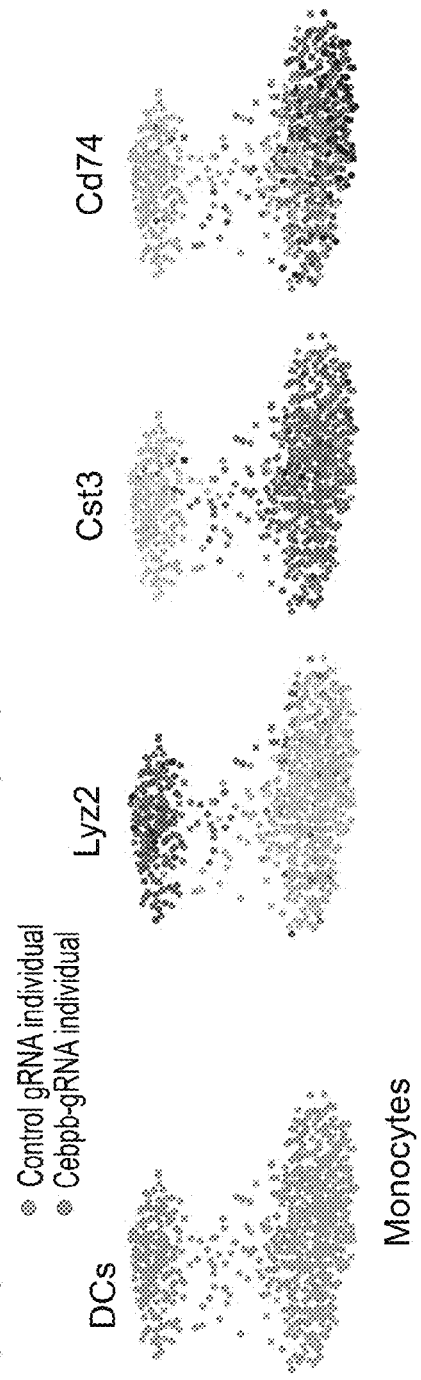
FIG. 8C
FIG. 8D
FIG. 8E

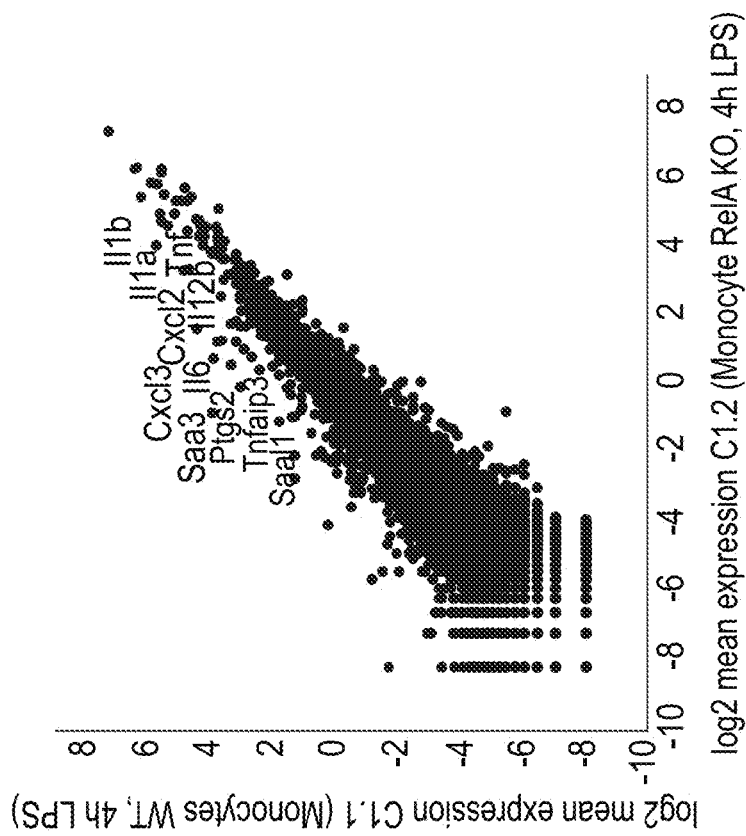
FIG. 9C
FIG. 9D
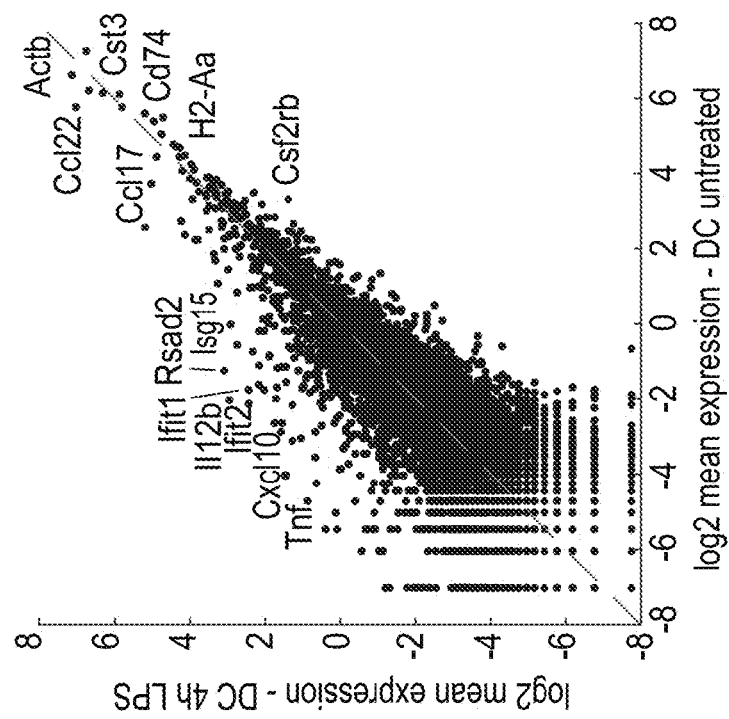
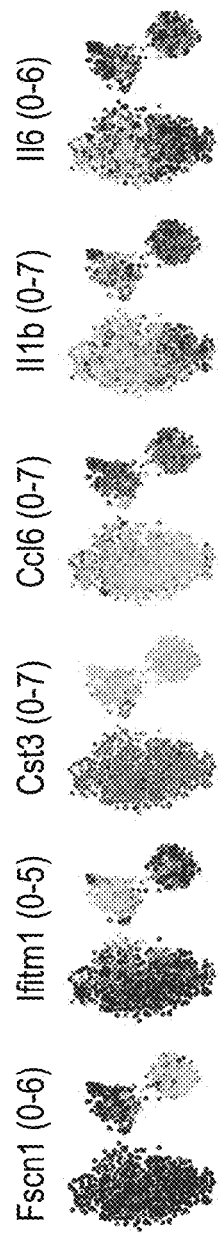
FIG. 9E

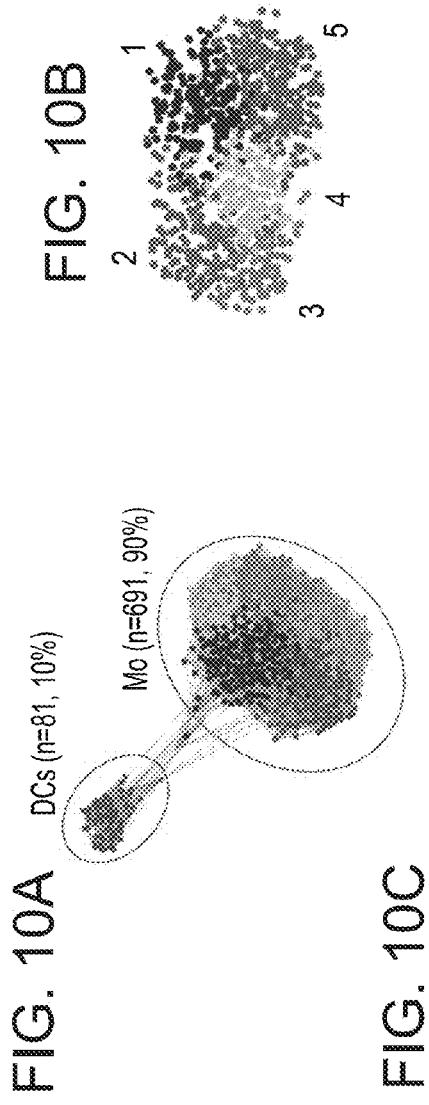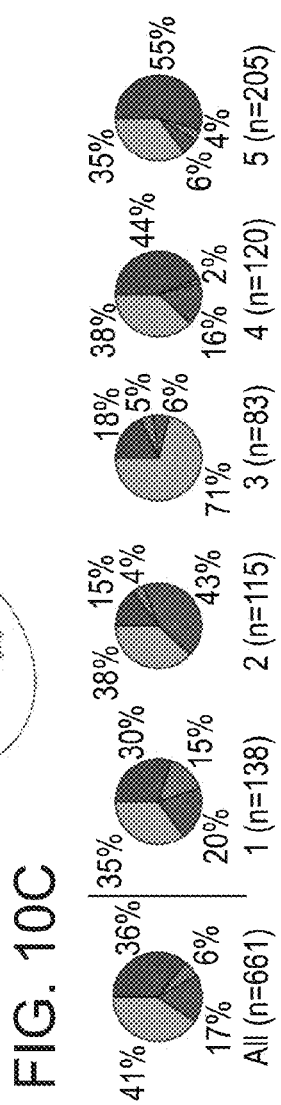
FIG. 10A  FIG. 10B  FIG. 10C  FIG. 10D

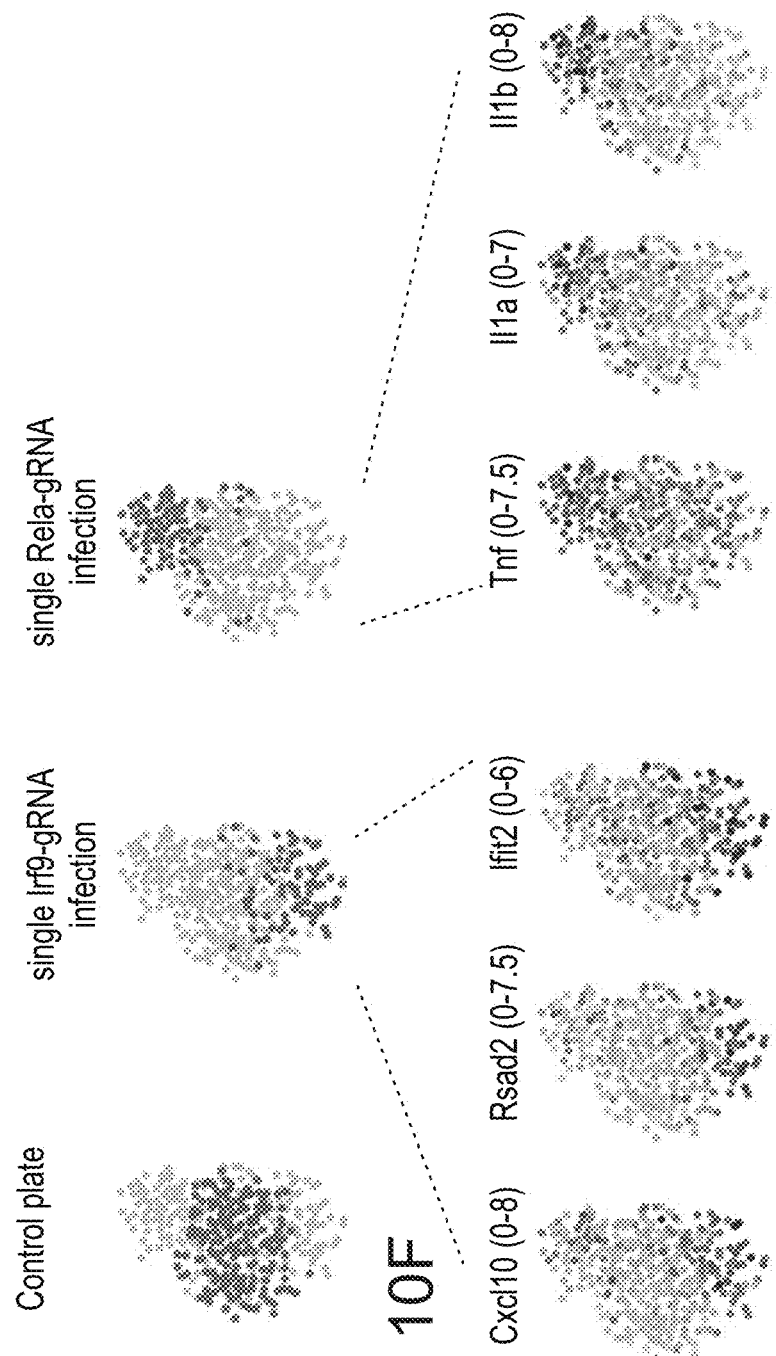

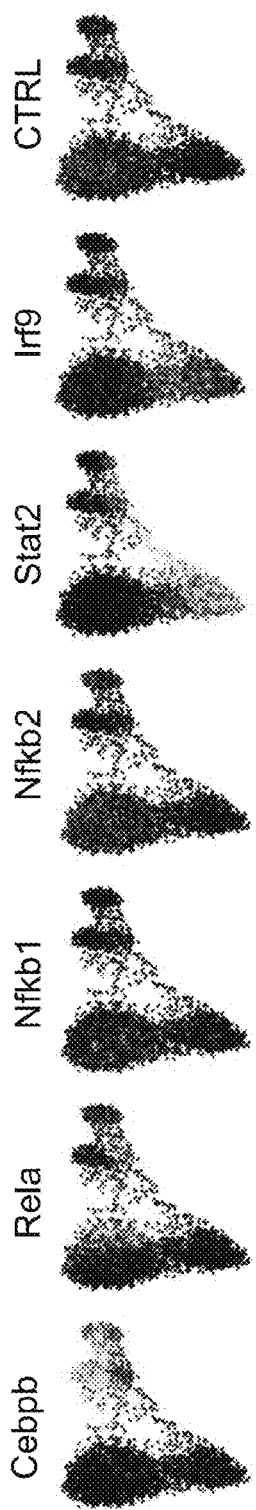
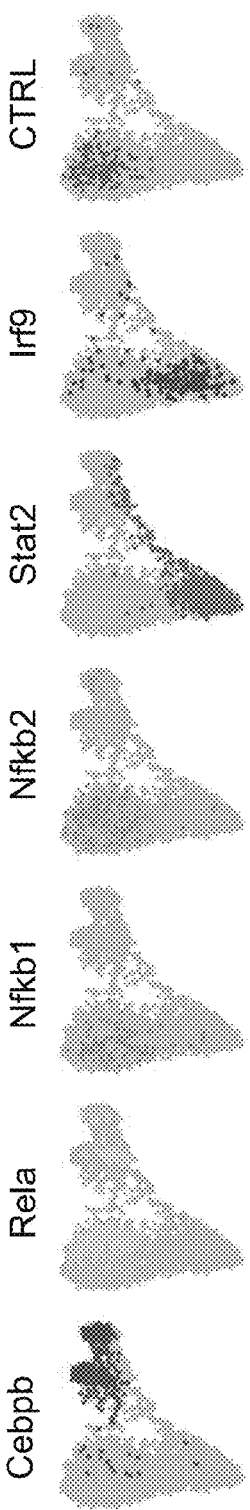
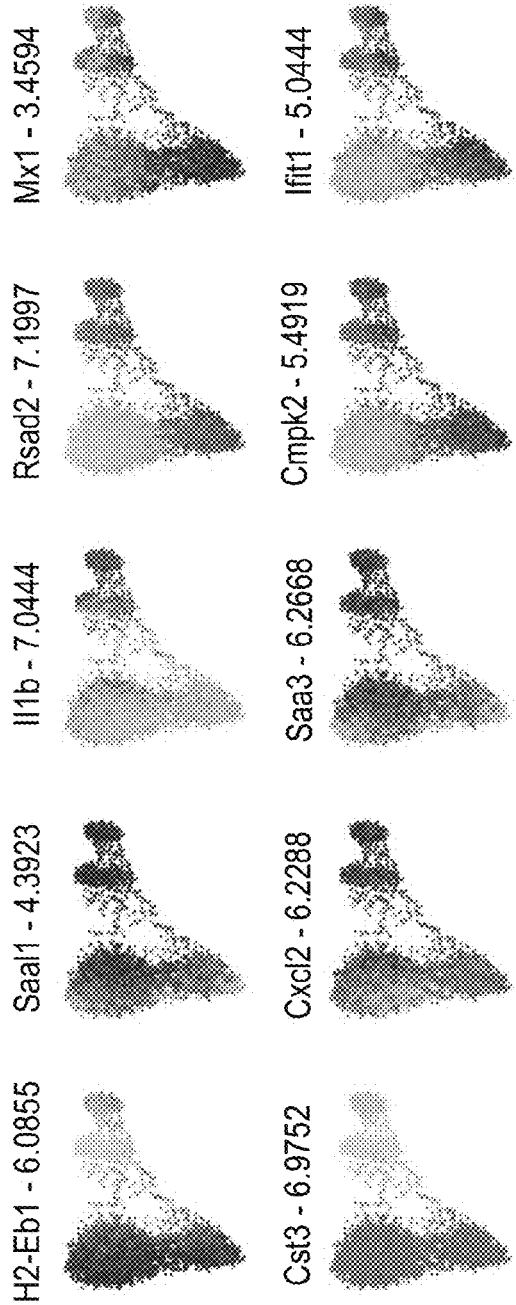
FIG. 11A
FIG. 11B
FIG. 11C

CRISP-SEQ, AN INTEGRATED METHOD FOR MASSIVELY PARALLEL SINGLE CELL RNA-SEQ AND CRISPR POOLED SCREENS

RELATED APPLICATIONS

This application is a National Phase of PCT Patent Application No. PCT/IL2017/051043 having International filing date of Sep. 14, 2017, which claims the benefit of priority under 35 USC § 119(e) of U.S. Provisional Patent Application Nos. 62/394,324 filed on Sep. 14, 2016, 62/421,503 filed on Nov. 14, 2016 and 62/427,325 filed on Nov. 29, 2016. The contents of the above applications are all incorporated by reference as if fully set forth herein in their entirety.

SEQUENCE LISTING STATEMENT

The ASCII file, entitled 76664SequenceListing.txt, created on Mar. 6, 2019, comprising 37,169 bytes, submitted concurrently with the filing of this application is incorporated herein by reference. The sequence listing submitted herewith is identical to the sequence listing forming part of the international application.

FIELD AND BACKGROUND OF THE INVENTION

The present invention, in some embodiments thereof, relates to a method of analyzing cells using CRISPR based technology.

Single cell genomic technologies enable unprecedented resolution in accurately modeling cellular diversity and play a major role in identifying and characterizing new cell types and cell states. From various cell types in the brain to gut, liver, pancreas, bone marrow as well as immune cell types in various tissues and disease states. Single cell technologies further enable to identify potential regulators of the various cell states and response, promoting testable hypothesis to elucidate molecular mechanisms of regulation. Yet current single cell technologies are descriptive by nature and lack the ability to elucidate causality, unless they are combined with knockout models.

CRISPR/Cas based technologies propelled the capacity to elucidate gene function. Current CRISPR/Cas methods are either focused on individual gene knockouts or pooled screens. Individual gene knockouts, while effective, lack in scalability and are less controlled since every perturbation is performed in a different well and may suffer from environmental and batch effects. Pooled genetic screens are powerful tools for the discovery and functional annotation of genetic elements, but lack in resolution to elucidate complex phenotypes and are usually focused on identifying crude cellular phenotypes using a small number of markers or cell states. This may result in false negative and false positive results as perturbations may create heterogeneous cell types and states that are difficult to decompose without more accurate measurements. Both methods do not allow for systematic elucidation of multiplexed genome editing, an important feature given that many cellular circuits are composed of complex and none linear pathways. Together, these highlight the need for a method to elucidate mammalian gene circuits in single cell resolution that combines the resolution of single cell RNA-seq with the power of pooled CRISPR approaches.

Background art includes US Application No. 20150307874 and Wong et al [Proc Natl Acad Sci USA. 2016 Mar. 1; 113(9): 2544-2549].

SUMMARY OF THE INVENTION

According to an aspect of the present invention there is provided an expression construct comprising:

(i) a DNA sequence which encodes at least one guide RNA (gRNA) operatively linked to a transcriptional regulatory sequence so as to allow expression of the gRNA in a target cell;

(ii) a barcode sequence for identification of the at least one gRNA operatively linked to a transcriptional regulatory sequence so as to allow expression of the barcode sequence in the target cell.

According to an aspect of the present invention there is provided a library of the expression constructs described herein, wherein the members of the library encodes non-identical gRNA sequences.

According to an aspect of the present invention there is provided a kit comprising the expression construct described herein or the library described herein and an expression construct which comprises DNA encoding a CRISPR endonuclease.

According to an aspect of the present invention there is provided a kit comprising (i) the expression construct described herein or the library described herein;

(ii) a first oligonucleotide comprising a first DNA sequence at its terminal 3' end, a RNA polymerase promoter sequence at its terminal 5' end and a barcode sequence positioned between the polydT sequence and the RNA polymerase promoter sequence.

According to an aspect of the present invention there is provided a method of modifying DNA of a cell comprising introducing the expression construct described herein into the cell population under conditions that allow Cas9 to be targeted to DNA of the cells at sites dictated by the gRNA, thereby modifying the DNA of the cell.

According to an aspect of the present invention there is provided a method of analyzing a cell population comprising:

(a) introducing the DNA expression construct described herein into the cell population under conditions that allow a CRISPR endonuclease enzyme to be targeted to DNA of the cells at sites dictated by the gRNA; and subsequently (b) analyzing the cells.

According to embodiments of the present invention, the expression construct further comprises a DNA sequence which encodes a detectable or selectable moiety.

According to embodiments of the present invention, the detectable moiety is a fluorescent moiety.

According to embodiments of the present invention, the fluorescent moiety is blue fluorescent protein (BFP).

According to embodiments of the present invention, the expression construct comprises the same number of barcodes as there are encoded gRNAs.

According to embodiments of the present invention, the barcode sequence is positioned 3' to the DNA encoding the gRNA.

According to embodiments of the present invention, the transcriptional regulatory sequence comprises a promoter sequence.

According to embodiments of the present invention, the promoter sequence of (i) is distinct to the promoter sequence of (ii).

According to embodiments of the present invention, the transcriptional regulatory sequence further comprises a polyadenylation signal.

According to embodiments of the present invention, the expression construct is a viral expression construct.

According to embodiments of the present invention, the viral expression construct is a lentiviral expression construct.

According to embodiments of the present invention, the expression construct which comprises DNA encoding the CRISPR endonuclease further comprises DNA encoding a detectable or selectable moiety.

According to embodiments of the present invention, the kit further comprises:

(i) a first oligonucleotide comprising a first sequence at its terminal 3' end, a RNA polymerase promoter sequence at its terminal 5' end and a barcode sequence positioned between the polydT sequence and the RNA polymerase promoter sequence;

(ii) a second oligonucleotide being a single stranded DNA having a free phosphate at its 5' end.

According to embodiments of the present invention, the first sequence is a polydT sequence or a random sequence of 6-10 bases.

According to embodiments of the present invention, the method further comprises introducing into the cell population an expression construct which comprises DNA encoding the CRISPR endonuclease.

According to embodiments of the present invention, the CRISPR endonuclease is selected from the group consisting of Cas9, dCAS9, CPF1 and Cas13a.

According to embodiments of the present invention, the cell population is derived from a CRISPR endonuclease transgenic animal.

According to embodiments of the present invention, the method further comprises determining the identity of the gRNA.

According to embodiments of the present invention, the method further comprises introducing into the cell population an expression construct which comprises DNA encoding the CRISPR endonuclease.

According to embodiments of the present invention, the analyzing is effected at the single cell level.

According to embodiments of the present invention, the analyzing comprises sequencing the RNA of the cells.

According to embodiments of the present invention, the method further comprises sorting the cells of the cell population so as to select for cells which express the CRISPR endonuclease and express the gRNA following step (a) and prior to step (b).

According to embodiments of the present invention, the expression construct further comprises a DNA sequence which encodes a CRISPR endonuclease.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 7A:
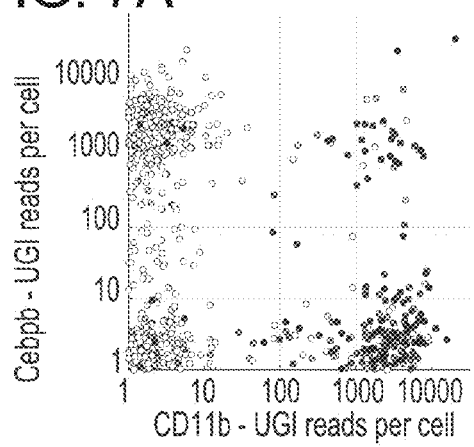
Figure 7B:
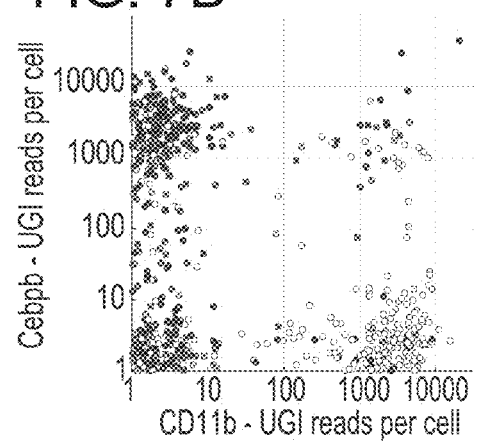
Figure 7C:
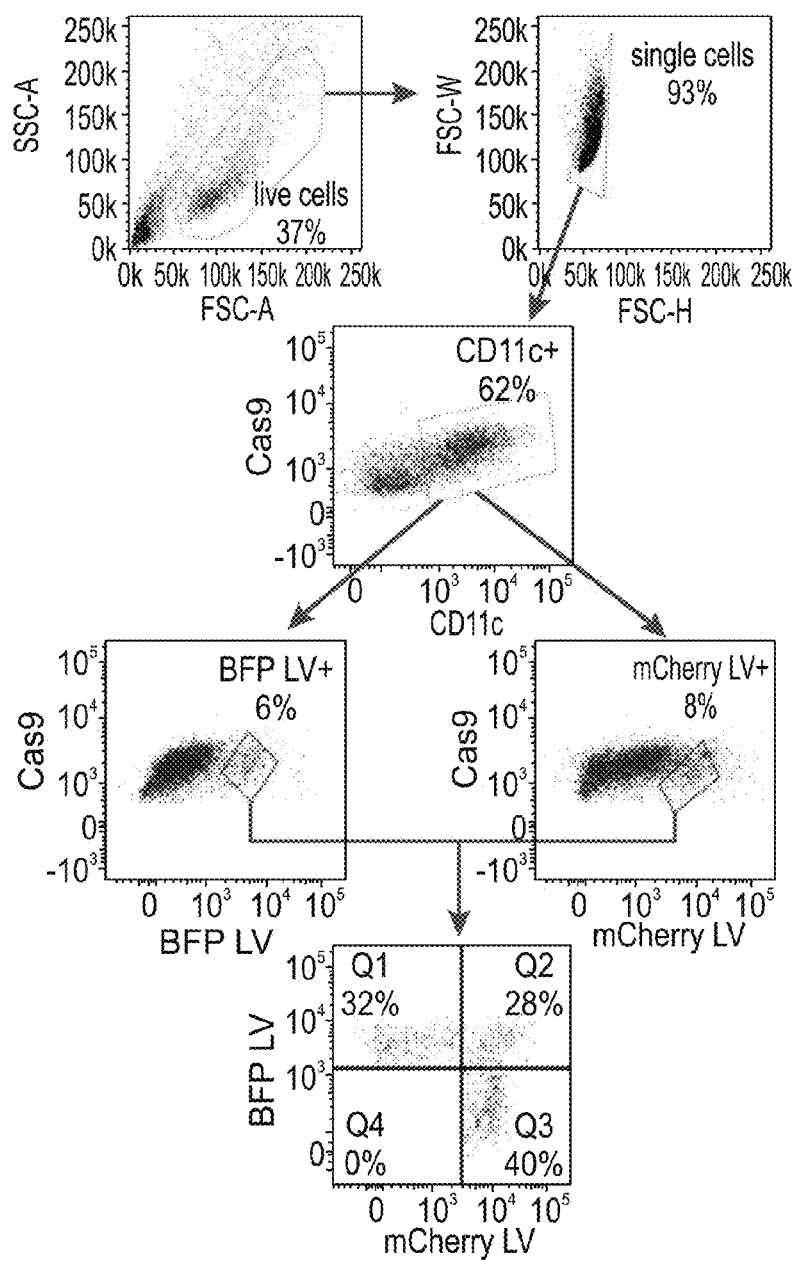

FIGS. 1A-F. CRISP-seq: An integrated method for single-cell RNA-seq and CRISPR pooled screens. (A) Schematics of the CRISP-seq procedure pipeline. Each guide RNA (gRNA) in the pooled library is detected together with cell transcriptome through the expressed Unique gRNA Index (UGI) during single-cell RNA-seq. A fluorescent marker enables selection of relevant cells and downstream analysis elucidates genotype-to-phenotype relation in single cells, as well as multiplexed perturbations. (B) Scatter plot showing Itgam/CD11b protein expression as recorded by FACS index sorting in each cell sequenced with CRISP-seq. BFP recorded intensity and total UGI reads count for Itgam are shown on the X and Y axes, respectively. (C) Violin plots of single cell Cebpb mRNA expression levels of cells labelled for mCherry (Cebpb-gRNA) at different UGI detection cut-offs in each cell. (D) Bar graph showing measured error probabilities of false positive and false negative events for cells classified with UGI-seq versus BFP or mCherry fluorescent marker classification. (E) FACS plot of myeloid cells expressing BFP (Itgam-gRNA positive (+)) and mCherry (Cebpb-gRNA+). Shown are cells sorted for insertion/deletion mutation sequencing (Indel-seq) analysis, namely BFP+, mCherry+ or double positive cells. (F) Bar plots showing percentage of genome editing around the targeted sites of each gRNA, for each quadrant indicated in (E). BFP/mCherry double negative cells (negative control) were sorted from a gate defined outside both the mCherry and the BFP positive gates (FIG. 7C).

FIGS. 2A-G. CRISP-seq analysis identifies a role for Cebpb in monocyte development. (A) Heatmap of gene expression of 731 single myeloid cells. Top panel: Expression of the 830 most differential genes across the clusters. Middle bar: UGI detection of Cebpb-gRNA (blue) and Rela-gRNA (red) in cells. Bottom panel: Expression of marker genes. (B-C) Bar plots showing the ratio between the different gRNAs and their combinations in the different clusters, using either the UGI (B) or fluorescent marker (C). (D) t-distributed stochastic neighbor embedding (t-SNE) plot of the 731 single myeloid cells depicting the separation into monocytes (orange), immature DCs (green) and DCs (purple). (E-F) Projection of the fluorescent marker (E) or UGI labeling (F) onto the t-SNE plots. (G) Projection of expression of key marker genes onto the t-SNE plot.

FIGS. 3A-E. CRISP-seq analysis of myeloid cells activated with LPS. (A) Heatmap of gene expression of 1186 single myeloid cells stimulated with LPS for 4 hours. Middle panel: Expression of the 222 most differential genes across the clusters. Left panel: Expression of same genes from 731 unstimulated myeloid cells (FIGS. 2A-G). Bottom panel: Enrichment of the different gRNAs across the clusters. (B) Expression level of selected marker genes from different biological processes across the clusters following LPS stimulation. Perturbation of key inflammatory genes is observed within the cluster enriched for RelA knockout (KO). (C) t-SNE plot of the 1186 single myeloid cells stimulated with LPS depicting the separation into the six different clusters shown in (A). (D) Projection of the UGI onto the t-SNE plots. (E) Projection of key marker genes onto the t-SNE plot.

FIGS. 4A-H. Decoupling of antiviral and inflammatory pathways by multiplexed perturbations. (A) Cartoon showing the different processes and stages of UGI labels refinement applied in our algorithm to most optimally model single cells targeted by Cas9. (B) Projection of the UGI onto the kNN graph of 691 monocytes stimulated with LPS for 4 hours, before (left) and after (right) UGI assignment correction. (C) Projection of key inflammatory and antiviral response genes onto the kNN graph. (D) Density histograms depicting the expression of key inflammatory and antiviral response genes in the different knockout combinations. (E, F) Scatter plot showing the differentially expressed genes in control, RelA KO (E) and Irf9 KO (F) cells. (G) Scatter plot of gene fold-change for RelA/Irf9 double-knockout cells over unperturbed cells, compared to the linear combination of each individual knockout effect. (H) Scatter plot comparing $-\log_{10}$ p-values (Mann-Whitney U-test) for differentially expressed genes in Irf9 KO population versus the unperturbed population and RelA KO population versus the unperturbed population.

FIGS. 5A-F. Perturbations of developmental and signaling-dependent TFs reveal the rewiring of regulatory circuits in myeloid cells. (A) Phenograph clustering of 6749 myeloid cells stimulated with LPS for 4 hours. (B) Projection of the gRNA enrichments after UGI label refinement onto the kNN graph. (C) Histograms of 5674 monocyte cells depicting the expression of key inflammatory and antiviral response genes in the different knockouts. (D) Chromatin immunoprecipitation and sequencing (ChIP-seq) analysis of Stat1/2 and RelA binding pattern in monocytes of key inflammatory and antiviral genes. (E) Correlation of ChIP-seq binding (max peak height) compared to the transcriptional fold change upon perturbation of Stat1, Stat2 or Rela. (F) Histograms of 1075 dendritic cells depicting the expression of key inflammatory and antiviral response genes in the different knockouts.

FIGS. 6A-F. In vivo CRISP-seq analyses uncover the complexity of myeloid regulatory circuits in immune niches. (A) Schematics of the in vivo CRISP-seq experimental pipeline. A pool of gRNA lentiviruses targeting genes of interest is infected into hematopoietic stem cells from Cas9-GFP+ donor mice, which are in turn transplanted into recipient mice. Following LPS stimulation, immune cells are extracted from specific immune niches, and are sorted using fluorescent markers for selection of relevant cells (Cas9 and lentivirus infection positive). CRISP-seq analysis elucidates the genotype-to-phenotype relations within the specific niche. (B) kNN graph of 2768 myeloid cells sorted from mice spleen following stimulation with LPS for 4 hours. Colours depict different cell types and states. Two pDC states (Purple), Three cDC states (Blue), Two monocyte states (Green) and two neutrophil states (Red/Orange). (C) Projection of cell type marker genes onto the kNN graph. (D) Projection of the gRNA enrichments after UGI label refinement onto the kNN graph. Stat1/2 KO cells are overlapping a pDC state (light purple), a cDC state (dark blue), and a monocyte state (light green). (E) Scatter plots showing the differentially expressed genes in control as compared to Stat1/2 KO in monocytes (left) pDC (middle) and cDC (right). (F) Projection of key antiviral response genes onto the kNN graph. Stat1/2 KO cells show a perturbed antiviral response in the different cell types.

FIGS. 7A-E. A unique guide index (UGI) strategy is effective in detecting gRNA in single cells. (A) Scatter plot showing BFP fluorescent reporter expression levels as recorded by FACS index sorting in each cell sequenced with CRISP-seq. UGI sequencing read count for Itgam (CD11b) and for Cebpb are shown on the X and Y axes, respectively. (B) Same as in (A), showing mCherry fluorescent reporter expression levels in the same experiment. (C) FACS plot showing the gating strategy to identify CD11c+ myeloid cells. Single cells were sorted from either lentivirus positive (LV+) gate, as the union between the BFP and mCherry gates. (D) Calculation of UGI-based detection sensitivity and specificity compared to the index sorting-based gRNA detection (mCherry signal, Cebpb-gRNA). Bar plot showing detection accuracy as a function of (well, UGI, RMT; RMT, random molecule tag—a.k.a. unique molecular identifier or UMI) triplet count threshold. Top panel consider UGI count >0 as positive cells and bottom panel consider UGI count >1 as positive. Rightmost bar shows the FACS positive/negative cells ratio. (E) A layout mapping of mutations (indels, insertions, SNPs) in the genomic loci around the Itgam-gRNA target (using the Interactive genome viewer (IGV) software).

FIGS. 8A-E. Validation of gRNA detection from single cells infected with a pool of gRNA's. (A-B) Violin plots of lentivirus marker expression in single cells labelled for BFP (Rela-gRNA) (A) or for mCherry (Cebpb-gRNA) (B) in binned UGI read counts. (C) Density histograms of representative genes in cells infected with a control gRNA (upper panels), in cells infected only with Cebpb-gRNA (individual; middle panels), and Cebpb UGI positive cells from CRISP-seq mix from FIGS. 2A-G. (D) tSNE plot of 349 cells infected separately with control gRNA (gray dots) combined with 359 cells infected with only Cebpb-gRNA. (E) Projection of expression of representative genes of each cell type onto the tSNE plot.

Figure 3C:
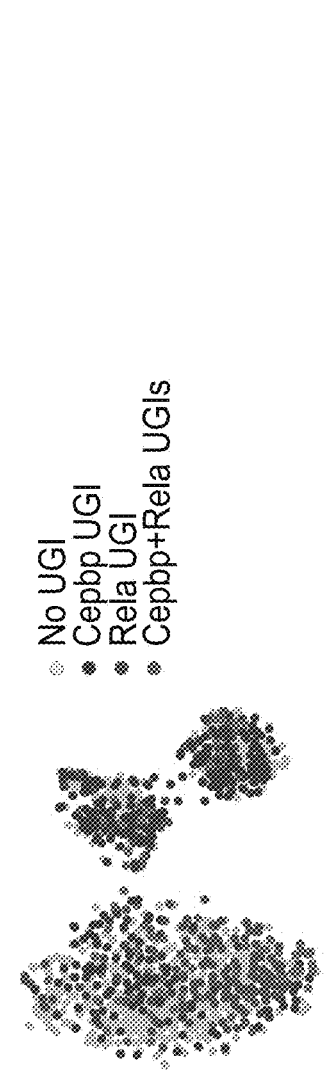
Figure 3D:
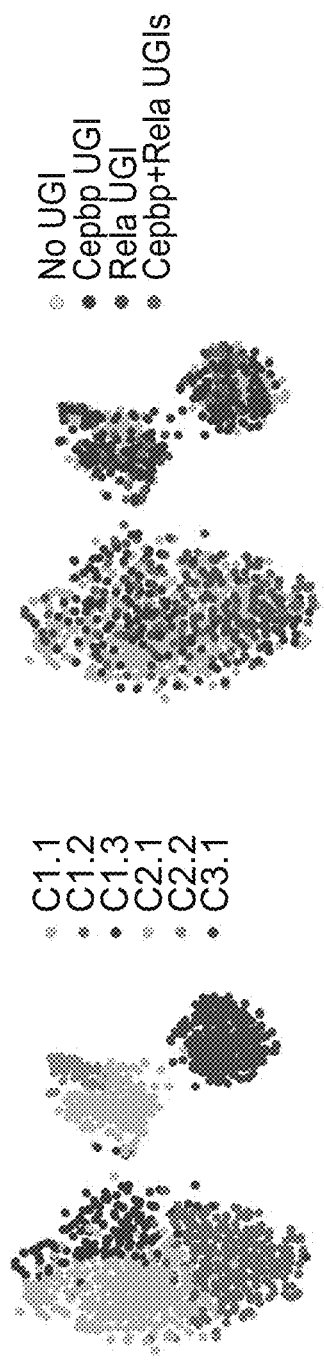
Figure 3E:
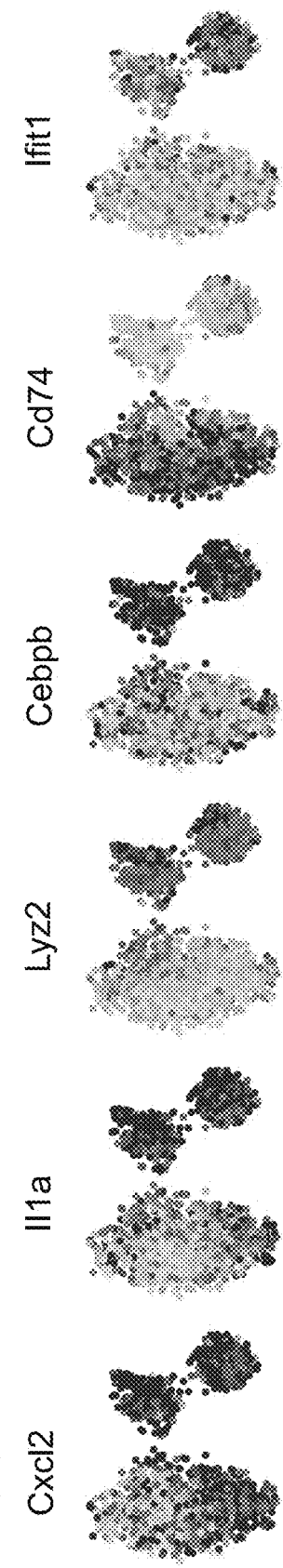

FIGS. 9A-E. The Cebpb transcription factor is essential for the monocyte state. (A-C) Scatter plots showing differentially expressed genes in 4 h LPS stimulated cells compared to untreated cells in monocytes (A), immature DCs (B), and mature DCs (C). (D) Scatter plots of mean expression in cluster 1.1 (unperturbed monocytes) vs. cluster 1.2 (RelA KO monocytes). (E) Projection of expression of additional key marker genes onto the t-SNE plot (FIG. 3E).

FIGS. 10A-F. Multiplexed perturbations of Irf9 and Rela in single cells (A) PhenoGraph clustering of 772 meyloid cells. (B) Clustering analysis of 691 monocytes cells identified five distinct clusters, defined by their different UGI composition. (C) Pie charts of the distribution of UGIs per cluster in (B). (D) Heatmap showing fold-change from unperturbed cells for RelA KO, Irf9 KO and RelA/Irf9 double KO. Bottom row correspond to levels computed as the sum of the individual KO. (E) Combined tSNE plot of cells infected with individual gRNAs (three separate cultures): left, projection of cells infected with a control gRNA (red dots, 180 cells); middle, for Irf9-gRNA only (81 cells); right, for Rela-gRNA only (80 cells). (F) Projection of representative inflammatory or antiviral gene expression levels onto the tSNE plot of individual plates.

FIGS. 11A-C. Perturbations of developmental and signalling-dependent TFs (A) Bootstrapped p-values for UGI-neighbor's. (B) Refined UGI assignment using p<0.001 as positive cells (C) Projection of representative genes on the graph layout plot.

FIGS. 12A-F. In vivo CRISP-seq analysis identifies none-overlapping targets of Stat1/2 in different myeloid cells. (A) FACS plot showing the gating strategy to identify the donor myeloid cells from the spleen. Cas9-GFP+ BFP+ (infection positive) cells were single-cell sorted after excluding recipient lymphocytes and cells with no markers (negative for both CD11b and CD11c). (B) Projection of the expression levels of additional developmental genes onto the t-SNE plot (FIG. 6C). (C) Heatmap of 2768 myeloid cells from the in vivo experiment. Clusters correspond to FIG. 6B. Bottom panel show UGI enrichment of different gRNAs within clusters. (D-F) Ex vivo validation of Irf8 and Cebpb role in myeloid development. (D) tSNE analysis of 925 myeloid cells infected with Cebpb/Rela/Control gRNAs depicting their separation into monocytes/macrophages (green), DCs (blue) and granulocytes at different developmental stages (red and orange). (E) Left, refined UGI labels of Cebpb overlapping the DC cluster; right, refined Irf8 UGI labels overlapping the granulocytes clusters. (F) Projection of the expression levels of Irf8, Cebpb and three representative genes onto the tSNE.

DETAILED DESCRIPTION OF SPECIFIC EMBODIMENTS OF THE INVENTION

The present invention, in some embodiments thereof, relates to a method of analyzing cells using Clustered regularly interspaced short palindromic repeats (CRISPR) based technology.

Gene regulatory networks function as decision-making circuits of the cell. Functional characterization of the regulatory pathways controlling cell fate and response is critical for development of the next generation of targeted and combinatorial therapies. CRISPR-based technologies have dramatically aided these efforts; however, they are either used for individual perturbations assuming homogeneity in the population, or measure such interactions in particular loci. Despite these important efforts, a robust technology that would systematically decipher the function of genetic elements at single-cell and genome-wide resolution is still lacking. Most importantly, analysis of complex, hidden phenotypes is not possible by simple phenotypic assays, and may only be resolved by genomic techniques.

The present inventors have now conceived of a new and versatile method, named CRISP-seq, which identifies in the same cell the specific perturbation and cell state. By generating a scalable lentiviral backbone that contains, in addition to the guide RNA module, a fluorescent marker and sensitive transcribed unique guide index (UGI), the present inventors show that CRISP-seq uncovers in a single experiment the function of multiple factors and their combinations (FIG. 1A). The present inventors successfully applied CRISP-seq to uncover regulators of cell state and response of myeloid cells and show that their unique design is broadly applicable for both ex vivo models and, importantly, for studying regulation of immune cells in specific niches within animal models.

The approach is not limited to coding genes, but can be used to perturb other genetic elements such as non-coding RNA as well as promoters, enhancers and any other DNA elements. CRISP-seq can also be naturally scaled in terms of the function of different circuit components under different environmental conditions. The present inventors have exemplified two conditions, namely unstimulated and LPS-stimulated cells. However, the pool of gRNA-perturbed cells can be stimulated by different conditions, or treated with various small molecules, with considerably greater flexibility and scalability than other approaches.

The technology described in the present invention may be used in researching a myriad of medical diseases including neurodegeneration, autoimmune disease, cancer, and other immune related diseases.

Thus, according to a first aspect of the present invention there is provided an expression construct comprising:

(i) a DNA sequence which encodes at least one guide RNA (gRNA) operatively linked to a transcriptional regulatory sequence so as to allow expression (i.e. RNA expression) of the gRNA in a target cell;

(ii) a barcode sequence for identification of said at least one gRNA operatively linked to a transcriptional regulatory sequence so as to allow expression of the barcode sequence in the target cell.

At its minimum, the expression construct of this aspect of the present invention is designed to express two sequences:
1. at least one guide RNA (gRNA); and
2. a barcode sequence.

Each of these will be discussed in detail herein below.

1. gRNA gRNA is one of two distinct components of the CRIPSR/Cas system for genome editing. The other component necessary for bringing about genome editing is an endonuclease e.g. Cas9.

As used herein, the term "guide RNA" (gRNA) generally refers to an RNA molecule (or a group of RNA molecules collectively) that can bind to a CRISPR endonuclease (e.g. Cas protein) and aid in targeting the endonuclease to a specific location within a target polynucleotide (e.g., a DNA).

A guide RNA can comprise a crRNA segment and a tracrRNA segment.

As used herein, the term "crRNA" or "crRNA segment" refers to an RNA molecule or portion thereof that includes a polynucleotide-targeting guide sequence, a stem sequence, and, optionally, a 5'-overhang sequence.

As used herein, the term "tracrRNA" or "tracrRNA segment" refers to an RNA molecule or portion thereof that includes a protein-binding segment (e.g., the protein-binding segment is capable of interacting with a CRISPR-associated protein, such as a Cas9). In one embodiment, the guide RNA encompasses a single guide RNA (sgRNA), where the crRNA segment and the tracrRNA segment are located in the same RNA molecule. In another embodiment, the "guide RNA" is comprised of two or more RNA molecules, where the crRNA segment and the tracrRNA segment are located in separate RNA molecules.

Preferably, the gRNA encodes a combination of the target homologous sequence (crRNA) and the endogenous bacterial RNA that links the crRNA to the CRISPR endonuclease (tracrRNA) in a single chimeric transcript i.e. sgRNA.

A single-molecule guide RNA comprises two stretches of nucleotides (a targeter-RNA and an activator-RNA) that are complementary to one another, are covalently linked (directly, or by intervening nucleotides referred to as "linkers" or "linker nucleotides"), and hybridize to form the double stranded RNA duplex (dsRNA duplex) of the protein-binding segment, thus resulting in a stem-loop structure. The targeter-RNA and the activator-RNA can be covalently linked via the 3' end of the targeter-RNA and the 5' end of the activator-RNA. Alternatively, targeter-RNA and the activator-RNA can be covalently linked via the 5' end of the targeter-RNA and the 3' end of the activator-RNA.

The gRNA/CRISPR endonuclease complex is recruited to the target sequence by the base-pairing between the gRNA sequence and the complement genomic DNA. For successful binding of the CRISPR endonuclease, the genomic target sequence must also contain the correct Protospacer Adjacent Motif (PAM) sequence immediately following the target sequence. The binding of the gRNA/CRISPR endonuclease complex localizes the CRISPR endonuclease to the genomic target sequence so that the CRISPR endonuclease can cleave one or both strands of the DNA or in the case of Cas9 mutants (dCas9), can bind DNA and allow regulatory perturbation (e.g. enhanced/reduced transcription if linked to transcription factors).

Full complementarity of the gRNA with its target sequence is not necessarily required, provided there is sufficient complementarity to cause hybridization and promote formation of a CRISPR complex. Thus, according to some embodiments, global homology to the target sequence may be of 50%, 60%, 70%, 75%, 80%, 85%, 90%, 95% or 99%.

A target sequence may comprise any polynucleotide, such as DNA or RNA polynucleotides. In one embodiment, the gRNA of this aspect of the present invention targets protein-coding DNA.

In another embodiment, the gRNA of this aspect of the present invention targets non-protein coding DNA.

In some embodiments, a target sequence is located in the nucleus or cytoplasm of a cell.

The constructs of this aspect of the present invention may comprise a single gRNA or a plurality of gRNAs. In the latter case, the gRNAs may target the same gene or different genes. The constructs may comprise one, two, three, four, five or more gRNA sequences.

There are a number of publically available tools available to help choose and/or design target sequences as well as lists of bioinformatically determined unique gRNAs for different genes in different species such as the Feng Zhang lab's Target Finder, the Michael Boutros lab's Target Finder (E-CRISP), the RGEN Tools: Cas-OFFinder, the CasFinder: Flexible algorithm for identifying specific Cas9 targets in genomes and the CRISPR Optimal Target Finder.

2. Barcode Sequence

The barcode sequence of this aspect of the present invention serves to identify the gRNA encoded in the construct.

In one embodiment, one barcode sequence identifies one gRNA sequence. Thus, if more than one gRNA sequence is encoded in the construct, the construct will comprise that number of barcode sequences as well.

In another embodiment, one barcode sequence identifies a pair or triplet of gRNA sequences encoded in that construct.

The barcode sequence may be between 3-400 nucleotides, more preferably between 3-200 and even more preferably between 3-100 nucleotides. Thus, for example, the barcode sequence may be 6 nucleotides, 7 nucleotides, 8, nucleotides, nine nucleotides or ten nucleotides.

In order to ensure that both the gRNA and the barcode sequence are expressed following infection or transfection into a cell, both the gRNA and the barcode sequence are operatively linked to cis-acting transcriptional regulatory elements. Such elements may include promoter sequences, polyA signals and enhancer elements.

The term "promoter" as used herein refers to a sequence or sequences of DNA that function when in a relatively fixed location in regard to the transcription start site. A "promoter" contains core elements required for basic interaction of RNA polymerase and transcription factors and can contain upstream elements and response elements.

According to a particular embodiment, the gRNA and the barcode sequence are positioned such that they are under the control of different promoter sequences. This is especially relevant if the barcode sequence is positioned 3' to the gRNA sequence since the present inventors have found that the tertiary structure of the gRNA terminates transcription.

Constitutive promoters suitable for use with this embodiment of the present invention include sequences which are functional (i.e., capable of directing transcription) under most environmental conditions and most types of cells such as the cytomegalovirus (CMV) and Rous sarcoma virus (RSV).

In one embodiment, the promoter for expressing the barcode sequence is the promoter from the eukaryotic transcription elongation factor 1 alpha gene.

In another embodiment, the promoter for expressing the gRNA is a U6 or H1 promoter.

The nucleic acid constructs of the present invention may also include one or more enhancers.

Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for the present invention include those derived from polyoma virus, human or murine cytomegalovirus (CMV), the long term repeat from various retroviruses such as murine leukemia virus, murine or Rous sarcoma virus and HIV. See, Enhancers and Eukaryotic Expression, Cold Spring Harbor Press, Cold Spring Harbor, N.Y. 1983, which is incorporated herein by reference.

According to a specific embodiment, the construct comprises the WPRE element from the Woodchuck hepatitis virus or the CTE element from Mason-Pfizer monkey virus.

The construct of this aspect of the present invention typically also comprises at least one polyadenylation signal sequence at a position such that the barcode sequence transcript is polyadenylated. Two distinct sequence elements are required for accurate and efficient polyadenylation: GU or U rich sequences located downstream from the polyadenylation site and a highly conserved sequence of six nucleotides, AAUAAA (SEQ ID NO: 13), located 11-30 nucleotides upstream.

The identification and use of polyadenylation signals in expression constructs is well established. It is preferred that homologous polyadenylation signals be used in the transgene constructs.

Typically, the polyA signal sequence is no more than 2000 bases downstream of the barcode sequence (typically between 300-500 bases downstream).

The present invention contemplates that the barcode sequence is positioned up- or down-stream to the gRNA sequence, although in a preferred embodiment, the barcode sequence is positioned 3' to the gRNA sequence.

Furthermore, the barcode sequence is preferably 5' to the polyA site so it can be sequenced.

As well as encoding the above described two elements, the expression constructs of this aspect of the present invention may also encode a detectable or selectable moiety. These moieties serve to provide information regarding which cells have been successfully infected/transfected and express the gRNA.

The detectable moiety can be a reporter polypeptide which is directly visualized or a member of a binding pair, which is identifiable via its interaction with an additional member of the binding pair.

According to a particular embodiment, the reporter polypeptide is a fluorescent protein. Exemplary fluorescent proteins include, but are not limited to green fluorescent protein (Genbank Accession No. AAL33912), Fluorescein isothiocyanate (Genbank Accession No. AAF22695), orange fluorescent protein (Genbank Accession No. AAL33917) and blue fluorescent protein (e.g. Uniprot No. D6NKF4).

Additional reporter polypeptides include products of bacterial luciferase genes, e.g., the luciferase genes encoded by *Vibrio harveyi, Vibrio fischeri*, and *Xenorhabdus luminescens*, the firefly luciferase gene FFlux, and the like.

In another example, the detectable moiety is an enzyme producing a colorimetric reaction.), alkaline phosphatase (Genbank Accession No. AAK73766), peroxidase (Genbank Accession No. NP_568674), histidine tag (Genbank Accession No. AAK09208), Myc tag (Genbank Accession No. AF329457), biotin ligase tag (Genbank Accession No. NP_561589), beta galactosidase (Genbank Accession No. NM_125776), and strepavidin (Genbank Accession No. S11540).

Methods of measuring the reporter polypeptide are known to those of skill in the art and the selection of the particular method is dependent upon the detectable moiety which is used in the system. For example, the reporter polypeptide may be detected using standard techniques (e.g., radioimmunoassay, radio-labeling, immunoassay, assay for enzymatic activity, absorbance, fluorescence, luminescence, and Western blot). More preferably, the level of the reporter protein is easily quantifiable using standard techniques even at low levels.

In a particular embodiment, the reporter polypeptide is measured using a fluorescence-activated cell sorter (FACS).

A Flow Cytometer typically consists of a laser light source, flow measurement chamber, and an optical system consisting of lenses, filters, and light detectors. Two photomultiplier tubes (light detectors), one at 180 degrees and one at 90 degrees to the laser, are used to measure forward (FSC) and right-angle scatter (SSC), respectively. Three fluorescence detectors, each consisting of a filter and photomultiplier tube, are used to detect fluorescence. The three detectors sense green (FL1—530 nm), orange (FL2—585 nm), and red fluorescence (FL3—650 nm). Cells may be identified by sort logic applied to all five of the detector signals (FSC, SSC, FL1, FL2, FL3) using a computer.

Exemplary Flow Cytometers that may be used in this aspect of the present invention are manufactured by companies such as Becton Dickinson (USA), Backman Coulter (USA), Partec (Germany).

As mentioned, the constructs of this aspect of the present invention may comprise a selectable moiety. Examples of suitable selectable moieties for mammalian cells are dihydrofolate reductase (DHFR), thymidine kinase, neomycin, neomycin analog G418, hydromycin, and puromycin. When such selectable moieties are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are: CHO$^{DHFR}$-cells and mouse$^{LTK}$-cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media.

The second category is dominant selection which refers to a selection scheme used in any cell type and does not require the use of a mutant cell line. These schemes typically use a drug to arrest growth of a host cell. Those cells which would express a protein conveying drug resistance and would survive the selection. Examples of such dominant selection use the drugs neomycin, (Southern P. and Berg, P., J. Molec. Appl. Genet. 1: 327 (1982)), mycophenolic acid, (Mulligan, R. C. and Berg, P. Science 209: 1422 (1980)) or hygromycin, (Sugden, B. et al., Mol. Cell. Biol. 5: 410-413 (1985)). The three examples employ bacterial genes under eukaryotic control to convey resistance to the appropriate drug G418 or neomycin (geneticin), xgpt (mycophenolic acid) or hygromycin, respectively. Others include the neomycin analog G418 and puramycin.

According to a particular embodiment, the DNA encoding the detectable/selectable moiety is operatively linked to the same promoter as for the gRNA.

According to another embodiment, the DNA encoding the detectable/selectable moiety is operatively linked to the same promoter as for the barcode sequence.

According to yet another embodiment, the DNA encoding the detectable/selectable moiety is operatively linked to a promoter that is different than that used for the gRNA and further different to that used for the barcode sequence.

An exemplary order of components on the construct from the 5' end to the 3' end is as shown in FIG. 1A. Namely: promoter 1 operatively linked to gRNA; promoter 2 operatively linked to reporter polypeptide and barcode; polyA signal.

In addition to the elements already described, the expression construct of the present invention may contain other specialized elements intended to increase the level of expression of cloned polynucleotides or to facilitate the identification of cells that carry the recombinant DNA. For example, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The expression constructs may or may not include a eukaryotic replicon. If a eukaryotic replicon is present, then the vector is amplifiable in eukaryotic cells using the appropriate selectable marker. If the construct does not comprise a eukaryotic replicon, no episomal amplification is possible. Instead, the recombinant DNA integrates into the genome of the engineered cell, where the promoter directs expression of the desired polynucleotide.

The expression constructs of the present invention can further include additional polynucleotide sequences that allow, for example, the translation of several proteins from a single mRNA such as an internal ribosome entry site (IRES) and sequences for genomic integration of the promoter-chimeric polypeptide. For example a single expression construct can be designed and co-express two distinct polypeptides one the polypeptide of interest, and one a processing enzyme as further described herein below.

Examples of mammalian expression constructs include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

Expression constructs containing regulatory elements from eukaryotic viruses such as retroviruses can also be used by the present invention. SV40 vectors include pSVT7 and pMT2. Vectors derived from bovine papilloma virus include pBV-1MTHA, and vectors derived from Epstein Bar virus include pHEBO, and p2O5. Other exemplary vectors include pMSG, pAV009/A$^+$, pMT010/A$^+$, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

Viruses are specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell.

Recombinant viral vectors are useful for in vivo expression of transgenic polynucleotides since they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

According to one embodiment, the constructs of the present invention are incorporated into lentiviruses. These viruses are advantageous because of their ability to integrate their DNA into the genome of mammalian non-dividing cells.

Sequences of exemplary constructs with BFP or mCherry are set forth in SEQ ID NOs: 15-17.

Libraries

The present inventors contemplate generating a library of the expression constructs described herein, each member encoding a unique gRNA sequence (being identified by its own bar-code sequence). It will be appreciated that the library comprises multiple copies of each member.

An individual member of a library differs from other members of that library in the DNA nucleotide sequence of the targeting segment (the guide RNA) and further comprises a different barcode associated therewith. Thus, for example, each individual member of a library can comprise the same or substantially the same nucleotide sequence of the protein-binding segment as all other members of the library; and can comprise the same or substantially the same nucleotide sequence of the transcriptional termination segment as all other members of the library; but differs from other members of the library in the nucleotide sequence of the DNA targeting segment of the guide RNA. In this way, the library can comprise members that bind to different target nucleic acids.

In another embodiment, each member of the library targets a different gene.

It is further contemplated that members of the library differ from other members of the library in the detectable moiety (e.g. color of fluorescent protein) encoded thereon. For instance the present inventors contemplate that some members of the library will encode a green fluorescent protein, while other members encode a blue fluorescent protein etc.

The library can comprise from about 3 individual members to about $10^{10}$ individual members; e.g., a library can comprise from about 10 individual members to about $10^2$ individual members, from about $10^2$ individual members to about $10^3$ individual members.

Uses

In order to use the CRISPR system, both gRNA and the CRISPR enzyme (e.g. Cas9) should be expressed in a target cell.

Methods of introducing the construct(s) into a host cell are known in the art, and any known method can be used to introduce a nucleic acid (e.g., an expression construct) into a cell. Suitable methods include e.g., viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g., Panyam et., al Adv Drug Deliv Rev. 2012 Sep. 13. pii: 50169-409X(12)00283-9. doi: 10.1016/j.addr.2012.09.023), and the like. The Cas protein can also be inserted as a purified protein.

The CRISPR endonuclease enzyme may be encoded in the same constructs which encode the gRNA (i.e. combined in a single expression construct) or may be expressed from a different expression construct. CRISPR system elements that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. A single promoter may drive expression of a transcript encoding a CRISPR enzyme and the gRNA sequence.

Examples of CRISPR endonucleases include but are not limited to Cas9, dCas9, CPF1 and Cas13a. In one embodiment, the CRISPR endonuclease is coupled to a chromatin modifying protein, such as a methylating protein or a demethylating protein. Cas9 polypeptide sequences are provided in US Patent Application No. 20160298096, the contents of which are incorporated herein by reference.

The constructs described herein are introduced into cell populations under conditions that allow the CRISPR enzyme (e.g. Cas9) to be targeted to DNA of the cells causing cleavage of the DNA at sites dictated by the gRNA.

It will be appreciated that the present inventors contemplate introducing into cell populations a plurality of the gRNA constructs of the present invention, wherein each gRNA construct is targeted towards a unique target sequence. In this way it is possible to follow the effect of downregulating multiple factors in a single cell.

In some embodiments, a genetically modified host cell has been genetically modified with an exogenous nucleic acid comprising a nucleotide sequence encoding a CRISPR enzyme (e.g., a naturally occurring Cas9; a modified, i.e., mutated or variant, Cas9; a chimeric Cas9; etc.). If such a cell is a eukaryotic single-cell organism, then the modified cell can be considered a genetically modified organism. In some embodiments, the non-human genetically modified organism is a Cas9 transgenic multicellular organism.

In some embodiments, a genetically modified non-human host cell (e.g., a cell that has been genetically modified with an exogenous nucleic acid comprising a nucleotide sequence encoding a site-directed modifying polypeptide, e.g., a naturally occurring Cas9; a modified, i.e., mutated or variant, Cas9; a chimeric Cas9; etc.) can generate a genetically modified nonhuman organism (e.g., a mouse, a fish, a frog, a fly, a worm, etc.). For example, if the genetically modified host cell is a pluripotent stem cell (i.e., PSC) or a germ cell (e.g., sperm, oocyte, etc.), an entire genetically modified organism can be derived from the genetically modified host cell. In some embodiments, the genetically modified host cell is a pluripotent stem cell (e.g., ESC, iPSC, pluripotent plant stem cell, etc.) or a germ cell (e.g., primordial germ cell, sperm cell, oocyte, etc.), either in vivo or in vitro, that can give rise to a genetically modified organism. In some embodiments the genetically modified host cell is a vertebrate PSC (e.g., ESC, iPSC, etc.) and is used to generate a genetically modified organism (e.g. by injecting a PSC into a blastocyst to produce a chimeric/mosaic animal, which could then be mated to generate non-chimeric/non-mosaic genetically modified organisms; grafting in the case of plants; etc.). Any convenient method/protocol for producing a genetically modified organism, including the methods described herein, is suitable for producing a genetically modified host cell comprising an exogenous nucleic acid comprising a nucleotide sequence encoding a CRISPR enzymer (e.g., a naturally occurring Cas9; a modified, i.e., mutated or variant, Cas9; a chimeric Cas9; etc.). Methods of producing genetically modified organisms are known in the art. For example, see Cho et al., Curr Protoc Cell Biol. 2009 March; Chapter 19:Unit 19.11: Generation of transgenic mice; Gama et al., Brain Struct Funct. 2010 March; 214(2-3):91-109. Epub 2009 Nov. 25: Animal transgenesis: an overview; Husaini et al., GM Crops. 2011 June-December; 2(3):150-62. Epub 2011 Jun. 1: Approaches for gene targeting and targeted gene expression in plants.

The constructs of the present invention are particularly useful for analyzing the transcriptome of individual cells.

Thus, the present inventors contemplate generation of RNA samples from the individual cells. The RNA may be amplified in vitro using methods known in the art and as further described in US Application No. 20150307874 the contents of which being incorporated in its entirety.

Optionally, if the constructs of the present invention encode a reporter polypeptide, the cells for analysis may be sorted by selecting cells which express said reporter polypeptide. When the reporter polypeptide is a fluorescent polypeptide (e.g. BFP or GFP), the cells may be selected using a FACS machine, or visualized by microscopy. When more than one gRNA construct is introduced into the cell, the present inventors contemplate that the different constructs will further express differently colored fluorescent polypeptides and cells which express each of these fluorescent polypeptides may be selected.

According to a particular embodiment, when the gRNA is not encoded on the same expression construct as the CRISPR endonuclease protein, cells may be selected according to two reporter polypeptides a first reporter polypeptide encoded on the gRNA construct and a second reporter polypeptide encoded on the CRISPR endonuclease construct.

For synthesis of cDNA, template mRNA may be obtained directly from lysed cells or may be purified from a total RNA sample. The total RNA sample may be subjected to a force to encourage shearing of the RNA molecules such that the average size of each of the RNA molecules is between 100-300 nucleotides, e.g. about 200 nucleotides. A reverse transcriptase reaction may be carried out to convert mRNA of the sample to cDNA. For this reaction a primer is used which comprises a polydT oligonucleotide sequence.

Preferably the polydT primer sequence comprises at least 5 nucleotides. According to another is between about 5 to 50 nucleotides, more preferably between about 5-25 nucleotides, and even more preferably between about 12 to 14 nucleotides. The present inventors also contemplate using a random hexamer or octamer instead of the polydT primer.

The present invention further contemplates that the primer comprises a RNA polymerase promoter sequence at its terminal 5' end so as to be able to amplify the amount of RNA.

RNA polymerase promoter sequences are known in the art and include for example T7 RNA polymerase promoter sequence—e.g. SEQ ID NO: 14 (CGATTGAGGCC-GGTAATACGACTCACTATAGGGGC).

Preferably, the primer also contains a barcode sequence which identifies the cell source.

The primer may also comprise adaptor sequences to enable use of a next-generation sequencing platform (e.g. high throughput sequencer adapter).

The term "next-generation sequencing platform" as used herein, refers to any nucleic acid sequencing device that utilizes massively parallel technology. For example, such a platform may include, but is not limited to, Illumina sequencing platforms.

The term "high throughput sequencer adapter pair" refers to a specific nucleic acid pair that provides compatibility with a massively parallel sequencing platform (i.e., for example, Illumina sequencer adapter pairs). For example, an adapter pair may comprise the hybridization between a high throughput sequencing primer that is complementary to a high throughput sequencing primer binding site.

Exemplary methods for preparing RNA samples from cell populations and single cells in particular for whole transcriptome analysis are provided in US Application No. 20150307874.

Kits

The constructs described herein may be provided in kits together with additional reagents for carrying out the above described methods.

Thus, according to one embodiment, the kit comprises and an expression construct which comprises DNA encoding CRISPR endonuclease and the following expression construct:

(i) a DNA sequence which encodes at least one guide RNA (gRNA) operatively linked to a transcriptional regulatory sequence so as to allow expression of said gRNA;

(ii) a barcode sequence for identification of said at least one gRNA operatively linked to a transcriptional regulatory sequence so as to allow expression of said barcode sequence.

Alternatively, the kit may comprise reagents which are necessary to carry out whole cell transcriptome analysis together with the expression constructs of the present invention. Such reagents include for example an oligonucleotide comprising a polydT sequence at its terminal 3' end, a RNA polymerase promoter sequence at its terminal 5' end and a barcode sequence positioned between said polydT sequence and the RNA polymerase promoter sequence.

Preferably, each of these components are packaged in separate packaging.

Additional reagents which may be included in the kit for whole transcriptome analysis include T4 RNA ligase, RNAseH, DNase, sequencing adaptors and/or a reverse transcriptase.

The containers of the kits will generally include at least one vial, test tube, flask, bottle, syringe or other containers, into which a component may be placed, and preferably, suitably aliquoted. Where there is more than one component in the kit, the kit also will generally contain a second, third or other additional container into which the additional components may be separately placed. However, various combinations of components may be comprised in a container.

When the components of the kit are provided in one or more liquid solutions, the liquid solution can be an aqueous solution. However, the components of the kit may be provided as dried powder(s). When reagents and/or components are provided as a dry powder, the powder can be reconstituted by the addition of a suitable solvent.

A kit will preferably include instructions for employing, the kit components as well the use of any other reagent not included in the kit. Instructions may include variations that can be implemented.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Methods

Mice:

Cas9-GFP transgenic mice were previously described (Platt et al., 2014). A founding breeding pair was purchased from The Jackson Laboratory. These mice were bred in the Weizmann Institute animal facility and backcrossed with wild-type black (C57Bl/6); their progeny was crossed to produce Cas9-GFP homozygotes on a cleaner C57Bl/6 background. In all experiments, wild-type black or Cas9-GFP young adult (7-11 weeks old) females were used. Mice were provided with food and water ad libitum and housed under a strict 12-hour light-dark cycle. All experimental procedures were approved by the Institutional Animal Care and Use Committee (IACUC).

Single Guide RNA and Unique gRNA Index (UGI):

For targeted loss-of-function screening using cell cytometry, the lentiviral vector lentiGuide-Puro (Platt et al., 2014) (plasmid #52963, Addgene) was used and the puromycin resistance marker coding sequence (CDS) was replaced with either fluorophore EBFP or mCherry CDS. The gRNA cannot be identified during single-cell gene expression library construction, due to its short size and lack of a polyadenylation tail. Therefore, to detect the gRNA in single cells in experiments where a mix of lentiGuide vectors with different gRNA are used, a unique gRNA identifier (UGI) barcode was expressed at the 3' end of the fluorophore transcript, immediately downstream to the Woodchuck hepatitis virus posttranscriptional regulatory element (WPRE) (Zufferey et al., 1999) and upstream to the polyadenylation signal in the lentiviral construct (FIG. 1A). A library of UGIs, located 372 base-pairs (bp) upstream to the SV40 poly(A) signal, is processed in parallel to single-cell gene expression profiling (Jaitin et al., 2014). To incorporate UGIs in the lentivectors, a BamHI restriction site was introduced immediately downstream to the WPRE. The random (N) 8 bp-long UGI sequences were synthesized in single stranded DNA (ssDNA) oligonucleotides with flanking sequences of homology with the following vector insertion site: ctcccttttgggccgcctcCCCGCGTCGACG-GATCCNNNNNNNNGacttacaaggcagctgtaga (SEQ ID NO: 1), and were then amplified by PCR using primers matching these flanking regions (marked by lowercase letters). The insertion of the barcode sequences was performed by Gibson assembly cloning (Gibson et al., 2009) to lentiGuide vectors digested with BamHI. Guide RNAs were cloned into the lentiGuide vectors as previously described (Sanjana et al., 2014). Briefly, gRNAs synthesized in pairs of oligonucleotides (IDT) with BsmBI-compatible overhangs were phosphorylated with T4 polynucleotide kinase (NEB) and annealed. The fragments were then ligated with BsmBI-digested and purified lentiGuide-UGI plasmids. Ligated constructs were transformed into competent bacteria and, following picking of single clones and plasmid purification, each gRNA was paired with its identifying UGI by Sanger sequencing.

Lentivirus Production:

LentiGuide-UGI lentiviral particles were produced by transfecting 293T cells together with packaging plasmids, using the jetPEI transfection reagent (Polyplus-transfection) according to the manufacturer's instructions and following the standard lentivirus production protocol (Klages et al., 2000). Transfection efficiency was assessed by microscopic inspection of cell fluorescence one day later. Media was replaced with RPMI medium without additives 18 h post transfection, and media containing virus particles were collected 48 and 72 h post transfection. Virus particles were concentrated using Amicon 100 KDa 15 mL columns (Millipore) in a cold centrifuge at 2000×g to a final concentration of 200-250 µl per virus, aliquoted and stored at −80° C. until use.

Isolation and Culture of Bone Marrow-Derived Myeloid Cells:

Mice were sacrificed by cervical dislocation. To isolate the bone marrow, femora and tibiae from one leg were removed, cleaned from flesh, and flushed with C10 culture medium (RPMI supplemented with 15% serum, 1%×100 non-essential amino acids, 10 mM Hepes buffer, 1 mM sodium pyruvate, 2 mM L-glutamine, 1% L-glutaine and 50 µM b-mercaptoethanol) using a G21 needle syringe. The bone marrow was filtered through a 70-µm cell strainer and spun down in a cold centrifuge at 300×g for 5 min. Cells were resuspended in 250 µl red blood cell lysis solution (Sigma) per leg and incubated for 5 min at room temperature, washed, and resuspended in C10 medium. Cultures were set by plating $6 \times 10^5$ cells in 1 ml C10 supplemented with 15 ng/ml GM-CSF in a 6-well non-tissue culture plate, and incubated under standard culture conditions (37° C., 5% $CO_2$). Cells were infected on culture day 2 by adding lentivirus and 8 µg/ml polybrene, and plates were centrifuged 1000×g at 37° C. for 45 min to enhance infection. At the end, 1 ml C10+GM-CSF was added. Cells were fed with 200 µl C10 supplemented with 30 ng/ml GM-CSF every second day.

Flow Cytometry and Single-Cell Capture:

On day 7, cells were either treated with 100 ng/ml lipopolysaccharide (LPS) for 4 h or left untreated as control. To obtain cell suspension, cells were scraped from the well, washed and resuspended in cold FACS buffer (0.5% BSA and 2 mM EDTA in phosphate-buffered saline), stained with fluorophore-conjugated anti-mouse CD11c (and CD11b where indicated) antibody (BioLegend), and filtered through a 40-µm strainer. Cell sorting was performed using a BD FACSAria Fusion flow cytometer (BD Biosciences), gating for GFP (Cas9), and relatively high BFP or mCherry fluorescence (FIG. 7C; CRISP-seq lentivirus-infected cells). This gate was chosen according to the maximal CD11b marker mean signal reduction in cells infected with Itgam-gRNA (the gene coding for CD11b), used to calibrate the system. Single cells were sorted into 384-well capture plates containing 2 µl of lysis solution and barcoded poly(T) reverse-transcription (RT) primers for single-cell RNA-seq as described previously (Jaitin et al., 2014). To record marker levels of each single cell, the FACS Diva 7 "index sorting" function was activated during single-cell sorting. Results were exported into an Excel file containing the information about flow parameters of each cell (each well). Immediately after sorting, plates were spun down to ensure cell immersion into the lysis solution, snap frozen on dry ice and stored at −80° C. until further processing.

In Vivo CRISP-Seq Assay:

Hematopoietic stem cells (HSCs) and multiple pluripotent progenitors (MPPs) were isolated from the bone marrow of Cas9-GFP donor mice, infected with a pool of CRISP-seq lentivirus containing the BFP fluorophore gene and different gRNAs, and injected into wild-type recipient mice (FIG. 6A). Seven days post-transplantation, spleens were removed and single cell sorted for CRISP-seq analysis. On day 1, bone marrow from Cas9-GFP mice was isolated from mouse tibiae femora and ilia leg bones, filtered through a 70 mm cell strainer, and the cell suspension enriched for c-kit expressing cells using magnetic cell separation (Miltenyi Biotec Germany; #130-091-224) according to manufacturer's instructions. Cells were then stained and FACS-sorted using a sterilized FACSAria Fusion cell sorter (BD Biosciences) into a tube already containing 500 µl of StemSpan supplemented with standard tissue culture penicillin/streptavidin (pen/strep) antibiotics. HSCs and MPPs were defined as $GFP^+$ $Lin^-$ (lineage negative) $Sca1^+$ $c-kit^+$ (LSK). Lineage markers included: anti-mouse Ter-119, Gr-1, CD11b, B220, CD19, CD3, CD4, and CD8, as previously described (Paul et al. 2015). About 90,000 donor cells were infected with a CRISP-seq lentivirus pool in tissue-culture 96-well plates for about 18 hours. The infection was carried out in 200 µl StemSpan medium (Stemcell technologies) supplemented with the cytokines Flt3, Il3, Tpo and SCF (stem cell factor), each at 10 ng/ml, and pen/strep antibiotics. On day 2, prior to bone marrow transplantation, wild-type recipient 8 weeks-old female mice were lethally irradiated with two subsequent X-ray doses of 550 cGy and 500 cGy that were administered 3 hours apart. After irradiation, drinking water was supplemented with 200 mg ciprofloxacin/ml. Four to six hours post irradiation, the donor cells were collected, washed twice with PBS and injected intravenously (tail injection) together with 200,000 recipient isogenic (wild-type) flushed whole bone marrow carrier cells for myelo-protection, 200 µl per mouse. On day 8, recipient mice were IP injected with either LPS (Sigma # L2880), 1 ng per 5 gr mouse, or PBS and 4 hours later, mice were sacrificed, their spleen extracted and dissociated into single splenocytes with a gentleMACS Dissociator (Miltenyi Biotec, Germany), filtered through a 70-µm strainer and incubated 5 min. in red blood cell lysis solution (Sigma R7757). After washing, cells were stained and single-cell sorted as described above. The myeloid niche coming from the donor was defined as GFP+ BFP+ lymphocyte-negatives (as CD19-TCRb-CD3-NK1.1−), and CD11c+, CD11b+ or Ly6g+.

CRISP-Seq Library Preparation:

Libraries of single-cell gene expression (MARS-seq) and single-cell gRNA detection (UGI-seq) together with CRISP-seq, were prepared in parallel. For automated library production, Bravo robot station was used in combination with Nanodrop Express (BioNex, San Jose, Calif.). MARS-seq libraries were prepared as previously described (Jaitin et al., 2014). Briefly, mRNA from sorted cells was simultaneously barcoded, converted into cDNA and pooled using an automated pipeline. The pooled samples were then linearly amplified by T7 in vitro transcription (IVT). After DNase treatment, the samples were cleaned up with 1.2×SPRI beads and the amplified RNA (aRNA). Half of the aRNA was fragmented and converted into a sequencing-ready library by tagging the samples with pool barcodes and Illumina sequences during ligation, RT, and PCR. For the corresponding gRNA information in each cell, a UGI-seq library was obtained from 10-12% of the aRNA material, and processed in parallel as follows: Fragmentation was skipped and ligation was done together with MARS-seq samples, using the UGI ligation primer (Table 1; pool barcode was added at a later step). Ligation cleanup and the subsequent reverse transcription (RT) reaction were the same as for MARS-seq samples, except for the use of a different RT primer (Table 1). Then, an intermediate 10-cycle PCR step was done to amplify and add pool barcodes, using a barcoded forward primer and the reverse primer used in MARS-seq final step (Table 1); PCR conditions were the same as in MARS-seq. Finally, another PCR reaction, as in MARS-seq, was done to complete and enrich the UGI-seq library. The resulting CRISP-seq product is a MARS-seq library and a corresponding UGI-seq library. Library quality assessment and concentration measurements were performed as previously described (Jaitin et al., 2014).

TABLE 1

Primers used for UGI-seq library construction

| Primer name | Sequence |
|---|---|
| UGI ligation adapter | ATGATCAAGCGACCACCGAG (SEQ ID NO: 2), modified with a phosphate group at the 5' end, and a C3 spacer (blocker) at the 3' end |
| Second RT UGI primer | CTCGGTGGTCGCTTGATCAT (SEQ ID NO: 3) |
| Barcoded PCR forward | CTACACGACGCTCTTCCGATCTNNNNNNXXXXTCCCC GCGTCGACGGATC (SEQ ID NO: 4), N = random base and XXXX = 4-bases plate barcode |
| P7_Rd2 PCR reverse | CAAGCAGAAGACGGCATACGAGATGTGACTGGAGTT CAGACGTGTGCTCTTCCGATCT (SEQ ID NO: 5) |

Sequencing and Low-Level Processing:

CRISP-seq libraries, pooled at equimolar concentrations, were sequenced using an Illumina NextSeq 500 sequencer, at a sequencing depth of 60K-80K reads per cell for MARS-seq and about 4K reads per cell for UGI-seq. Reads are condensed into original molecules by counting same random molecular tags (RMT, a.k.a. unique molecular identifier or UMI). Statistics on empty-well spurious RMT detection was used to ensure that the batches we used for analysis showed a low level of cross-single-cell contamination (less than 1%).

CRISP-seq reads were processed as previously described (Gury-BenAri et al., 2016). Mapping of reads was done using HISAT (version 0.1.6); reads with multiple mapping positions were excluded. Reads were associated with genes if they were mapped to an exon, using the UCSC genome browser for reference. Exons of different genes that shared genomic position on the same strand were considered a single gene with a concatenated gene symbol. Cells with less than 1500 UMIs were discarded from the analysis. Genes with mean expression smaller than 0.005 RMTs/cell or with above average expression and low coefficient of variance (<1.2) were also discarded.

UGI-Seq Low-Level Processing:

Sequenced reads containing the UGI-seq 5' primer (TCCCCGCGTCGACGGATCC—SEQ ID NO: 6) up to 2 bp mismatches were extracted for further UGI-seq processing. Plate barcode, cell-specific barcode (7 bp), Random Molecular Tags (RMT—8 bp) and Unique Guide Identifier (UGI—8 bp) was extracted for each read. Reads with low quality (Phred<27) or without a valid UGI sequence (up 1 bp mismatch), cell barcode (up 1 bp mismatch), or plate barcode (exact match) were discarded. Sequencing errors within a RMT may undermine the UGI counts by creating spuriously identified molecules from real molecules; this number is expected to increase linearly with sequencing depth. As UGI molecules were over-sequenced, these 'satellite' reads were easily detectable, and real molecule reads (in log scale) were normally distributed with an average of $2^{10}$ duplicated triplets (cell barcode, RMT, UGI) and a standard deviation of 2. Triplets with less than 30 reads were discarded as errors (p<0.01, see FIG. 7D) and each cell received a vector of UGI molecule counts. In some analysis, the total number of reads with the same cell barcode and UGI were considered (e.g. y-axis in FIG. 1B). To assign a binary label per cell, we consider UGI molecules >1 as positive cells (See FIG. 7D).

Graph-Based Clustering Analysis:

In order to assess the heterogeneity of cells in the samples, the PhenoGraph clustering algorithm was used (Levine et al., 2015). Briefly, low-level processing of CRISP-seq reads results in a matrix U with n rows and m columns, where rows represent genes and columns represent cells. Entry Uij contains the number of unique molecular identifiers (UMIs) from gene i that were found in cell j. The first step of the algorithm is to build a graph structure from this expression matrix. PhenoGraph first builds a k-Nearest Neighbors (kNN) graph using the Euclidean distance (we chose k=30 and tested k=15, 20, 25, 30, 40, 50, and got very similar results, not shown) and then refines this graph with the Jaccard similarity coefficient, where the edge weight between each two nodes is the number of neighbors they share divided by the total number of neighbors they have (Levine et al., 2015). To partition the graph into modules/communities PhenoGraph uses the Louvain Method (Blondel et al., 2008).

The graph is constructed and partitioned into modules based on the expression profile of the cells. The genotype information obtained from UGI-seq can now be overlayed to calculate the enrichment of gRNA within clusters. The UGI enrichment p-value within each cluster can be calculated using the hyper geometric distribution, where N is the total number of cells, K is the number cells with $UGI_A$, n is the size of cluster $c_i$ and k is the number of cells with $UGI_A$ in cluster $c_i$. The probability of drawing k or more cells with $UGI_A$ is:

$$p = F(k \mid N, K, n) = \sum_{i=k}^{n} \frac{\binom{K}{i}\binom{N-K}{n-i}}{\binom{N}{n}}$$

Graph Based Label Refinement Algorithm:

UGI-seq provides information on the expression of the reporter gene introduced in our lentivirus construct. This information is translated to a specific gRNA which was integrated together with the reporter gene. This gRNA will target Cas9 to a specific gene locus, but only in 70-80% will generate true loss-of-function of the targeted gene (Sternberg and Doudna, 2015). In other cases, Cas9 may generate a non-harmful mutation (such as in-frame deletion) or no mutation at all. This implies that in 20-30% of the cells with a unique guide index, the gene can be active or partially active and show a wild-type phenotype (false positive). On the other hand, as single-cell data is sparse by nature, cells with true edited gene loss-of-function can remain undetected by UGI-seq, becoming false negative events. The single-cell RNA detection error is quantified as 20% by comparing UGI-seq to FACS-based detection of the BFP fluorophore. In order to overcome the noisy and missing genotype label problem, a label refinement algorithm was used that can modify the labels themselves. This algorithm is based on the assumption that the labels (=genotype) of the cells are consistent with their nearest neighborhoods, i.e. that cells sharing the same knockout mutation will have similar phenotype and this phenotype is distinct from the wild-type phenotype. The input data dataset S=(X, Y). The expression matrix is denoted as X, where X={$x_1, x_2, \ldots, x_N$} each cell expression $x \in \mathcal{R}^M$ is an M-dimensional vector. Their corresponding UGI labels are Y={$y_1, y_2, \ldots, y_N$}, where $y \in \{0,1\}^K$ is a binary vector representing the UGIs detected in each cell. Our algorithm refines each UGI label separately. Based on the expression matrix we first build a Jaccard graph, similar to a PhenoGraph construction of the graph. An initial kNN graph in constructed based on the Euclidean distance between cells and the Jaccard index is calculated for every pair of nodes. The weight between nodes i and j, is given by:

$$W_{ij} = \frac{|v(i) \cap v(j)|}{|v(i) \cup v(j)|}$$

where v(i) is the k-neighborhood of cell i. Our two step algorithm first remove labels which disagree with their neighborhood and then assign labels to cells with significant neighbor's enrichment. For each cell, we define a neighborhood score for each UGI u as the sum of the Jaccard coefficients with all other labeled nodes in the graph:

$$s(i) = \sum_{j \in V, y_j^u = 1} W_{ij}$$

(most coefficients will be zero as most cells do not share common neighbors in the kNN graph). To calculate the p-value of observing this score at random, we used bootstrapping, shuffling the labels randomly 100K times and counting the number of times s(i) is bigger than the score obtained in each shuffled graph. Labels were removed from cells with p-value >0.05. In the next step, we repeated this process with the new filtered labels and added labels for cells with p-value <0.001. Changing the bounds within a reasonable range (0.01-0.2 for filtering out labels and 0.01-1e-5 for adding labels) modified the total number of labeled cells, but they still remained in the same neighborhood.

Perturbation Fold Change Analysis:

The present inventors calculated the perturbation effect for each gene knockout by comparing perturbed cells with the corresponding control group. Groups were selected either by label refined cells vs. all control cells (FIGS. 4A-H and 5A-F) or by comparing clusters enriched for perturbation vs. control. Scatterplots show $\log_2$ mean RMT counts in each group. P-values were calculated using the Mann-Whitney U test (matlab 2016a ranksum function)

CRISPR/Cas9 Editing Assessment (Indel-Seq Analysis)

Cell Sorting:

About 4,000 cells per sample were sorted into a microfuge tube already containing 500 µl of cold FACS buffer. Tubes were gently vortexed and cells were pelleted in a cold centrifuge, at 1,500×g for 15 min at 4° C., to aspirate most of the supernatant, leaving about 50 µl, and stored at −80° C. until further processing.

Genomic DNA Extraction:

Cells were lysed by three cycles of freeze/thaw by 37° C. and dry ice incubation of 3 min each. Then SDS was added to a final concentration of 0.5% and the samples were incubated for 5 min at room temperature. Then, samples were incubated in RNase, DNase-free (Roche), 0.5 µl per 50 µl sample, for 30 min at 37° C. Next, two units of proteinase K (NEB) and 5 nM EDTA were added and samples were incubated at 37° C. for 2 h, followed by incubation at 65° C. overnight. Alternatively, samples were incubated at 37° C. for 30 min and then at 95° C. for 10 min. Genomic DNA was cleaned up using 2.5 volumes of SPRI beads, and mass concentration was measured in a Qubit fluorometer with high-sensitivity DNA reagents (ThermoFisher Scientific).

Indel-Seq Library Construction:

Libraries were constructed around each exon-specific region in two PCR reactions, using target-specific primers with Illumina partial tags as overhangs for PCR1, and a second PCR to amplify and add the missing parts for Illumina sequencing (Table 2). PCR1 protocol: To 5 ng of genomic DNA add 2 µl primer mix at 10 µM each primer, 25 µl 2×KAPA high-fidelity PCR mix (KAPA Biosystems, Roche), 50 µl reaction volume, 28 cycles. PCR program: 2 min at 98° C., 2 min, 28×[20 sec. at 98° C., 30 sec. at 60° C., 40 sec. at 72° C.], 5 min at 72° C., 4° C. end. Clean up the PCR1 product with 40 µl of SPRI beads (0.8 volumes). Measure concentration and assess expected size in a TapeStation instrument using high-sensitivity DNA reagents (Agilent Technologies) before PCR2. PCR2 protocol: To 5 ng of PCR1 product, add 1 µl of 10 µM P5_Rd1 primer, 1 µl of 10 µM indexed reverse primer, choosing specific barcodes for each sample, 10 µl 2×KAPA high-fidelity PCR mix, 20 µl reaction volume, 5 cycles. PCR program: 2 min at 98° C., 2 min, 2 cycles×[20 sec. at 98° C., 30 sec. at 58° C., 45 sec. at 72° C.], 3 cycles×[20 sec. at 98° C., 30 sec. at 65° C., 45 sec. at 72° C.], 5 min at 72° C., 4° C. end. Clean up the PCR2 product with one volume of SPRI beads. Measure molar concentration with Qubit and TapeStation. Indel-seq libraries were sequenced using a Miseq Illumina sequencer and the primers listed in Table 2.

TABLE 2

Primers used for Indel-seq library construction

| Primer name | Sequence |
|---|---|
| Cebpb Indel-seq pRd1 | ACACGACGCTCTTCCGATCTCCTGGTAGCCCAGGTA GGC (SEQ ID NO: 7) |
| Cebpb Indel-seq pRd2 | CTGGAGTTCAGACGTGTGCTCTTCCGATCTTCTCCG ACCTCTTCGCCG (SEQ ID NO: 8) |
| Itgam Indel-seq pRd1 | ACACGACGCTCTTCCGATCTTGTCTGGTTAACAGCC TTTG (SEQ ID NO: 9) |
| Itgam Indel-seq pRd2 | CTGGAGTTCAGACGTGTGCTCTTCCGATCTCCATTT CCCATCCTAACTTC (SEQ ID NO: 10) |
| P5-Rd1 forward | AATGATACGGCGACCACCGAGATCTACACTCTTTCC CTACACGACGCTCTTCCGATCT (SEQ ID NO: 11) |
| P7-i7-pRd2 reverse | CAAGCAGAAGACGGCATACGAGATXXXXXXXGTGAC TGGAGTTCAGACGTGTGCT, XXXXXXX = 7 bases index (SEQ ID NO: 12) |

Example 1

CRISP-Seq: An Integrated Method for Single-Cell RNA-Seq and CRISPR Pooled Screens To elucidate the function of multiple regulatory factors at single-cell and genome-wide resolution, CRISP-seq was developed, an integrated method for pooled CRISPR/Cas genome editing followed by massively parallel single-cell RNA-seq. For this protocol, a scalable lentiviral backbone (CRISP-seq vector) was engineered that takes full advantage of the combination of massively parallel single-cell RNA-seq with FACS index sorting. In addition to a gRNA expression cassette, the lentivirus includes a unique gRNA index (UGI), which is transcribed and allows the identification of the gRNA from single-cell RNA-seq data (FIG. 1A). Importantly, the lentivirus was also engineered to include a fluorescent selection marker that enables study of perturbed cells from specific niches in animal models. The combination of a gRNA index with the single-cell transcriptome data enables generation of deep and comprehensive phenotype profiling of multiplexed gene knockouts, and to study their function and interactions in a single experiment (FIG. 1A).

Figure 1C:
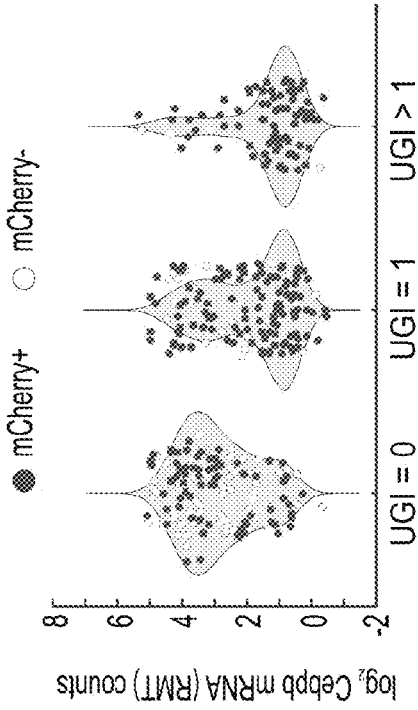
Figure 1F:
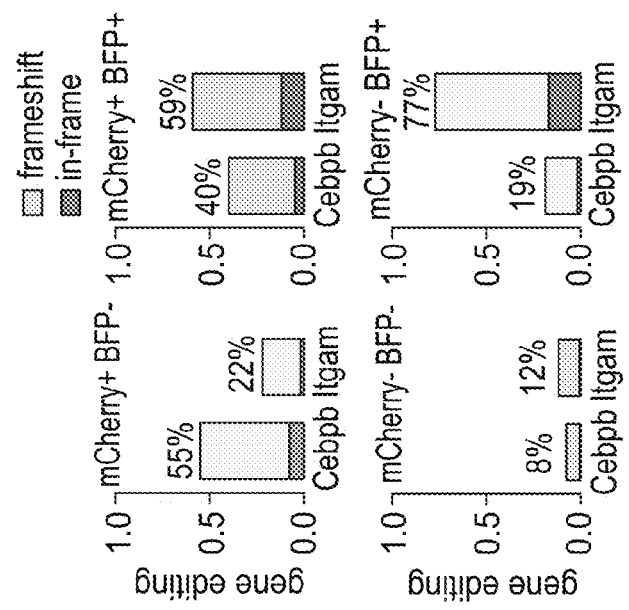
Figure 1E:
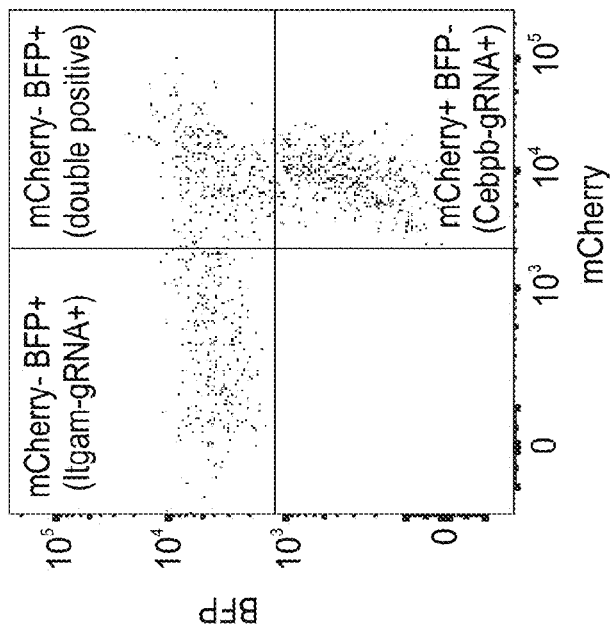
Figure 1D:
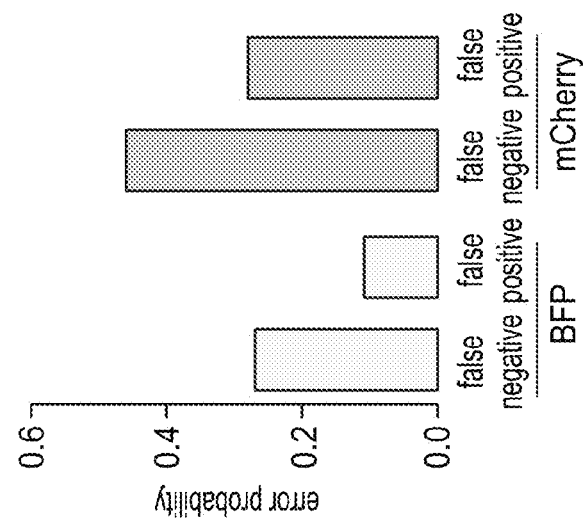
Figure 7D:
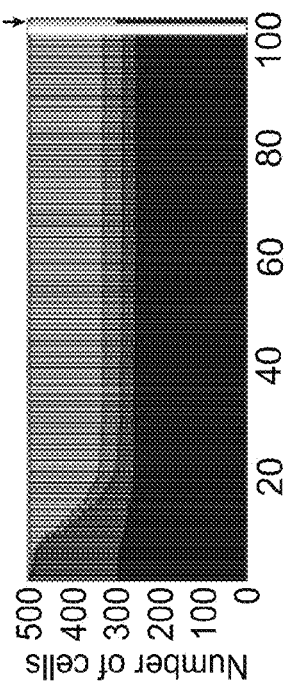
Figure 7D:
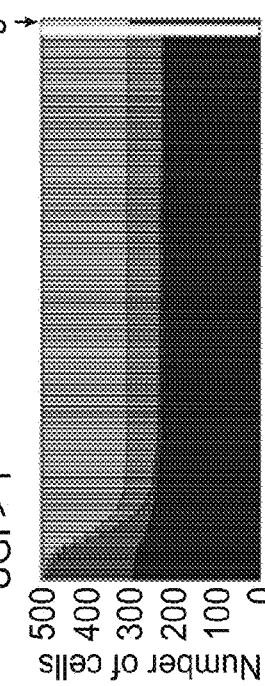

The CRISP-seq protocol is highly reproducible for identifying the transcriptome in combination with the gRNA (FIGS. 1B-D). To benchmark CRISP-seq, the present inventors cloned into the backbone a gRNA targeting the Itgam gene, which encodes for the CD11b integrin, alongside a blue fluorescent protein (BFP) marker and a specific UGI barcode (Methods and Resources). Bone marrow cells from C57BL/6 female mice harboring a GFP-labeled Cas9 knockin (Platt et al., 2014) were infected with lentiviruses expressing gRNA(CD11b)-BFP-UGI. Five days later, infected GFP$^+$BFP$^+$CD11c$^+$ myeloid-derived cells were sorted for massively parallel single-cell RNA-seq analysis (Methods and Resources). Information on BFP and CD11b intensities was recorded for each cell by index sorting (Paul et al., 2015). Comparison of CD11b protein expression levels and BFP intensities showed that in 81% of the cells with high levels of BFP signal (Itgam-gRNA$^+$), CD11b expression decreased substantially (FIG. 1B). Comparing the UGI read counts with CD11b and BFP intensities in each cell showed a high concordance among BFP-positive cells, CD11b perturbation and CD11b-UGI expression (FIGS. 1B and 7A). CD11b-UGI was detected with 84% precision, computed as the sum of true positive and true negative events relative to the BFP FACS signal, and false positive and false negative events of 4% and 12%, respectively (FIGS. 1B and 7D).

Figure 7E:
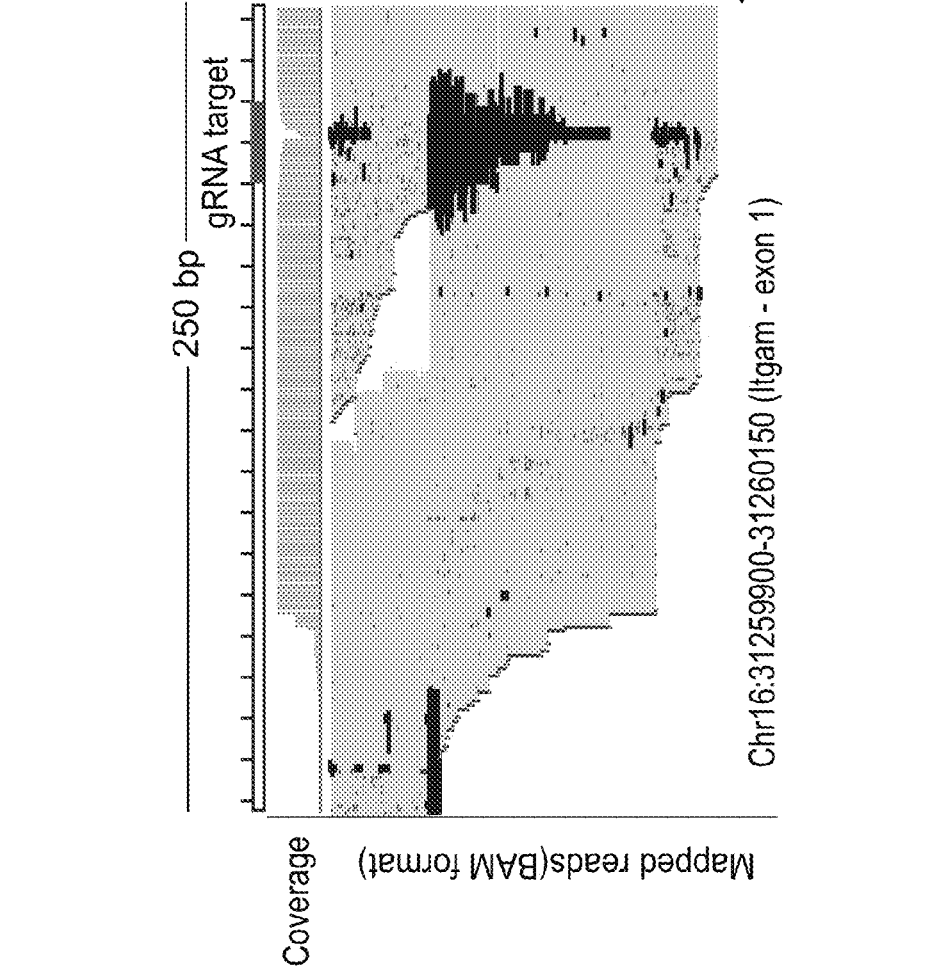
Figure 8A:
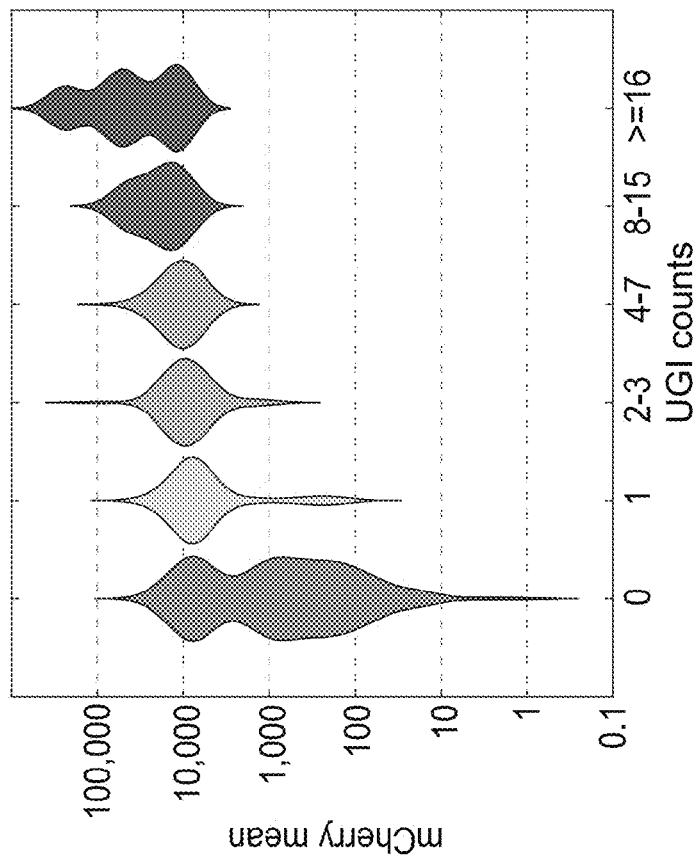
Figure 8B:
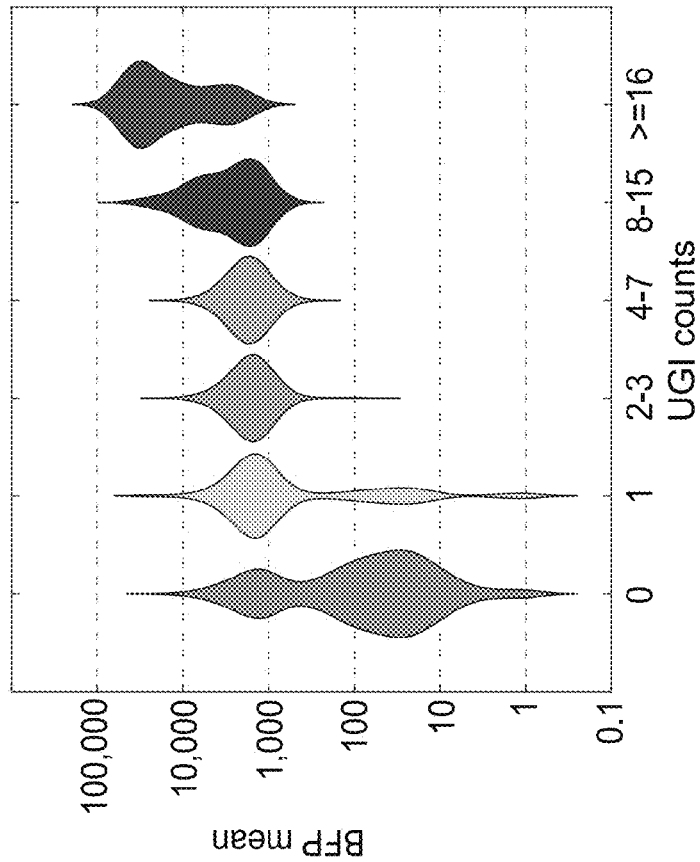
Figure 9B:
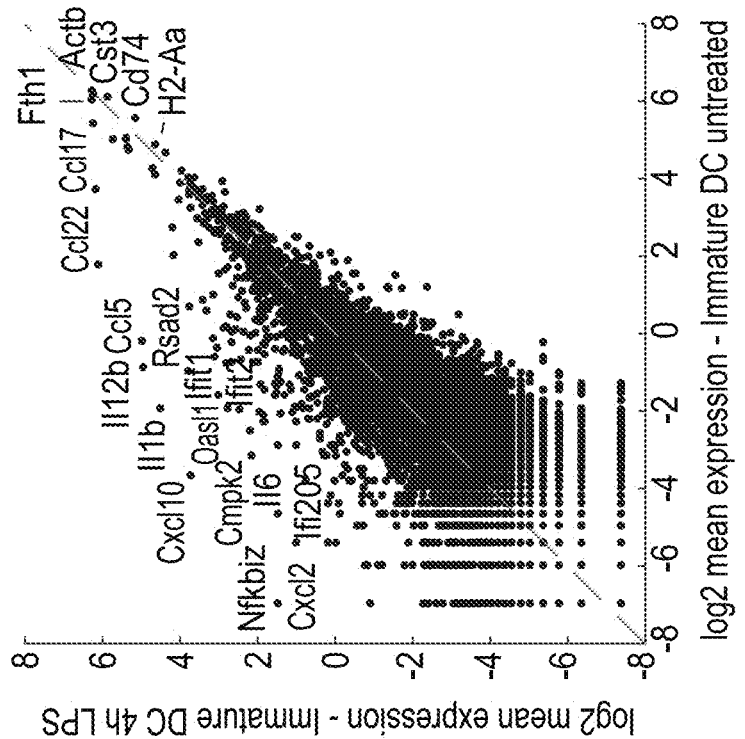
Figure 9A:
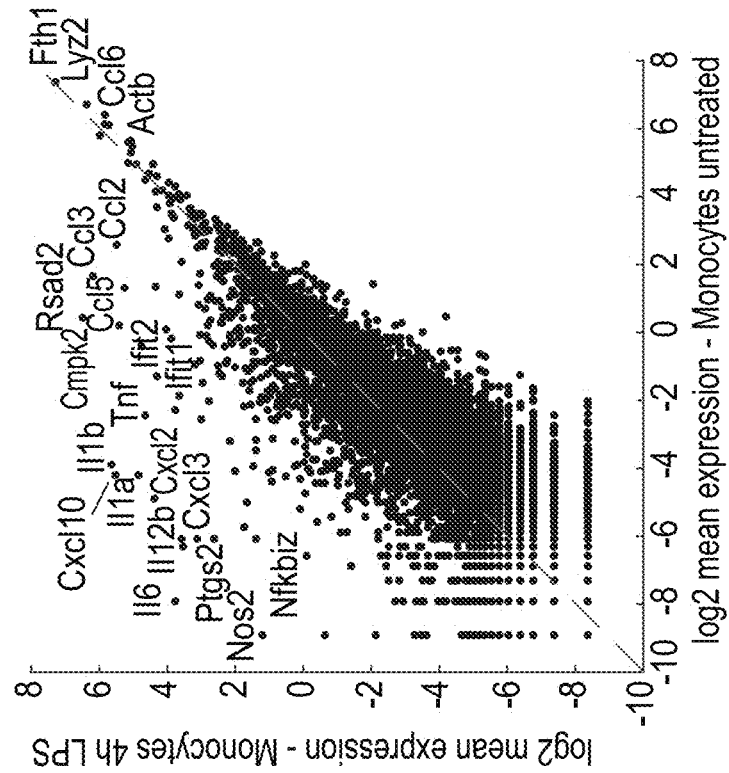

To evaluate the potential of applying CRISP-seq for multiplexed genome editing, the accuracy of detecting individual gRNAs and their combinations was assessed. For this purpose, an mCherry fluorescent marker was cloned together with a gRNA targeting the Cebpb gene, and bone marrow cells were infected with a combination of mCherry/Cebpb-gRNA and BFP/Itgam-gRNA. Myeloid cells were sorted for massively parallel single-cell RNA-seq analysis and indexed for BFP, mCherry, and CD11b intensities. Successful Cas9 editing cleaves the gRNA complementary seed sequence in the DNA, creating mutations and small insertions and deletion (indels), but do not necessarily impact RNA expression directly. Because transcription factors are often regulated through auto-regulatory loops, their mRNA expression can potentially serve as a proxy for gRNA activity. The comparison of Cebpb mRNA expression vs. mCherry intensities (Cebpb-gRNA$^+$) in single cells showed a strong correlation between the mCherry signal and Cebpb expression (FIGS. 1C and 7B). Overlapping the UGI read counts with mCherry expression revealed high correlation among mCherry-positive cells, Cebpb perturbation and Cebpb-UGI expression (FIGS. 1C and 7B). These experiments also confirm that the BFP marker was more effective in labeling infected cells and displayed a lower false negative rate, with better correlation among fluorescence intensity, UGI detection and gene editing (FIGS. 1D-F and FIGS. 7B-D). To evaluate the genome editing efficiencies within UGI-positive cells targeting CD11b, Cebpb and multiplexed CD11b and Cebpb, the present inventors sorted BFP−/mCherry−, BFP+/mCherry−, BFP−/mCherry+ and BFP+/mCherry+ cells (FIG. 1E). They then used primers specific to the gRNA-targeted loci to amplify and sequence these regions. Indel-seq analysis confirmed editing in the expected quadrants (FIG. 1F and FIG. 7E).

Together, these results demonstrate the robustness of combining massively parallel single-cell RNA-seq and a unique guide index strategy for accurate identification of gRNA or combinations of gRNAs in single cells.

Example 2

CRISP-Seq Analysis Identifies a Major Role for Cebpb in Monocyte Development

Figure 2A:
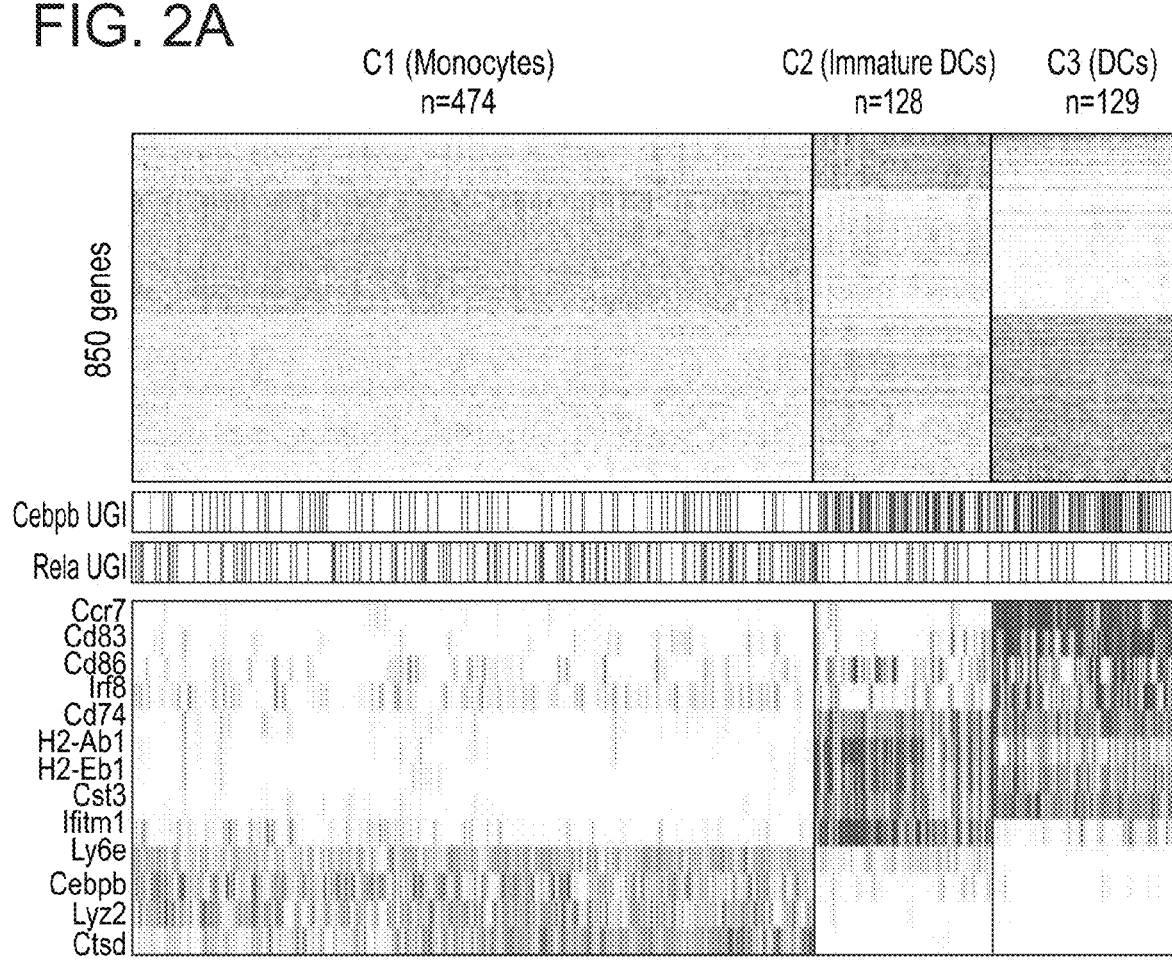
Figure 2B:
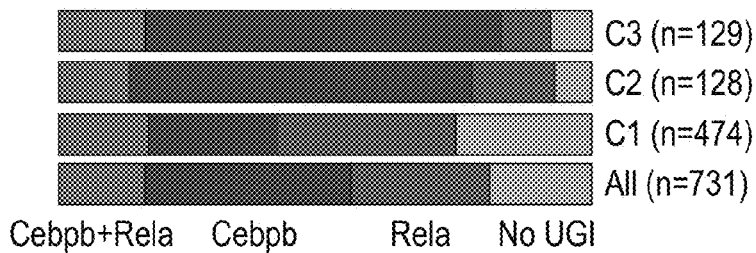
Figure 2C:
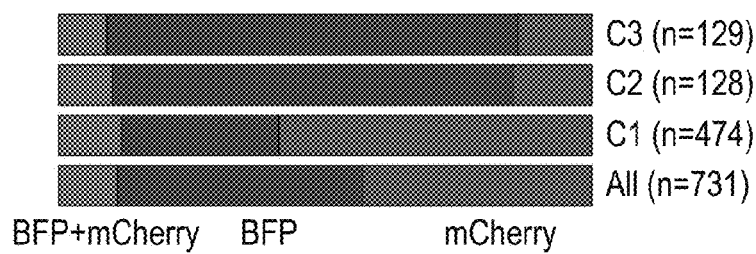

Next, the effectiveness of CRISP-seq was assessed in deciphering the function of genetic elements in a multiplexed experiment. The myeloid compartment is composed of environmental plastic cells with functional diversity in both cell state and response (Ginhoux and Jung, 2014; Glass and Natoli, 2016; Gosselin et al., 2014; Lavin et al., 2015; Lavin et al., 2014). To better understand the pathways regulating this complexity, bone marrow cells were infected with a combination of response (mCherry/Rela-gRNA) and developmental (BFP/Cebpb-gRNA) regulators, and CD11c±myeloid cells were sorted for CRISP-seq with index for BFP and mCherry intensities. Unsupervised graph-based clustering analysis (PhenoGraph (Levine et al., 2015)) identified three major myeloid cell types in the culture (FIG. 2A); a monocyte population expressing Lyz2, CD11b, Ly6c2, Cebpb and lysosomal peptidases (Ctsb, Ctsd and Ctss), and two dendritic cell (DC) populations expressing high levels of the MHC-II pathway components (CD74, H2-Aa, etc.), Cst3, as well as checkpoint and co-stimulatory molecules (e.g. PD-L2, CD86) (Helft et al., 2015) (FIG. 2A). The two DC types could be subdivided into mature migratory DCs expressing CCR7, CCL22, CD83 and Irf8, and an immature subpopulation expressing Csf1r, Ifitm1, Fcgr3 and Lgals3 (Schlitzer et al., 2015). Using either the guide-specific fluorescent marker or the UGI indexes revealed that the two DC subtypes are significantly enriched for Cebpb knockout cells, whereas the monocytes are enriched for no gRNA (no UGI detected) and RelA KO cells (hyper-geometric p-value $<1\times10^{-4}$; FIGS. 2A-F and 8A). The present inventors confirmed these results by infecting separate cultures with single gRNA targeting Cebpb or a control gRNA, and obtained comparable cell type phenotypes and distributions to the CRISP-seq pool (FIGS. 8B-E).

To further characterize these populations and their response to pathogens bone marrow cells were infected with the same combination of Cebpb and Rela gRNAs and the myeloid culture was stimulated with the toll-like receptor 4 (TLR4) agonist lipopolysaccharide (LPS), a purified component from gram-negative bacteria, for 4 hours prior to sorting. Clustering analysis identified the same three cell types (i.e., monocytes, immature and mature DCs), which exhibited highly diverse responses to LPS (FIGS. 3A and 9A-C). The monocytes elicited a robust inflammatory response exemplified by induction of IL1a/b, IL12b and Cxcl2, as well as an antiviral response (e.g. Cxcl10, Oasl1, Ifit2, etc.) (FIGS. 3A-B). In contrast, the DC subtypes activated the antiviral pathway and induced many co-stimulatory and checkpoint molecules, with minor induction of the inflammatory genes (FIGS. 3A-B and 9B-C). Similar to the unstimulated culture, the two DC populations were significantly enriched for cells expressing the Cebpb-gRNA (FIGS. 3A-D). The present inventors observed a diminished inflammatory response in cluster II of the monocytes. This cluster was enriched for the UGI sequence matching the Rela-gRNA (hyper-geometric p-value $<1\times10^{-5}$). The response in this cluster was perturbed for dozens of inflammatory genes (Cxcl2, Il1b, Il12b and TNF), but not for antiviral response genes (FIGS. 3A-E and 9D-E). In summary, CRISP-seq analysis confirmed the known role of Rela in regulating the inflammatory response in monocytic cells. Yet, it unexpectedly uncovered Cebpb as an important factor regulating the balance between DC and monocyte development (Feng et al., 2008; Heinz et al., 2010). When Cebpb is perturbed, cells are pushed towards the DC lineage expressing high levels of Irf8. Furthermore, the present analysis showed that these two myeloid types boosted a dramatically different response to LPS. The plasticity in differentiation and rewiring of response pathways of myeloid cells would have made these results difficult to interpret without single-cell analysis coupled to perturbations (Paul et al., 2015).

Example 3

Decoupling of Antiviral and Inflammatory Pathways by Multiplexed Perturbations

To better characterize the genotype-to-phenotype relation in single cells by CRISP-seq and to identify multiplexed perturbations, the present inventors developed an algorithm that would most accurately detect perturbed single cells with distinct phenotypes. Their framework relies on the assumption that cells with similar genotypes will be in closer proximity in the phenotypic space; hence, a cell with a true loss-of-function hit will generate a similar phenotype that is different from in-frame mutations or non-targeted cells. Using this assumption, they sought to overcome two sources of potential outliers in their data, namely false positives and false negative cells. Regarding the former, targeting of Cas9 to specific gene locus generates loss-of-function mutation/indels in up to 80% of the loci (Sternberg and Doudna, 2015). This implies that for any single cell for which a UGI was detected, there is at least a 20% chance that the targeted gene is fully or partially active. Conversely, with the current CRISP-seq/UGI strategy, up to 20% of the cells will remain undetected, but can potentially carry the knockout. In order to overcome the noisy and missing genotype labeling, the present inventors developed a label refinement algorithm based on k-Nearest Neighbors (kNN) graph (Blondel et al., 2008; Girvan and Newman, 2002; Levine et al., 2015) to correct the genotype labeling based on the genotype of neighboring cells (FIGS. 4A-B; Methods and Resources). In the first step after graph generation, cells that are connected to other cells with the same genotype more than expected by chance (bootstrap p-value <0.05) maintained their UGI label, whereas cells that are in disagreement with their neighbors lose their label. In the second step, the present inventors propagated the genotype labels to cells with missing labels based on the genotype of their neighbors.

Figure 4C:
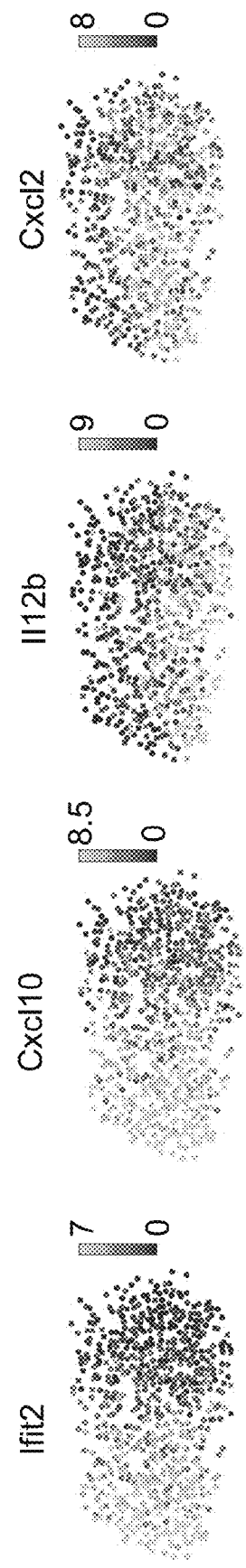
Figure 4D:
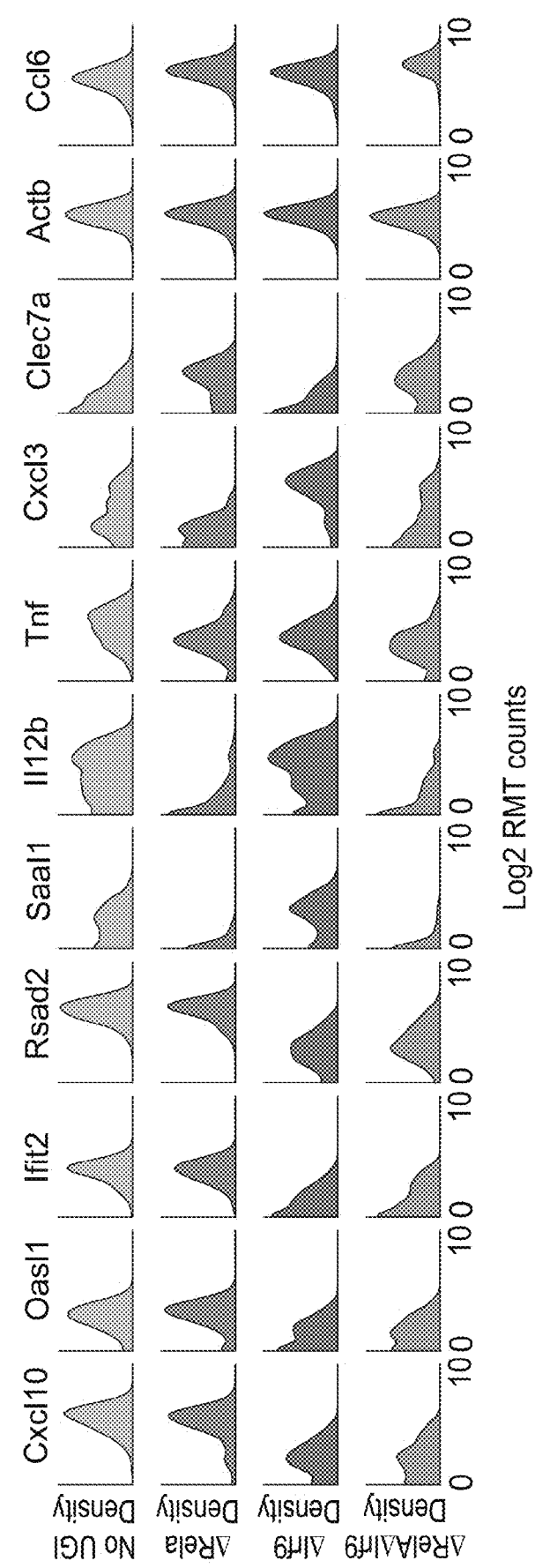
Figure 4E:
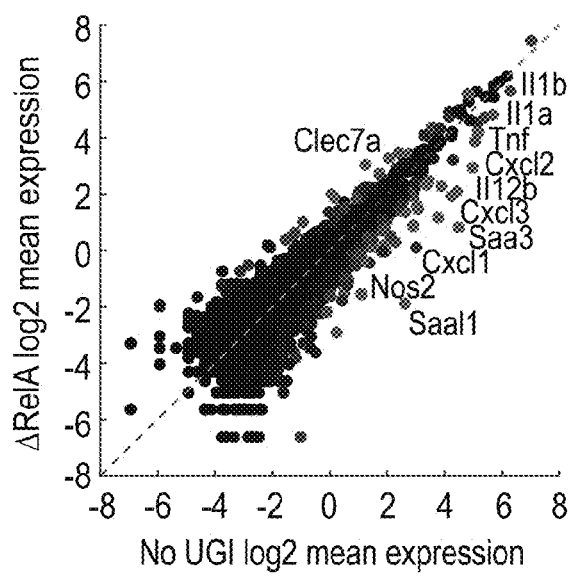
Figure 4F:
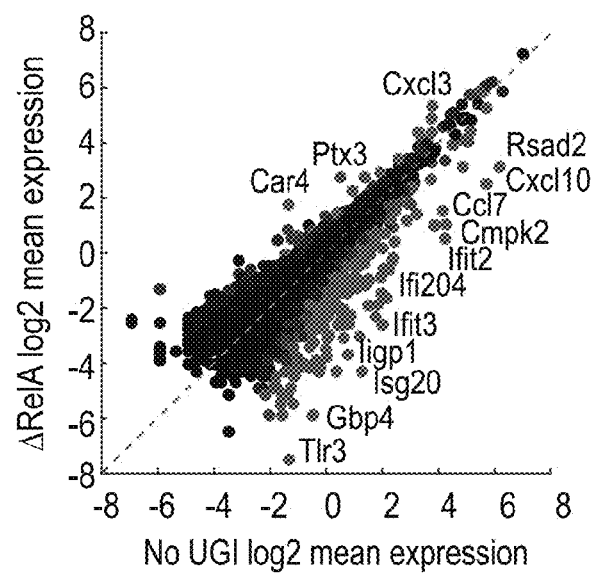
Figure 4G:
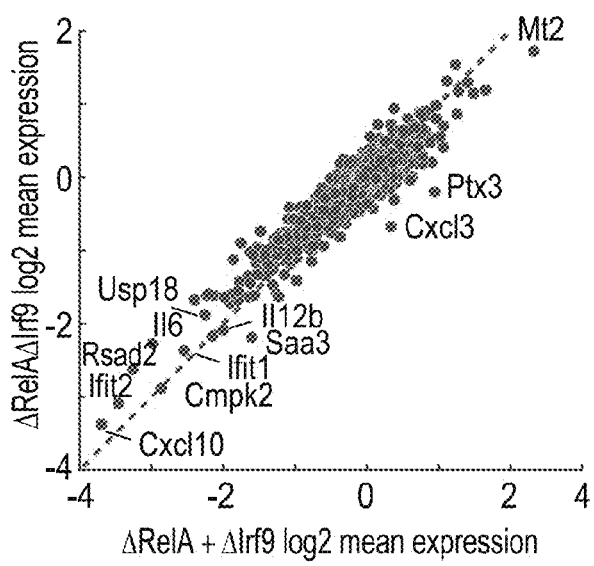
Figure 4H:
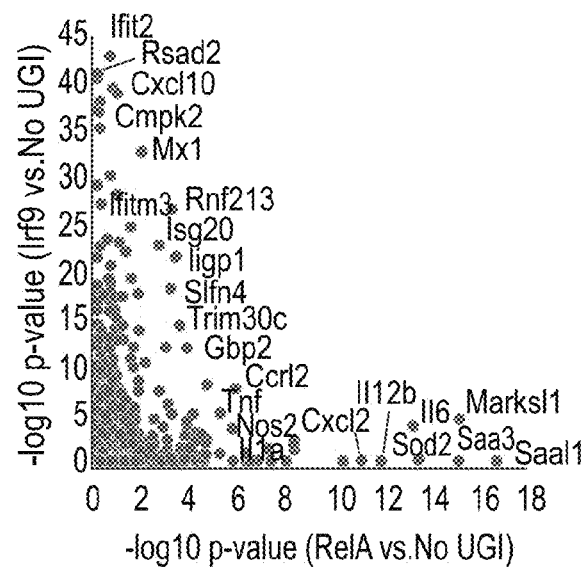

To evaluate the effect of monocytic cells perturbed for multiplexed inflammatory and antiviral pathways, the present inventors infected bone marrow cultures with a pool of gRNAs targeting Rela and Irf9, known regulators of the two pathways, respectively. Then, they stimulated the culture with LPS for 4 hours and sorted cells (GFP$^+$CD11c$^+$) for CRISP-seq analysis (FIGS. 4B-D). PhenoGraph clustering identified 691 monocytes and 81 DC cells (FIG. 10A). Because the DC populations are minor in this culture without Cebpb perturbation, the present inventors analytically removed all DC cells from further analysis. Projecting the kNN graph after label refinement revealed four distinct genotype compartments corresponding to cells with empty UGI, cells enriched for RelA KO, cells enriched for Irf9 KO and cells enriched for RelA and Irf9 double KO (FIGS. 4B and 10A-C). The cells enriched for Irf9 KO displayed a diminished antiviral response, including Ifit2 and Cxcl10, significantly downregulated (FIGS. 4C-D, 4F and 10D). In contrast, the cells enriched for RelA KO displayed a diminished inflammatory response, including Il12b and Cxcl2, significantly downregulated (FIGS. 4C-E and 10D). These results were confirmed by infecting separate cultures with single gRNA targeting Rela or Irf9, and comparable phenotypes and distributions to the CRISP-seq pool were obtained (FIGS. 10E-F). The combination of RelA and Irf9 KO had in most cases an additive effect (A+B=C; FIGS. 4D, 4G-H and 10D), indicating that in monocytes, the inflammatory and antiviral pathways largely regulate different gene modules (Medzhitov, 2007; Napolitani et al., 2005). Among the few exceptions were Ptx3 and Cxcl3, a chemokine that controls monocyte migration. Cxcl3 displayed interesting combinatorics, as it was repressed by IRF9 and activated by RelA, suggesting that this chemokine may have opposing effects upon different perturbations. Together, these results demonstrate the ability of CRISP-seq to analyze at the single-cell resolution multiplexed perturbations and non-overlapping regulation of inflammatory and antiviral responses in monocytes.

Example 4

Perturbations of Developmental and Signaling-Dependent TFs Reveal the Rewiring of Regulatory Circuits in Myeloid Cells In order to extend the analysis to a larger group of TFs regulating the inflammatory and antiviral circuits as well as probe for the role of these pathways in other cell types, the present inventors infected bone marrow cells with mixtures of Cebpb, Irf9, Irf8, Irf4, Stat1, Stat2, Rela and Nfkb1 gRNAs, and performed CRISP-seq on 6749 cells. Clustering analysis identified similar cell states as in previous perturbations, including two DC states enriched for Cebpb, and monocyte cells that are perturbed in the antiviral response module (Stat1, Stat2, Irf8 and Irf9) and in the inflammatory module (Rela and Nfkb1) (FIGS. 5A-C and 11A-C). The monocytic cells perturbed for the antiviral regulators displayed a diminished antiviral response (e.g. Ifit2, Cxcl10) and regulatory factors (Irf7, Stat2), with almost no effect on the inflammatory gene module (FIGS. 5A-C and 11A-C). In contrast, the cells perturbed for inflammatory regulators displayed a diminished inflammatory response (Cxcl2, Il12b). In order to determine if these effects are direct or indirect, the present inventors compared the binding pattern of STAT1, STAT2 and RelA in monocytes to the transcriptional change upon perturbation of each factor (FIG. 5D-E; (Garber et al., 2012)). Most genes that were downregulated in Stat1/2 knockouts were also bound directly by these factors (Pearson correlation r=0.52), specifically within enhancer regions, suggesting that many of the transcriptional effects for these factors are direct.

Figure 5E:
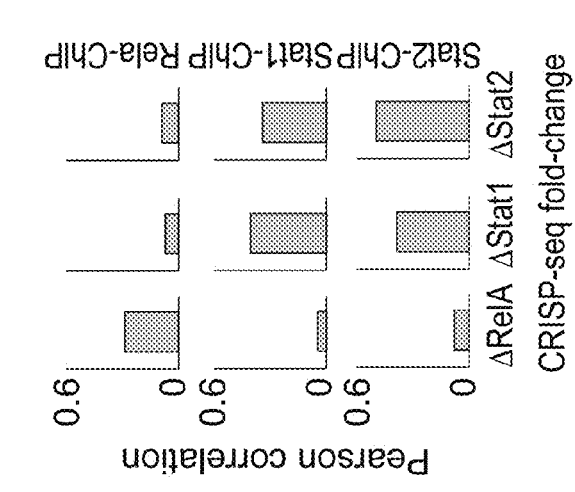
Figure 5D:
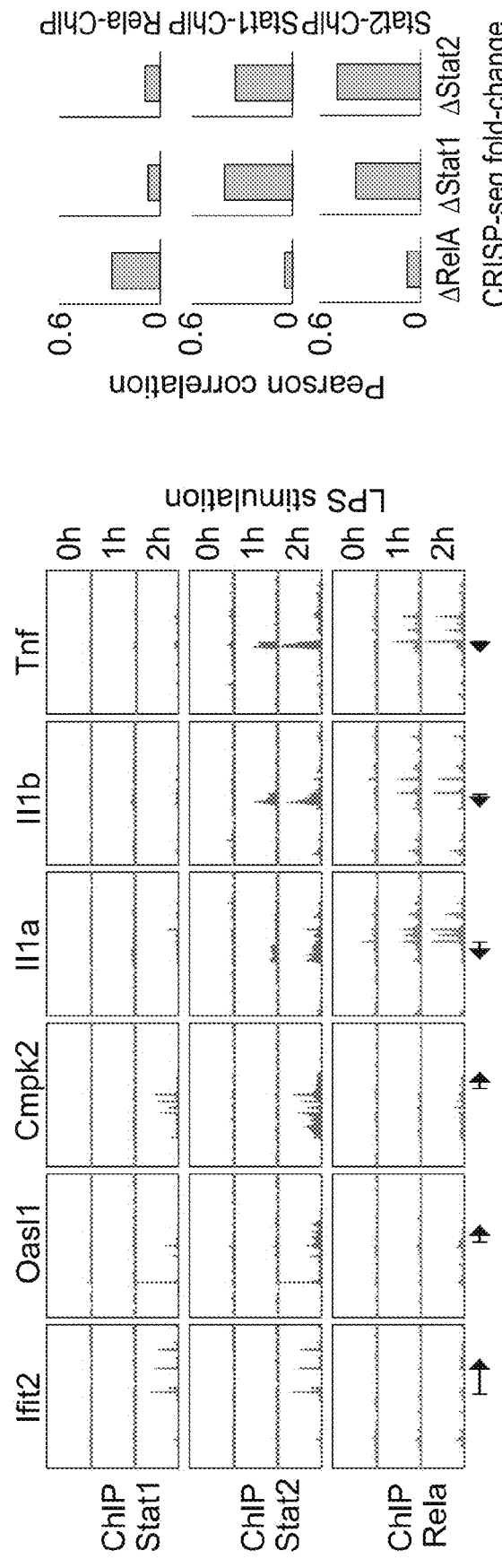
Figure 5F:
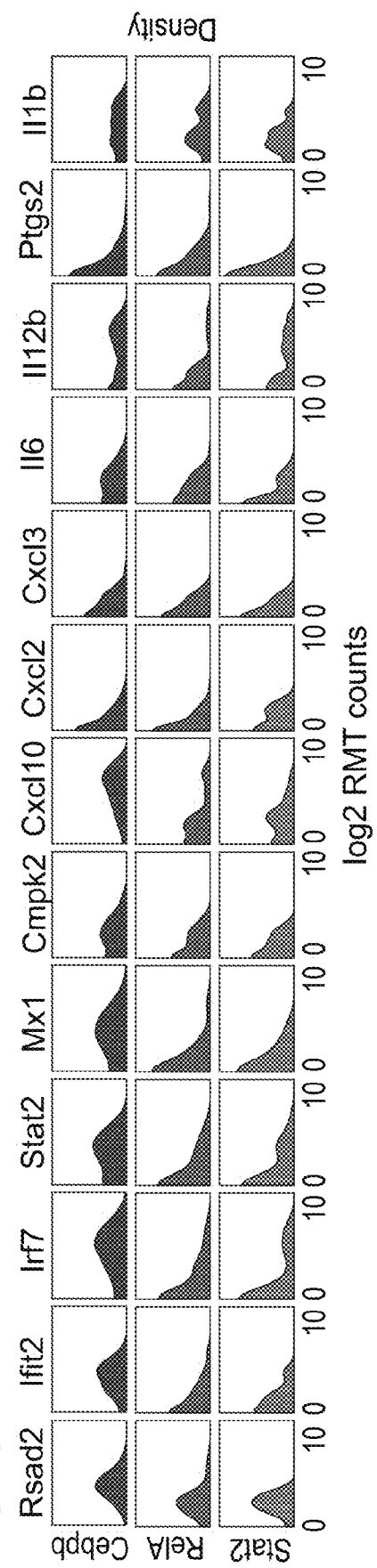

The present inventors next addressed the rewiring of the same inflammatory and antiviral circuits in other myeloid cell types. They analyzed only factors perturbed in more than 30 cells, namely Rela and Stat2. Knockout of Stat2 in DC mimicked to a large degree the effects observed in monocytes, namely perturbation of a large set of antiviral genes (FIGS. 5F and 11C), of DC-specific response genes such as the migratory chemokine Ccr7, as well as of co-stimulatory molecules (CD83 and CD86). Since the inflammatory genes are not upregulated in DCs, the present inventors did not expect a specific effect of RelA KO in these cells. Surprisingly, RelA was found to affect a large number of activated DC genes (Ouaaz et al., 2002). These included co-stimulatory molecules, chemokines and antiviral response genes (FIGS. 5F and 11C). Together, our analyses suggest that inflammatory and antiviral response circuits are rewired in different myeloid cells, and that specific regulators control different gene modules in a cell type-specific manner.

Example 5

Figure 12A:
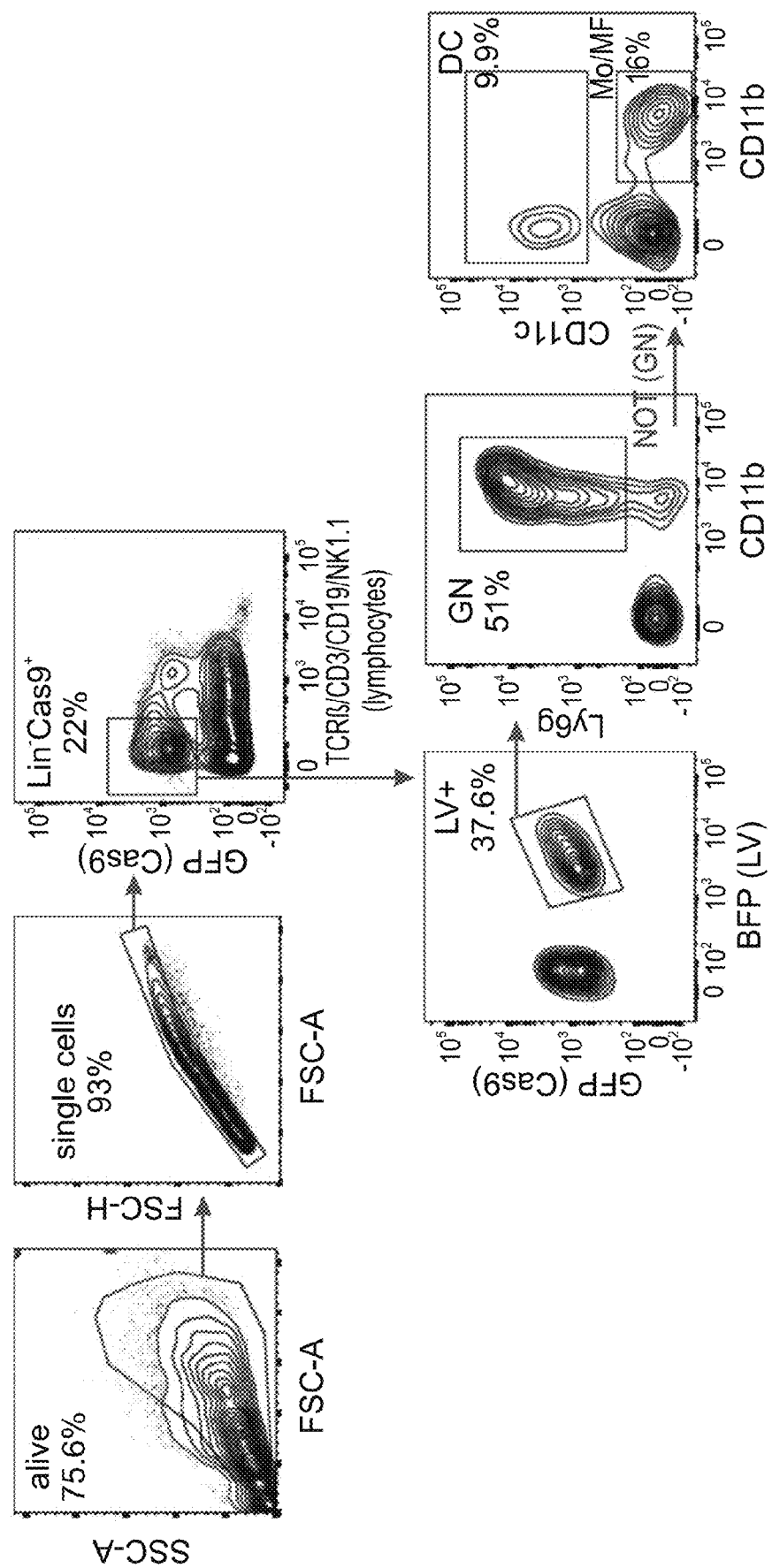

In Vivo CRISP-Seq Analysis Uncover the Complexity of Myeloid Regulatory Circuits in Immune Niches In vitro models identify many aspects of gene regulation and cellular function, but do not recapitulate the full complexity of physiological interactions of diverse cell types within specific tissues (Chen et al., 2015). Immune niches within the spleen, lymph node, brain or tumor represent a highly complex and dynamic network of interactions of various immune and non-immune cell types. Understanding the precise function of different regulatory circuits in these niches is important for both basic and clinical research. To study the regulatory function of developmental and signaling-dependent factors in immune niches, Lin− Sca1+ c-kit+ (LSK) hematopoietic progenitors were sorted from GFP-labeled Cas9 knockin mice, and infected with a pool of Cebpb, Irf8, Rela, Stat1, Stat2, and two control gRNAs (FIG. 6A). Cas9-GFP+ donor populations were mixed with unlabeled wild-type supportive bone marrow cells and injected into lethally irradiated recipient mice (FIG. 6A). Seven days following transplantation, successful engraftment was observed and mice were injected with LPS (FIG. 12A).

Figure 6D:
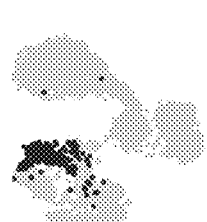
Figure 6D:
Figure 6D:
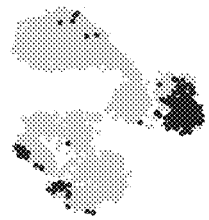
Figure 6D:
Figure 12B:
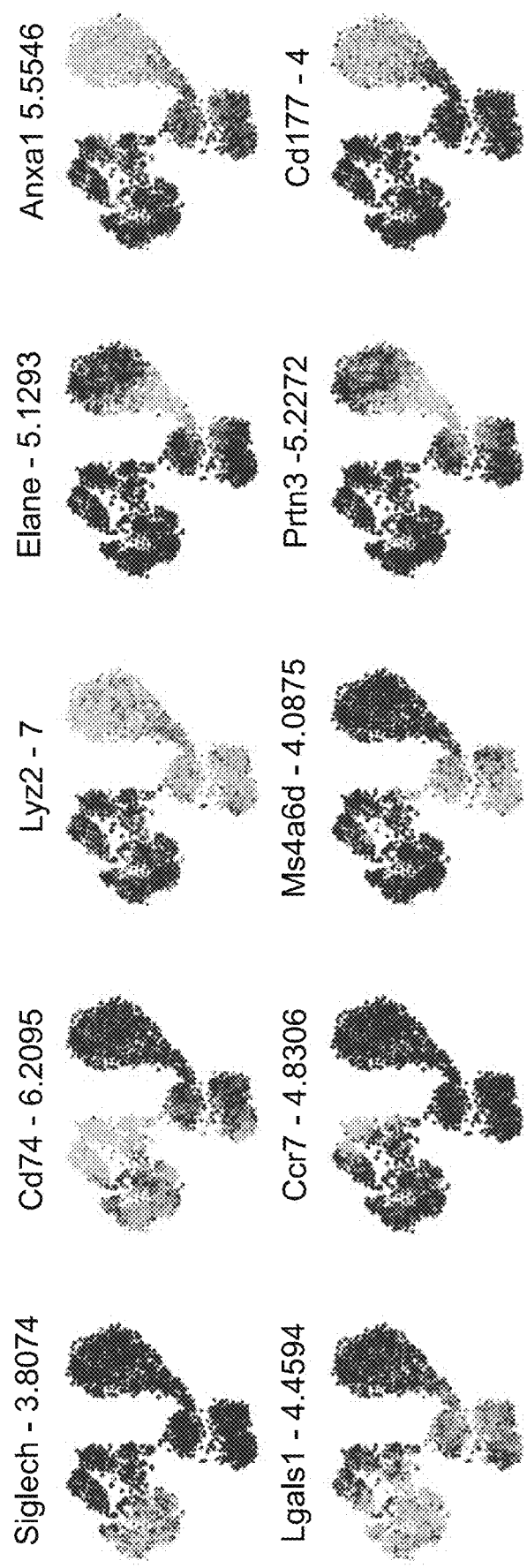

To focus on the regulation of myeloid cell response to pathogens in the splenic niche, four hours following LPS stimulation 2768 splenic myeloid cells (CD11b$^+$ or CD11c$^+$) positive for GFP and BFP were sorted for CRISP-seq analysis. Unsupervised analysis of the single myeloid cells identified nine myeloid cell types and states (FIGS. 6B and 12B), including granulocytes, monocytes, conventional DCs (cDCs) and plasmacytoid DCs (pDCs). Similar to the in vitro model, monocytes were associated with high expression levels of antibacterial enzymes (Ctsc and Lyz2) and of the Cebpb transcription factor (FIGS. 6B-C and 12B). Conventional DCs were associated with high levels of MHC-II pathway genes and cysteine protease inhibitors (H2-Eb1 and Cst3), whereas pDCs were associated with expression of classical markers of this type, such as Ly6D and Siglech, and relevant TFs (Irf8 and Tcf4). Granulocytes were associated with two clusters; an immature state expressing enzymes associated with neutrophil granule formation, namely MPO and Elane, and a more mature state expressing high levels of the antimicrobial peptide CAMP (FIGS. 6B-C and 12B). Projecting the perturbation indexes (genotype) on this graph showed that perturbation of Cebpb is linked to generation of cDCs ($p<10^{-8}$), similar to the in vitro model, whereas perturbation of Irf8 is associated with granulopoiesis ($p<10^{-12}$) (FIG. 6D and FIGS. 12A-F). To confirm the link between Irf8 KO and increased granulopoiesis, bone marrow cells were infected in vitro with mixtures of Cebpb, Irf8, and control gRNA, and sorted both CD11c+ and CD11c− cells for CRISP-seq analysis. Similar to the in vivo model, Cebpb was shown to is essential for the monocytic state, whereas Irf8 is essential for the DC and monocyte state (FIGS. 12D-E). These results are in agreement with knockout experiments showing that Irf8 is required for the development of pDCs, cDCs, monocytes and macrophages, while it inhibits the generation of neutrophils (Becker et al., 2012; Kurotaki and Tamura, 2016).

Figure 6E:
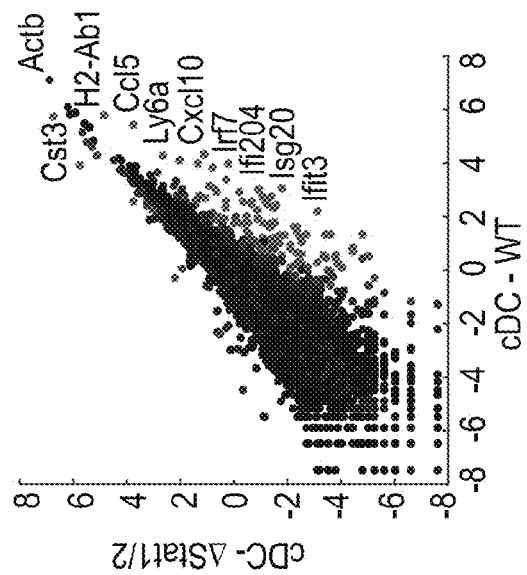
Figure 6E:
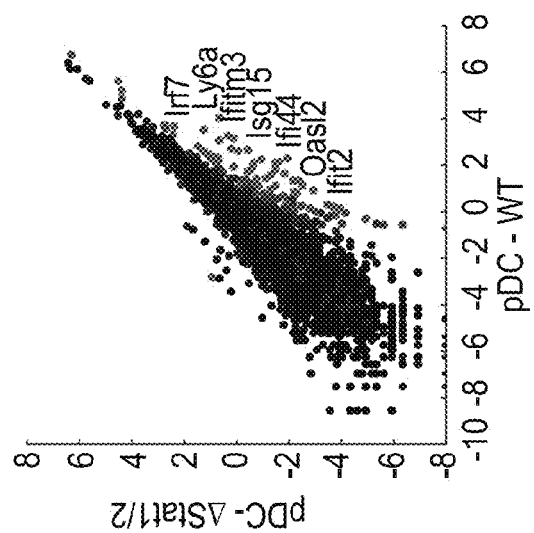
Figure 6E:
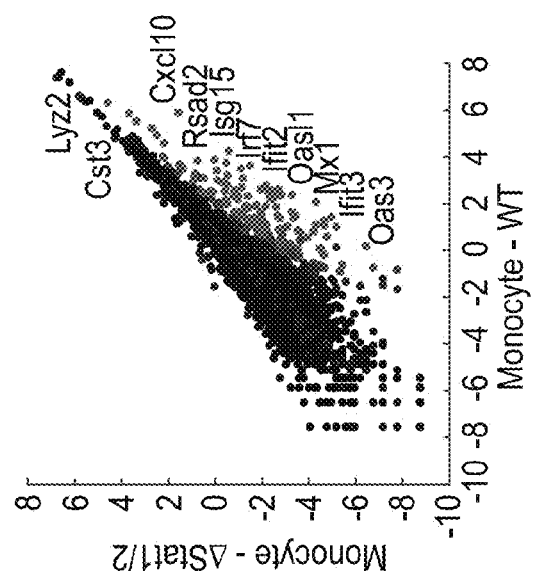
Figure 6F:
Figure 6F:
Figure 6F:
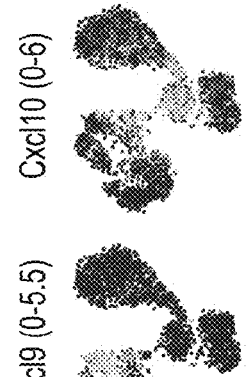
Figure 6F:
Figure 6F:
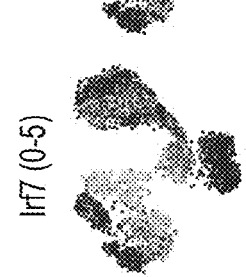
Figure 6F:
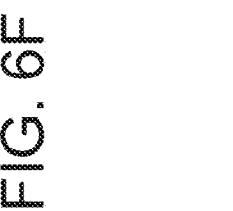
Figure 12C:
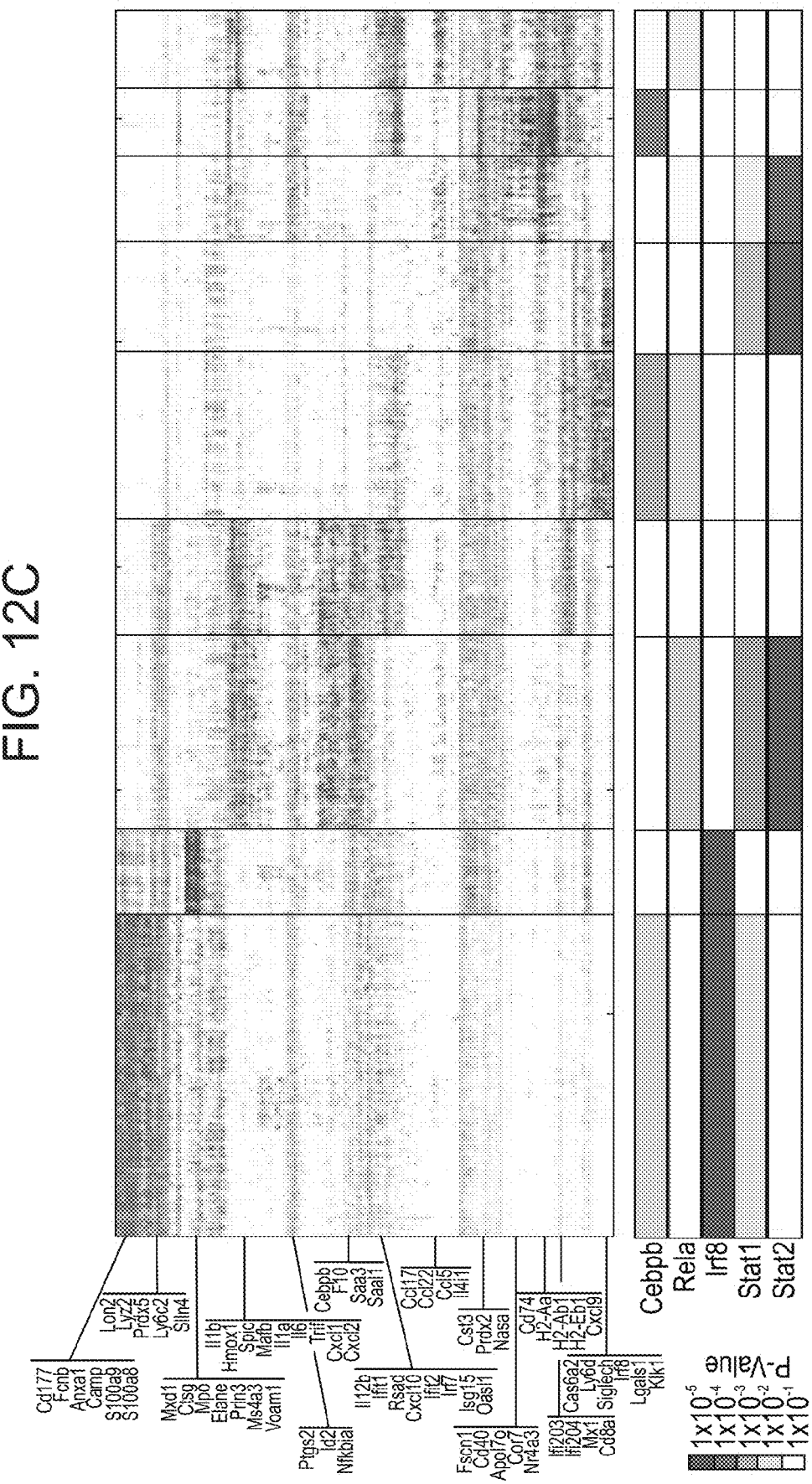
Figures 12D, 12E, 12F:
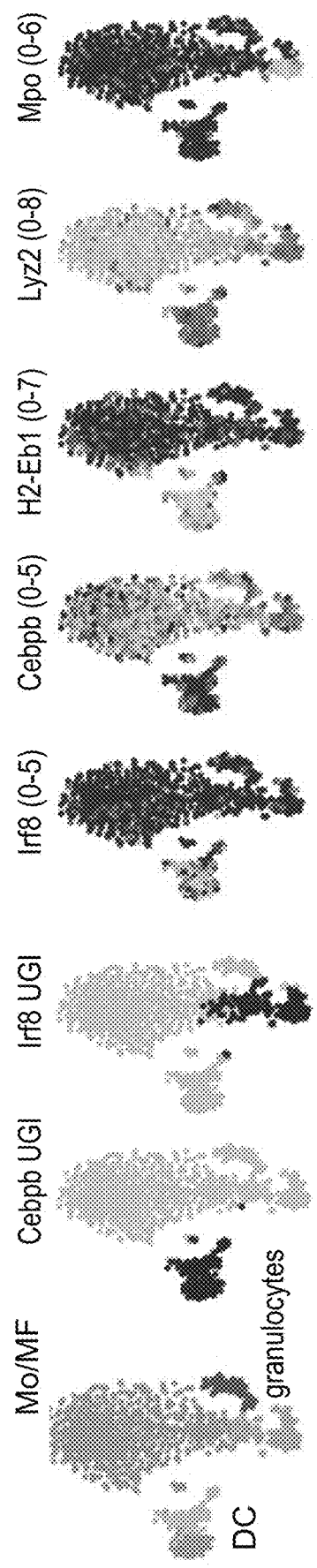

Focusing on the perturbations of Stat1 or Stat2 resulted in largely overlapping phenotypes enriched for different activation states of monocytes, pDCs and cDCs (FIGS. 6D-F and 12C). Comparison of Stat1/2-perturbed versus wild-type cells within and across cell types revealed Stat1/2-dependent antiviral genes that were either common to various myeloid cell types (e.g., Irf7 and Isg15) or associated with specific cell types (Cxcl10, Ifi204 and Ifi27l2b) (FIGS. 6E and 12C). Together, these data show that the CRISP-seq technology is a powerful tool to elucidate the function of genes and pathways within various cell types in specific immune niches. In the future, CRISP-seq analysis of a larger set of developmental and signaling-dependent factors, in combination with different environmental and small molecule conditions, will enable engineering of immune cells towards desired responses within specific niches, including for improved immunotherapy.

Discussion

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An expression construct comprising:
    (i) a DNA sequence which encodes at least one guide RNA (gRNA) operatively linked to a first promoter sequence so as to allow expression of said gRNA in a target cell; and
    (ii) a barcode sequence being between 6-10 nucleotides for identification of said at least one gRNA, said barcode sequence being operatively linked to a second promoter sequence so as to allow expression of said barcode sequence in said target cell wherein said first promoter sequence is distinct from said second promoter sequence.

2. The expression construct of claim 1, further comprising a DNA sequence which encodes a detectable or selectable moiety.

3. The expression construct of claim 1, comprising a plurality of gRNAs and a plurality of barcodes, wherein the expression construct comprises the same number of barcodes as there are encoded gRNAs.

4. The expression construct of claim 1, wherein said barcode sequence is positioned 3' to said DNA encoding said gRNA.

5. The expression construct of claim 1, further comprising a polyadenylation signal which is between 300-500 base pairs downstream of said barcode sequence.

6. The expression construct of claim 5, being a viral expression construct.

7. A kit comprising:
    (i) the expression construct of claim 1; and
    (ii) an expression construct which comprises DNA encoding a CRISPR endonuclease.

8. The kit of claim 7, wherein said expression construct which comprises DNA encoding said CRISPR endonuclease further comprises DNA encoding a detectable or selectable moiety.

9. The expression construct of claim 1, further comprising a DNA sequence which encodes a CRISPR endonuclease.

10. An expression construct comprising:
    (i) a DNA sequence which encodes a plurality of gRNAs;
    (ii) a plurality of barcode sequences being between 6-10 nucleotides for identification of each of said gRNAs, wherein the number of barcode sequences is identical to the number of gRNAs; and
    (iii) at least one promoter sequence operatively linked to said DNA sequence and said barcode sequences so as to allow expression of said gRNAs and said barcode sequences.

* * * * *

SEQUENCE LISTING

<160> NUMBER OF SEQ ID NOS: 17

<210> SEQ ID NO 1
<211> LENGTH: 64
<212> TYPE: DNA

```
<213> ORGANISM: Artificial sequence
<220> FEATURE:
<223> OTHER INFORMATION: Single strand DNA oligonucleotide
<220> FEATURE:
<221> NAME/KEY: misc_feature
<222> LOCATION: (36)..(43)
<223> OTHER INFORMATION: n is a, c, g, or t

<400> SEQUENCE: 1
ctccctttgg gccgcctccc cgcgtcgacg gatccnnnnn nnngacttac aaggcagctg    60
taga                                                                64

<210> SEQ ID NO 2
<211> LENGTH: 20
<212> TYPE: DNA
<213> ORGANISM: Artificial sequence
<220> FEATURE:
<223> OTHER INFORMATION: UGI ligation adapter
<220> FEATURE:
<221> NAME/KEY: misc_feature
<222> LOCATION: (1)..(1)
<223> OTHER INFORMATION: 5' Phosphate
<220> FEATURE:
<221> NAME/KEY: misc_feature
<222> LOCATION: (20)..(20)
<223> OTHER INFORMATION: 3'  C3 spacer (blocker)

<400> SEQUENCE: 2
atgatcaagc gaccaccgag                                               20

<210> SEQ ID NO 3
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 3
ctcggtggtc gcttgatcat                                               20

<210> SEQ ID NO 4
<211> LENGTH: 49
<212> TYPE: DNA
<213> ORGANISM: Artificial sequence
<220> FEATURE:
<223> OTHER INFORMATION: Single strand DNA oligonucleotide
<220> FEATURE:
<221> NAME/KEY: misc_feature
<222> LOCATION: (23)..(31)
<223> OTHER INFORMATION: n is a, c, g, or t

<400> SEQUENCE: 4
ctacacgacg ctcttccgat ctnnnnnnnn ntccccgcgt cgacggatc               49

<210> SEQ ID NO 5
<211> LENGTH: 58
<212> TYPE: DNA
<213> ORGANISM: Artificial sequence
<220> FEATURE:
<223> OTHER INFORMATION: Single strand DNA oligonucleotide

<400> SEQUENCE: 5
caagcagaag acggcatacg agatgtgact ggagttcaga cgtgtgctct tccgatct     58

<210> SEQ ID NO 6
<211> LENGTH: 19
<212> TYPE: DNA
<213> ORGANISM: Artificial sequence
```

```
<220> FEATURE:
<223> OTHER INFORMATION: Single strand DNA oligonucleotide

<400> SEQUENCE: 6
tccccgcgtc gacggatcc                                                    19

<210> SEQ ID NO 7
<211> LENGTH: 39
<212> TYPE: DNA
<213> ORGANISM: Artificial sequence
<220> FEATURE:
<223> OTHER INFORMATION: Single strand DNA oligonucleotide

<400> SEQUENCE: 7
acacgacgct cttccgatct cctggtagcc caggtaggc                              39

<210> SEQ ID NO 8
<211> LENGTH: 48
<212> TYPE: DNA
<213> ORGANISM: Artificial sequence
<220> FEATURE:
<223> OTHER INFORMATION: Single strand DNA oligonucleotide

<400> SEQUENCE: 8
ctggagttca gacgtgtgct cttccgatct tctccgacct cttcgccg                    48

<210> SEQ ID NO 9
<211> LENGTH: 40
<212> TYPE: DNA
<213> ORGANISM: Artificial sequence
<220> FEATURE:
<223> OTHER INFORMATION: Single strand DNA oligonucleotide

<400> SEQUENCE: 9
acacgacgct cttccgatct tgtctggtta acagcctttg                             40

<210> SEQ ID NO 10
<211> LENGTH: 50
<212> TYPE: DNA
<213> ORGANISM: Artificial sequence
<220> FEATURE:
<223> OTHER INFORMATION: Single strand DNA oligonucleotide

<400> SEQUENCE: 10
ctggagttca gacgtgtgct cttccgatct ccatttccca tcctaacttc                  50

<210> SEQ ID NO 11
<211> LENGTH: 58
<212> TYPE: DNA
<213> ORGANISM: Artificial sequence
<220> FEATURE:
<223> OTHER INFORMATION: Single strand DNA oligonucleotide

<400> SEQUENCE: 11
aatgatacgg cgaccaccga gatctacact ctttccctac acgacgctct tccgatct         58

<210> SEQ ID NO 12
<211> LENGTH: 55
<212> TYPE: DNA
<213> ORGANISM: Artificial sequence
<220> FEATURE:
<223> OTHER INFORMATION: Single strand DNA oligonucleotide
<220> FEATURE:
<221> NAME/KEY: misc_feature
<222> LOCATION: (25)..(31)
<223> OTHER INFORMATION: n is a, c, g, or t
```

-continued

<400> SEQUENCE: 12
caagcagaag acggcatacg agatnnnnnn ngtgactgga gttcagacgt gtgct    55

<210> SEQ ID NO 13
<211> LENGTH: 6
<212> TYPE: RNA
<213> ORGANISM: Artificial sequence
<220> FEATURE:
<223> OTHER INFORMATION: polyadenylation signal sequence

<400> SEQUENCE: 13 aauaaa    6

<210> SEQ ID NO 14
<211> LENGTH: 35
<212> TYPE: DNA
<213> ORGANISM: Artificial sequence
<220> FEATURE:
<223> OTHER INFORMATION: T7 RNA polymerase promoter sequence

<400> SEQUENCE: 14
cgattgaggc cggtaatacg actcactata ggggc    35

<210> SEQ ID NO 15
<211> LENGTH: 8444
<212> TYPE: DNA
<213> ORGANISM: Artificial sequence
<220> FEATURE:
<223> OTHER INFORMATION: Sequences of exemplary constructs with BFP

<400> SEQUENCE: 15
atcccctgat tctgtggata accgtattac cgcctttgag tgagctgata ccgctcgccg    60
cagccgaacg accgagcgca gcgagtcagt gagcgaggaa gcggaagagc gcccaatacg    120
caaaccgcct ctccccgcgc gttggccgat tcattaatgc agctggcacg acaggtttcc    180
cgactggaaa gcgggcagtg agcgcaacgc aattaatgtg agttagctca ctcattaggc    240
accccaggct ttacacttta tgcttccggc tcgtatgttg tgtggaattg tgagcggata    300
acaatttcac acaggaaaca gctatgacca tgattacgcc aagcgcgcaa ttaaccctca    360
ctaaagggaa caaaagctgg agctgcaagc ttaatgtagt cttatgcaat actcttgtag    420
tcttgcaaca tggtaacgat gagttagcaa catgccttac aaggagagaa aaagcaccgt    480
gcatgccgat tggtggaagt aaggtggtac gatcgtgcct tattaggaag gcaacagacg    540
ggtctgacat ggattggacg aaccactgaa ttgccgcatt gcagagatat tgtatttaag    600
tgcctagctc gatacataaa cgggtctctc tggttagacc agatctgagc ctgggagctc    660
tctggctaac tagggaaccc actgcttaag cctcaataaa gcttgccttg agtgcttcaa    720
gtagtgtgtg cccgtctgtt gtgtgactct ggtaactaga tccctcag acccttttag    780 tcagtgtgga aaatctctag cagtggcgcc cgaacaggga cttgaaagcg aaagggaaac    840
cagaggagct ctctcgacgc aggactcggc ttgctgaagc gcgcacggca agaggcgagg    900
ggcggcgact ggtgagtacg ccaaaaattt tgactagcgg aggctagaag gagagagatg    960
ggtgcgagag cgtcagtatt aagcggggga gaattagatc gcgatgggaa aaaattcggt    1020
taaggccagg gggaaagaaa aaatataaat taaaacatat agtatgggca agcagggagc    1080
tagaacgatt cgcagttaat cctggcctgt tagaaacatc agaaggctgt agacaaatac    1140
tgggacagct acaaccatcc cttcagacag gatcagaaga acttagatca ttatataata    1200
cagtagcaac cctctattgt gtgcatcaaa ggatagagat aaaagacacc aaggaagctt    1260

```
tagacaagat agaggaagag caaaacaaaa gtaagaccac cgcacagcaa gcggccgctg    1320
atcttcagac ctggaggagg agatatgagg gacaattgga gaagtgaatt atataaatat    1380
aaagtagtaa aaattgaacc attaggagta gcacccacca aggcaaagag aagagtggtg    1440
cagagagaaa aaagagcagt gggaatagga gctttgttcc ttgggttctt gggagcagca    1500
ggaagcacta tgggcgcagc gtcaatgacg ctgacggtac aggccagaca attattgtct    1560
ggtatagtgc agcagcagaa caatttgctg agggctattg aggcgcaaca gcatctgttg    1620
caactcacag tctggggcat caagcagctc caggcaagaa tcctggctgt ggaaagatac    1680
ctaaaggatc aacagctcct ggggatttgg ggttgctctg gaaaactcat ttgcaccact    1740
gctgtgcctt ggaatgctag ttggagtaat aaatctctgg aacagatttg gaatcacacg    1800
acctggatgg agtgggacag agaaattaac aattacacaa gcttaataca ctccttaatt    1860
gaagaatcgc aaaaccagca agaaaagaat gaacaagaat tattggaatt agataaatgg    1920
gcaagtttgt ggaattggtt taacataaca aattggctgt ggtatataaa attattcata    1980
atgatagtag gaggcttggt aggtttaaga atagtttttg ctgtactttc tatagtgaat    2040
agagttaggc agggatattc accattatcg tttcagaccc acctcccaac cccgagggga    2100
cccagagagg gcctatttcc catgattcct tcatatttgc atatacgata caaggctgtt    2160
agagagataa ttagaattaa tttgactgta aacacaaaga tattagtaca aatacgtga    2220 cgtagaaagt aataatttct tgggtagttt gcagttttaa aattatgttt taaaatggac    2280
tatcatatgc ttaccgtaac ttgaaagtat ttcgatttct tggctttata tcttgtgg     2340 aaaggacgaa acaccggaga cggacgtctc tgttttagag ctagaaatag caagttaaaa    2400
taaggctagt ccgttatcaa cttgaaaaag tggcaccgag tcggtgcttt tttaagcttg    2460
gcgtaactag atcttgagac aaatggcagt attcatccac aattttaaaa gaaaaggggg    2520
gattgggggg tacagtgcag gggaaagaat agtagacata atagcaacag acatacaaac    2580
taaagaatta caaaaacaaa ttacaaaaat tcaaaatttt cgggtttatt acagggacag    2640
cagagatcca ctttggcgcc ggctcgaggg ggcccgggtg caaagatgga taaagtttta    2700
aacagagagg aatctttgca gctaatggac cttctaggtc ttgaaaggag tgggaattgg    2760
ctccggtgcc cgtcagtggg cagagcgcac atcgcccaca gtccccgaga agttgggggg    2820
aggggtcggc aattgatccg gtgcctagag aaggtggcgc ggggtaaact gggaaagtga    2880
tgtcgtgtac tggctccgcc ttttttccga gggtggggga gaaccgtata taagtgcagt    2940
agtcgccgtg aacgttcttt ttcgcaacgg gtttgccgcc agaacacagg taagtgccgt    3000
gtgtggttcc cgcgggcctg gcctctttac gggttatggc ccttgcgtgc cttgaattac    3060
ttccactggc tgcagtacgt gattcttgat cccgagcttc gggttggaag tgggtgggag    3120
agttcgaggc cttgcgctta aggagcccct tcgcctcgtg cttgagttga ggcctggcct    3180
gggcgctggg gccgccgcgt gcgaatctgg tggcaccttc gcgcctgtct cgctgctttc    3240
gataagtctc tagccattta aaattttga tgacctgctg cgacgctttt tttctggcaa    3300
gatagtcttg taaatgcggg ccaagatctg cacactggta tttcggtttt tggggccgcg    3360
ggcggcgacg gggcccgtgc gtcccagcgc acatgttcgg cgaggcgggg cctgcgagcg    3420
cggccaccga gaatcggacg ggggtagtct caagctggcc ggcctgctct ggtgcctggc    3480
ctcgcgccgc cgtgtatcgc cccgccctgg gcggcaaggc tggcccggtc ggcaccagtt    3540
gcgtgagcgg aaagatggcc gcttcccggc cctgctgcag ggagctcaaa atggaggacg    3600
```

```
cggcgctcgg gagagcgggc gggtgagtca cccacacaaa ggaaaagggc ctttccgtcc    3660
tcagccgtcg cttcatgtga ctccacggag taccgggcgc cgtccaggca cctcgattag    3720
ttctcgagct tttggagtac gtcgtctttaggttgggggg aggggtttta tgcgatggag    3780
tttccccaca ctgagtgggt ggagactgaa gttaggccag cttggcactt gatgtaattc    3840
tccttggaat ttgccctttt tgagtttgga tcttggttca ttctcaagcc tcagacagtg    3900
gttcaaagtt ttttcttcc atttcaggtg tcgtgacgta cggccaccat ggtgagcaag    3960
ggcgaggagc tgttcaccgg ggtggtgccc atcctggtcg agctggacgg cgacgtaaac    4020
ggccacaagt tcagcgtgag gggcgagggc gagggcgatg ccaccaacgg caagctgacc    4080
ctgaagttca tctgcaccac cggcaagctg cccgtgccct ggcccaccct cgtgaccacc    4140
ctgagccacg gcgtgcagtg cttcgcccgc taccccgacc acatgaagca gcacgacttc    4200
ttcaagtccg ccatgcccga aggctacgtc caggagcgca ccatcttctt caaggacgac    4260
ggcacctaca agacccgcgc cgaggtgaag ttcgagggcg acaccctggt gaaccgcatc    4320
gagctgaagg gcgtcgactt caaggaggac ggcaacatcc tggggcacaa gctggagtac    4380
aacttcaaca gccacaacat ctatatcatg gccgtcaagc agaagaacgg catcaaggtg    4440
aacttcaaga tccgccacaa cgtggaggac ggcagcgtgc agctcgccga ccactaccag    4500
cagaacaccc ccatcggcga cggccccgtg ctgctgcccg acagccacta cctgagcacc    4560
cagtccgtgc tgagcaaaga cccccaacgag aagcgcgatc acatggtcct gctggagttc    4620
cgcaccgccg ccgggatcac tctcggcatg gacgagctgt acaagtaaac gcgttaagtc    4680
gagtcgacaa tcaacctctg gattacaaaa tttgtgaaag attgactggt attcttaact    4740
atgttgctcc ttttacgcta tgtggatacg ctgctttaat gcctttgtat catgctattg    4800
cttcccgtat ggctttcatt ttctcctcct tgtataaatc ctggttgctg tctctttatg    4860
aggagttgtg gcccgttgtc aggcaacgtg gcgtggtgtg cactgtgttt gctgacgcaa    4920
cccccactgg ttggggcatt gccaccacct gtcagctcct ttccgggact ttcgctttcc    4980
ccctccctat tgccacggcg gaactcatcg ccgcctgcct tgcccgctgc tggacagggg    5040
ctcggctgtt gggcactgac aattccgtgg tgttgtcggg gaaatcatcg tcctttcctt    5100
ggctgctcgc ctgtgttgcc acctggattc tgcgcgggac gtccttctgc tacgtcccct    5160
cggccctcaa tccagcggac cttccttccc gcggcctgct gccggctctg cggcctcttc    5220
cgcgtcttcg ccttcgccct cagacgagtc ggatctccct ttgggccgcc tccccgcgtc    5280
gacggatccg gtgatgggac ttacaaggca gctgtagatc ttagccactt tttaaaagaa    5340
aaggggggac tggaagggct aattcactcc caacgaagac aagatctgct ttttgcttgt    5400
actgggtctc tctggttaga ccagatctga gcctgggagc tctctggcta actagggaac    5460
ccactgctta agcctcaata aagcttgcct tgagtgcttc aagtagtgtg tgcccgtctg    5520
ttgtgtgact ctggtaacta gagatccctc agacccttttagtcagtgtg gaaaatctct    5580 agcagtacgt atagtagttc atgtcatctt attattcagt atttataact tgcaaagaaa    5640
tgaatatcag agagtgagag gaacttgttt attgcagctt ataatggtta caaataaagc    5700
aatagcatca caaatttcac aaataaagca tttttttcac tgcattctag ttgtggtttg    5760
tccaaactca tcaatgtatc ttatcatgtc tggctctagc tatcccgccc ctaactccgc    5820
ccatcccgcc cctaactccg cccagttccg cccattctcc gccccatggc tgactaattt    5880
tttttattta tgcagaggcc gaggccgcct cggcctctga gctattccag aagtagtgag    5940
gaggcttttt tggaggccta gggacgtacc caattcgccc tatagtgagt cgtattacgc    6000
```

```
gcgctcactg gccgtcgttt tacaacgtcg tgactgggaa aaccctggcg ttacccaact    6060
taatcgcctt gcagcacatc cccctttcgc cagctggcgt aatagcgaag aggcccgcac    6120
cgatcgccct tcccaacagt tgcgcagcct gaatggcgaa tgggacgcgc cctgtagcgg    6180
cgcattaagc gcggcgggtg tggtggttac gcgcagcgtg accgctacac ttgccagcgc    6240
cctagcgccc gctcctttcg ctttcttccc ttcctttctc gccacgttcg ccggctttcc    6300
ccgtcaagct ctaaatcggg gctcccttt  agggttccga tttagtgctt tacggcacct    6360
cgaccccaaa aaacttgatt agggtgatgg ttcacgtagt gggccatcgc cctgatagac    6420
ggttttttcgc cctttgacgt tggagtccac gttctttaat agtggactct tgttccaaac    6480
tggaacaaca ctcaacccta tctcggtcta ttcttttgat ttataaggga ttttgccgat    6540
ttcggcctat tggttaaaaa atgagctgat ttaacaaaaa tttaacgcga attttaacaa    6600
aatattaacg cttacaattt aggtggcact tttcggggaa atgtgcgcgg aacccctatt    6660
tgtttatttt tctaaataca ttcaaatatg tatccgctca tgagacaata accctgataa    6720
atgcttcaat aatattgaaa aaggaagagt atgagtattc aacatttccg tgtcgccctt    6780
attccctttt ttgcggcatt ttgccttcct gttttgctc  acccagaaac gctggtgaaa    6840
gtaaaagatg ctgaagatca gttgggtgca cgagtgggtt acatcgaact ggatctcaac    6900
agcggtaaga tccttgagag ttttcgcccc gaagaacgtt ttccaatgat gagcactttt    6960
aaagttctgc tatgtggcgc ggtattatcc cgtattgacg ccgggcaaga gcaactcggt    7020
cgccgcatac actattctca gaatgacttg gttgagtact caccagtcac agaaaagcat    7080
cttacggatg gcatgacagt aagagaatta tgcagtgctg ccataaccat gagtgataac    7140
actgcggcca acttacttct gacaacgatc ggaggaccga aggagctaac cgcttttttg    7200
cacaacatgg gggatcatgt aactcgcctt gatcgttggg aaccggagct gaatgaagcc    7260
ataccaaacg acgagcgtga caccacgatg cctgtagcaa tggcaacaac gttgcgcaaa    7320
ctattaactg gcgaactact tactctagct tcccggcaac aattaataga ctggatggag    7380
gcggataaag ttgcaggacc acttctgcgc tcggcccttc cggctggctg gtttattgct    7440
gataaatctg gagccggtga gcgtgggtct cgcggtatca ttgcagcact ggggccagat    7500
ggtaagccct cccgtatcgt agttatctac acgacgggga gtcaggcaac tatggatgaa    7560
cgaaatagac agatcgctga gataggtgcc tcactgatta agcattggta actgtcagac    7620
caagtttact catatatact ttagattgat ttaaaacttc attttttaatt taaaaggatc    7680
taggtgaaga tccttttttga taatctcatg accaaaatcc cttaacgtga gttttcgttc    7740
cactgagcgt cagaccccgt agaaaagatc aaaggatctt cttgagatcc ttttttttctg    7800
cgcgtaatct gctgcttgca aacaaaaaaa ccaccgctac cagcggtggt ttgtttgccg    7860
gatcaagagc taccaactct ttttccgaag gtaactggct tcagcagagc gcagatacca    7920
aatactgttc ttctagtgta gccgtagtta ggccaccact tcaagaactc tgtagcaccg    7980
cctacatacc tcgctctgct aatcctgtta ccagtggctg ctgccagtgg cgataagtcg    8040
tgtcttaccg ggttggactc aagacgatag ttaccggata aggcgcagcg gtcgggctga    8100
acggggggtt cgtgcacaca gcccagcttg gagcgaacga cctacaccga actgagatac    8160
ctacagcgtg agctatgaga aagcgccacg cttcccgaag ggagaaaggc ggacaggtat    8220
ccggtaagcg gcagggtcgg aacaggagag cgcacgaggg agcttccagg gggaaacgcc    8280
tggtatcttt atagtcctgt cgggtttcgc cacctctgac ttgagcgtcg attttttgtga    8340
```

```
tgctcgtcag ggggcggag cctatggaaa aacgccagca acgcggcctt tttacggttc    8400 ctggccttt gctggccttt tgctcacatg ttctttcctg cgtt                     8444

<210> SEQ ID NO 16
<211> LENGTH: 8384
<212> TYPE: DNA
<213> ORGANISM: Artificial sequence
<220> FEATURE:
<223> OTHER INFORMATION: Sequences of exemplary constructs with BFP

<400> SEQUENCE: 16
atcccctgat tctgtggata accgtattac cgcctttgag tgagctgata ccgctcgccg     60
cagccgaacg accgagcgca gcgagtcagt gagcgaggaa gcggaagagc gcccaatacg    120
caaaccgcct ctccccgcgc gttggccgat tcattaatgc agctggcacg acaggtttcc    180
cgactggaaa gcgggcagtg agcgcaacgc aattaatgtg agttagctca ctcattaggc    240
accccaggct ttacacttta tgcttccggc tcgtatgttg tgtggaattg tgagcggata    300
acaatttcac acaggaaaca gctatgacca tgattacgcc aagcgcgcaa ttaaccctca    360
ctaaagggaa caaaagctgg agctgcaagc ttaatgtagt cttatgcaat actcttgtag    420
tcttgcaaca tggtaacgat gagttagcaa catgccttac aaggagagaa aaagcaccgt    480
gcatgccgat tggtggaagt aaggtggtac gatcgtgcct tattaggaag caacagacg     540 ggtctgacat ggattggacg aaccactgaa ttgccgcatt gcagagatat tgtatttaag    600
tgcctagctc gatacataaa cgggtctctc tggttagacc agatctgagc ctgggagctc    660
tctggctaac tagggaaccc actgcttaag cctcaataaa gcttgccttg agtgcttcaa    720
gtagtgtgtg cccgtctgtt gtgtgactct ggtaactaga gatccctcag accctttag    780 tcagtgtgga aaatctctag cagtggcgcc cgaacaggga cttgaaagcg aaagggaaac    840
cagaggagct ctctcgacgc aggactcggc ttgctgaagc gcgcacggca agaggcgagg    900
ggcggcgact ggtgagtacg ccaaaaattt tgactagcgg aggctagaag agagagatg    960 ggtgcgagag cgtcagtatt aagcggggga gaattagatc gcgatgggaa aaaattcggt   1020
taaggccagg ggaaagaaa aaatataaat taaaacatat agtatgggca agcagggagc   1080
tagaacgatt cgcagttaat cctggcctgt tagaaacatc agaaggctgt agacaaatac   1140
tgggacagct acaaccatcc cttcagacag gatcagaaga acttagatca ttatataata   1200
cagtagcaac cctctattgt gtgcatcaaa ggatagagat aaaagacacc aaggaagctt   1260
tagacaagat agaggaagag caaaacaaaa gtaagaccac cgcacagcaa gcggccgctg   1320
atcttcagac ctggaggagg agatatgagg gacaattgga gaagtgaatt atataaatat   1380
aaagtagtaa aaattgaacc attaggagta gcacccacca aggcaaagag aagagtggtg   1440
cagagagaaa aaagagcagt gggaatagga gctttgttcc ttgggttctt gggagcagca   1500
ggaagcacta tgggcgcagc gtcaatgacg ctgacggtac aggccagaca attattgtct   1560
ggtatagtgc agcagcagaa caatttgctg agggctattg aggcgcaaca gcatctgttg   1620
caactcacag tctggggcat caagcagctc caggcaagaa tcctggctgt ggaaagatac   1680
ctaaaggatc aacagctcct ggggatttgg ggttgctctg gaaaactcat ttgcaccact   1740
gctgtgcctt ggaatgctag ttggagtaat aaatctctgg aacagatttg gaatcacacg   1800
acctggatgg agtgggacag agaaattaac aattacacaa gcttaataca ctccttaatt   1860
gaagaatcgc aaaaccagca agaaaagaat gaacaagaat tattggaatt agataaatgg   1920
gcaagtttgt ggaattggtt taacataaca aattggctgt ggtatataaa attattcata   1980
```

-continued

```
atgatagtag gaggcttggt aggtttaaga atagtttttg ctgtactttc tatagtgaat      2040
agagttaggc agggatattc accattatcg tttcagaccc acctcccaac cccgagggga      2100
cccagagagg gcctatttcc catgattcct tcatatttgc atatacgata caaggctgtt      2160
agagagataa ttagaattaa tttgactgta aacacaaaga tattagtaca aaatacgtga      2220
cgtagaaagt aataatttct tgggtagttt gcagttttaa aattatgttt taaaatggac      2280
tatcatatgc ttaccgtaac ttgaaagtat ttcgatttct tggctttata tatcttgtgg      2340
aaaggacgaa acaccggaga cggacgtctc tgttttagag ctagaaatag caagttaaaa      2400
taaggctagt ccgttatcaa cttgaaaaag tggcaccgag tcggtgcttt tttaagcttg      2460
gcgtaactag atcttgagac aaatggcagt attcatccac aattttaaaa gaaaaggggg      2520
gattgggggg tacagtgcag gggaaagaat agtagacata atagcaacag atatacaaac      2580
taaagaatta caaaaacaaa ttacaaaaat tcaaaatttt cgggtttatt acagggacag      2640
cagagatcca ctttggcgcc ggctcgaggg ggcccgggtg caaagatgga taaagtttta      2700
aacagagagg aatctttgca gctaatggac cttctaggtc ttgaaaggag tgggaattgg      2760
ctccggtgcc cgtcagtggg cagagcgcac atcgcccaca gtccccgaga agttgggggg      2820
aggggtcggc aattgatccg gtgcctagag aaggtggcgc ggggtaaact gggaaagtga      2880
tgtcgtgtac tggctccgcc ttttttcccga gggtggggga gaaccgtata taagtgcagt      2940
agtcgccgtg aacgttcttt ttcgcaacgg gtttgccgcc agaacacagg taagtgccgt      3000
gtgtggttcc cgcggggcctg gcctctttac gggttatggc ccttgcgtgc cttgaattac      3060
ttccactggc tgcagtacgt gattcttgat cccgagcttc gggttggaag tgggtgggag      3120
agttcgaggc cttgcgctta aggagcccct tcgcctcgtg cttgagttga ggcctggcct      3180
gggcgctggg gccgccgcgt gcgaatctgg tggcaccttc gcgcctgtct cgctgctttc      3240
gataagtctc tagccattta aaattttga tgacctgctg cgacgctttt tttctggcaa      3300
gatagtcttg taaatgcggg ccaagatctg cacactggta tttcggtttt tggggccgcg      3360
ggcggcgacg gggcccgtgc gtcccagcgc acatgttcgg cgaggcgggg cctgcgagcg      3420
cggccaccga gaatcggacg ggggtagtct caagctggcc ggcctgctct ggtgcctggc      3480
ctcgcgccgc cgtgtatcgc cccgccctgg gcggcaaggc tggcccggtc ggcaccagtt      3540
gcgtgagcgg aaagatggcc gcttcccggc cctgctgcag ggagctcaaa atggaggacg      3600
cggcgctcgg gagagcgggc gggtgagtca cccacacaaa ggaaaagggc ctttccgtcc      3660
tcagccgtcg cttcatgtga ctccacggag taccgggcgc cgtccaggca cctcgattag      3720
ttctcgagct tttggagtac gtcgtcttta ggttgggggg aggggtttta tgcgatggag      3780
tttccccaca ctgagtgggt ggagactgaa gttaggccag cttggcactt gatgtaattc      3840
tccttggaat ttgccctttt tgagtttgga tcttggttca ttctcaagcc tcagacagtg      3900
gttcaaagtt ttttcttcc atttcaggtg tcgtgacgta cggccaccat ggtgagcaag      3960
ggcgaggagc tgttcaccgg ggtggtgccc atcctggtcg agctggacgg cgacgtaaac      4020
ggccacaagt tcagcgtgag gggcgagggc gagggcgatg ccaccaacgg caagctgacc      4080
ctgaagttca tctgcaccac cggcaagctg cccgtgccct ggcccaccct cgtgaccacc      4140
ctgagccacg gcgtgcagtg cttcgcccgc taccccgacc acatgaagca gcacgacttc      4200
ttcaagtccg ccatgcccga aggctacgtc caggagcgca ccatcttctt caaggacgac      4260
ggcacctaca agacccgcgc cgaggtgaag ttcgagggcg acaccctggt gaaccgcatc      4320
```

```
gagctgaagg gcgtcgactt caaggaggac ggcaacatcc tggggcacaa gctggagtac    4380
aacttcaaca gccacaacat ctatatcatg gccgtcaagc agaagaacgg catcaaggtg    4440
aacttcaaga tccgccacaa cgtggaggac ggcagcgtgc agctcgccga ccactaccag    4500
cagaacaccc ccatcggcga cggccccgtg ctgctgcccg acagccacta cctgagcacc    4560
cagtccgtgc tgagcaaaga ccccaacgag aagcgcgatc acatggtcct gctggagttc    4620
cgcaccgccg ccgggatcac tctcggcatg gacgagctgt acaagtaaac gcgttaagtc    4680
gagtcgacaa tcaacctctg gattacaaaa tttgtgaaag attgactggt attcttaact    4740
atgttgctcc ttttacgcta tgtggatacg ctgctttaat gcctttgtat catgctattg    4800
cttcccgtat ggctttcatt ttctcctcct tgtataaatc ctggttgctg tctctttatg    4860
aggagttgtg gcccgttgtc aggcaacgtg gcgtggtgtg cactgtgttt gctgacgcaa    4920
cccccactgg ttggggcatt gccaccacct gtcagctcct ttccgggact ttcgctttcc    4980
ccctccctat tgccacggcg gaactcatcg ccgcctgcct tgcccgctgc tggacagggg    5040
ctcggctgtt gggcactgac aattccgtgg tgttgtcggg gaaatcatcg tcctttcctt    5100
ggctgctcgc ctgtgttgcc acctggattc tgcgcgggac gtccttctgc tacgtccctt    5160
cggccctcaa tccagcggac cttccttccc gcggcctgct gccggctctg cggcctcttc    5220
cgcgtcttcg ccttcgccct cagacgagtc ggatctccct ttgggccgcc tctccgcgtc    5280
gacggatccg gtgatgggac ttacaaggca gctgtagatc ttagccactt tttaaaagaa    5340 aagggggggac tggaagggct aattcactcc caacgaagac aagatctgct ttttgcttgt    5400
actgggtctc tctggttaga ccagatctga gcctgggagc tctctggcta actagggaac    5460
ccactgctta agcctcaata aagcttgcct tgagtgcttc aagtagtgtg tgcccgtctg    5520
ttgtgtgact ctggtaacta gagatccctc agacccttt agtcagtgtg aaaatctct    5580 agcagtacgt atagtagttc atgtcatctt attattcagt atttataact tgcaaagaaa    5640
tgaatatcag agagtgagag gaacttgttt attgcagctt ataatggtta caaataaagc    5700
aatagcatca caaatttcac aaataaagca ttttttcac tgcattctag ttgtggtttg    5760
tccaaactca tcaatgtatc ttatcatgtc tggctctagc tatcccgccc ctaactccgc    5820
ccatcccgcc cctaactccg cccagttccg cccattctcc gccccatggc tgactaattt    5880
tttttattta tgcagaggcc gaggccgcct cggcctctga gctattccag aagtagtgag    5940
gaggcttttt tggaggccta gggacgtacc caattcgccc tatagtgagt cgtattacgc    6000
gcgctcactg gccgtcgttt tacaacgtcg tgactgggaa aaccctggcg ttacccaact    6060
taatcgcctt gcagcacatc cccctttcgc cagctggcgt aatagcgaag aggcccgcac    6120
cgatcgccct tcccaacagt tgcgcagcct gaatggcgaa tgggacgcgc cctgtagcgg    6180
cgcattaagc gcggcgggtg tggtggttac gcgcagcgtg accgctacac ttgccagcgc    6240
cctagcgccc gctcctttcg ctttcttccc ttcctttctc gccacgttcg ccggctttcc    6300
ccgtcaagct ctaaatcggg gctccctt agggttccga tttagtgctt tacggcacct    6360
cgaccccaaa aaacttgatt agggtgatgg ttcacgtagt gggccatcgc cctgatagac    6420 ggttttcgc cctttgacgt tggagtccac gttctttaat agtggactct tgttccaaac    6480
tggaacaaca ctcaacccta tctcggtcta ttcttttgat ttataaggga ttttgccgat    6540
ttcggcctat tggttaaaaa atgagctgat ttaacaaaaa tttaacgcga attttaacaa    6600
aatattaacg cttacaattt aggtggcact tttcggggaa atgtgcgcgg aaccctatt    6660 tgtttatttt tctaaataca ttcaaatatg tatccgctca tgagacaata accctgataa    6720
```

-continued

```
atgcttcaat aatattgaaa aaggaagagt atgagtattc aacatttccg tgtcgccctt    6780
attccctttt ttgcggcatt ttgccttcct gttttttgctc acccagaaac gctggtgaaa   6840
gtaaaagatg ctgaagatca gttgggtgca cgagtgggtt acatcgaact ggatctcaac    6900
agcggtaaga tccttgagag ttttcgcccc gaagaacgtt ttccaatgat gagcactttt    6960
aaagttctgc tatgtggcgc ggtattatcc cgtattgacg ccgggcaaga gcaactcggt    7020
cgccgcatac actattctca gaatgacttg gttgagtact caccagtcac agaaaagcat    7080
cttacggatg gcatgacagt aagagaatta tgcagtgctg ccataaccat gagtgataac    7140
actgcggcca acttacttct gacaacgatc ggaggaccga aggagctaac cgcttttttg    7200
cacaacatgg gggatcatgt aactcgcctt gatcgttggg aaccggagct gaatgaagcc    7260
ataccaaacg acgagcgtga caccacgatg cctgtagcaa tggcaacaac gttgcgcaaa    7320
ctattaactg gcgaactact tactctagct tcccggcaac aattaataga ctggatggag    7380
gcggataaag ttgcaggacc acttctgcgc tcggcccttc cggctggctg gtttattgct    7440
gataaatctg gagccggtga gcgtgggtct cgcggtatca ttgcagcact ggggccagat    7500
ggtaagccct cccgtatcgt agttatctac acgacgggga gtcaggcaac tatggatgaa    7560
cgaaatagac agatcgctga gataggtgcc tcactgatta gcattggta actgtcagac     7620
caagtttact catatatact ttagattgat ttaaaacttc attttttaatt taaaaggatc   7680
taggtgaaga tcctttttga taatctcatg accaaaatcc cttaacgtga gttttcgttc    7740
cactgagcgt cagaccccgt agaaaagatc aaaggatctt cttgagatcc ttttttttctg   7800
cgcgtaatct gctgcttgca acaaaaaaa ccaccgctac cagcggtggt ttgtttgccg     7860
gatcaagagc taccaactct ttttccgaag gtaactggct tcagcagagc gcagatacca    7920
aatactgttc ttctagtgta gccgtagtta ggccaccact tcaagaactc tgtagcaccg    7980
cctacatacc tcgctctgct aatcctgtta ccagtggctg ctgccagtgg cgataagtcg    8040
tgtcttaccg ggttggactc aagacgatag ttaccggata aggcgcagcg gtcgggctga    8100
acggggggtt cgtgcacaca gcccagcttg gagcgaacga cctacaccga actgagatac    8160
ctacagcgtg agctatgaga aagcgccacg cttcccgaag ggagaaaggc ggacaggtat    8220
ccggtaagcg gcagggtcgg aacaggagag cgcacgaggg agcttccagg gggaaacgcc    8280
tggtatcttt atagtcctgt cgggtttcgc cacctctgac ttgagcgtcg attttttgtga   8340
tgctcgtcag gggggcggag cctatggaaa aacgccagca acgc                    8384
```

<210> SEQ ID NO 17
<211> LENGTH: 8435
<212> TYPE: DNA
<213> ORGANISM: Artificial sequence
<220> FEATURE:
<223> OTHER INFORMATION: Sequences of exemplary constructs with mcherry

<400> SEQUENCE: 17

```
cccgggtgca agatggata aagttttaaa cagagaggaa tctttgcagc taatggacct     60
tctaggtctt gaaaggagtg ggaattggct ccggtgcccg tcagtgggca gagcgcacat    120
cgcccacagt ccccgagaag ttgggggggag gggtcggcaa ttgatccggt gcctagagaa  180
ggtggcgcgg ggtaaactgg gaaagtgatg tcgtgtactg gctccgcctt tttcccgagg    240
gtgggggaga accgtatata agtgcagtag tcgccgtgaa cgttcttttt cgcaacgggt    300
ttgccgccag aacacaggta agtgccgtgt gtggttcccg cgggcctggc ctctttacgg    360
```

-continued

| | | | | | |
|---|---|---|---|---|---|
| gttatggccc | ttgcgtgcct | tgaattactt | ccactggctg | cagtacgtga | ttcttgatcc | 420 |
| cgagcttcgg | gttggaagtg | ggtgggagag | ttcgaggcct | tgcgcttaag | gagcccttc | 480 |
| gcctcgtgct | tgagttgagg | cctggcctgg | gcgctggggc | cgccgcgtgc | gaatctggtg | 540 |
| gcaccttcgc | gcctgtctcg | ctgctttcga | taagtctcta | gccatttaaa | atttttgatg | 600 |
| acctgctgcg | acgcttttt | tctggcaaga | tagtcttgta | aatgcgggcc | aagatctgca | 660 |
| cactggtatt | tcggttttg | gggccgcggg | cggcgacggg | gcccgtgcgt | cccagcgcac | 720 |
| atgttcggcg | aggcggggcc | tgcgagcgcg | gccaccgaga | tcggacgggg | ggtagtctca | 780 |
| agctggccgg | cctgctctgg | tgcctggcct | cgcgccgccg | tgtatcgccc | cgccctgggc | 840 |
| ggcaaggctg | gcccggtcgg | caccagttgc | gtgagcggaa | agatggccgc | ttcccggccc | 900 |
| tgctgcaggg | agctcaaaat | ggaggacgcg | gcgctcggga | gagcgggcgg | gtgagtcacc | 960 |
| cacacaaagg | aaaagggcct | ttccgtcctc | agccgtcgct | tcatgtgact | ccacggagta | 1020 |
| ccgggcgccg | tccaggcacc | tcgattagtt | ctcgagcttt | tggagtacgt | cgtctttagg | 1080 |
| ttgggggag | gggttttatg | cgatggagtt | tccccacact | gagtgggtgg | agactgaagt | 1140 |
| taggccagct | tggcacttga | tgtaattctc | cttggaattt | gcccttttg | agtttggatc | 1200 |
| ttggttcatt | ctcaagcctc | agacagtggt | tcaaagttt | tttcttccat | ttcaggtgtc | 1260 |
| gtgacgtacg | gccaccatgg | tgagcaaggg | cgaggaggat | aacatggcca | tcatcaagga | 1320 |
| gttcatgcgc | ttcaaggtgc | acatggaggg | ctccgtgaac | ggccacgagt | cgagatcga | 1380 |
| gggcgagggc | gagggccgcc | cctacgaggg | cacccagacc | gccaagctga | aggtgaccaa | 1440 |
| gggtggcccc | ctgcccttcg | cctgggacat | cctgtcccct | cagttcatgt | acggctccaa | 1500 |
| ggcctacgtg | aagcaccccg | ccgacatccc | cgactacttg | aagctgtcct | tccccgaggg | 1560 |
| cttcaagtgg | gagcgcgtga | tgaacttcga | ggacggcggc | gtggtgaccg | tgacccagga | 1620 |
| ctcctcctg | caggacggcg | agttcatcta | caaggtgaag | ctgcgcggca | ccaacttccc | 1680 |
| ctccgacggc | cccgtaatgc | agaagaagac | catgggctgg | gaggcctcct | ccgagcggat | 1740 |
| gtacccgag | gacggcgccc | tgaagggcga | gatcaagcag | aggctgaagc | tgaaggacgg | 1800 |
| cggccactac | gacgctgagg | tcaagaccac | ctacaaggcc | aagaagcccg | tgcagctgcc | 1860 |
| cggcgcctac | aacgtcaaca | tcaagttgga | catcacctcc | cacaacgagg | actacaccat | 1920 |
| cgtggaacag | tacgaacgcg | ccgagggccg | ccactccacc | ggcggcatgg | acgagctgta | 1980 |
| caagtaaacg | cgttaagtcg | agtcgacaat | caacctctgg | attacaaaat | ttgtgaaaga | 2040 |
| ttgactggta | ttcttaacta | tgttgctcct | tttacgctat | gtggatacgc | tgctttaatg | 2100 |
| cctttgtatc | atgctattgc | ttcccgtatg | gctttcattt | tctcctcctt | gtataaatcc | 2160 |
| tggttgctgt | ctctttatga | ggagttgtgg | cccgttgtca | ggcaacgtgg | cgtggtgtgc | 2220 |
| actgtgtttg | ctgacgcaac | ccccactggt | tggggcattg | ccaccacctg | tcagctcctt | 2280 |
| tccgggactt | tcgctttccc | cctccctatt | gccacggcgg | aactcatcgc | cgcctgcctt | 2340 |
| gcccgctgct | ggacagggc | tcggctgttg | gcactgacaa | attccgtggt | gttgtcgggg | 2400 |
| aaatcatcgt | cctttccttg | gctgctcgcc | tgtgttgcca | cctggattct | gcgcgggacg | 2460 |
| tccttctgct | acgtcccttc | ggccctcaat | ccagcggacc | ttccttcccg | cggcctgctg | 2520 |
| ccggctctgc | ggcctcttcc | gcgtcttcgc | cttcgccctc | agacgagtcg | gatctccctt | 2580 |
| tgggccgcct | ccccgcgtcg | acggatccgg | tgatgggact | tacaaggcag | ctgtagatct | 2640 |
| tagccacttt | ttaaaagaaa | aggggggact | ggaagggcta | attcactccc | aacgaagaca | 2700 |
| agatctgctt | tttgcttgta | ctgggtctct | ctggttagac | cagatctgag | cctgggagct | 2760 |

```
ctctggctaa ctagggaacc cactgcttaa gcctcaataa agcttgcctt gagtgcttca    2820
agtagtgtgt gcccgtctgt tgtgtgactc tggtaactag agatccctca gacccttta    2880 gtcagtgtgg aaaatctcta gcagtacgta tagtagttca tgtcatctta ttattcagta    2940
tttataactt gcaaagaaat gaatatcaga gagtgagagg aacttgttta ttgcagctta    3000
taatggttac aaataaagca atagcatcac aaatttcaca aataaagcat ttttttcact    3060
gcattctagt tgtggtttgt ccaaactcat caatgtatct tatcatgtct ggctctagct    3120
atcccgcccc taactccgcc catcccgccc ctaactccgc ccagttccgc ccattctccg    3180
ccccatggct gactaatttt ttttatttat gcagaggccg aggccgcctc ggcctctgag    3240
ctattccaga gtagtgagg aggcttttt ggaggcctag ggacgtaccc aattcgccct    3300
atagtgagtc gtattacgcg cgctcactgg ccgtcgtttt acaacgtcgt gactgggaaa    3360
accctggcgt tacccaactt aatcgccttg cagcacatcc ccctttcgcc agctggcgta    3420
atagcgaaga ggcccgcacc gatcgccctt cccaacagtt gcgcagcctg aatggcgaat    3480
gggacgcgcc ctgtagcggc gcattaagcg cggcgggtgt ggtggttacg cgcagcgtga    3540
ccgctacact tgccagcgcc ctagcgcccg ctcctttcgc tttcttccct tcctttctcg    3600
ccacgttcgc cggctttccc cgtcaagctc taaatcgggg gctcccttta gggttccgat    3660
ttagtgcttt acggcacctc gaccccaaaa aacttgatta gggtgatggt tcacgtagtg    3720
ggccatcgcc ctgatagacg ttttttcgcc ctttgacgtt ggagtccacg ttctttaata    3780
gtggactctt gttccaaact ggaacaacac tcaaccctat ctcggtctat tcttttgatt    3840
tataagggat tttgccgatt tcggcctatt ggttaaaaaa tgagctgatt taacaaaaat    3900
ttaacgcgaa ttttaacaaa atattaacgc ttacaattta ggtggcactt ttcggggaaa    3960
tgtgcgcgga acccctattt gtttattttt ctaaatacat tcaaatatgt atccgctcat    4020
gagacaataa ccctgataaa tgcttcaata atattgaaaa aggaagagta tgagtattca    4080
acatttccgt gtcgccctta ttccctttt tgcggcattt tgccttcctg ttttgctca    4140 cccagaaacg ctggtgaaag taaaagatgc tgaagatcag ttgggtgcac gagtgggtta    4200
catcgaactg gatctcaaca gcggtaagat ccttgagagt tttcgccccg aagaacgttt    4260
tccaatgatg agcacttta aagttctgct atgtggcgcg gtattatccc gtattgacgc    4320
cgggcaagag caactcggtc gccgcataca ctattctcag aatgacttgg ttgagtactc    4380
accagtcaca gaaaagcatc ttacggatgg catgacagta agagaattat gcagtgctgc    4440
cataaccatg agtgataaca ctgcggccaa cttacttctg acaacgatcg gaggaccgaa    4500
ggagctaacc gcttttttgc acaacatggg ggatcatgta actcgccttg atcgttggga    4560
accggagctg aatgaagcca taccaaacga cgagcgtgac accacgatgc ctgtagcaat    4620
ggcaacaacg ttgcgcaaac tattaactgg cgaactactt actctagctt cccggcaaca    4680
attaatagac tggatggagg cggataaagt tgcaggacca cttctgcgct cggcccttcc    4740
ggctggctgg tttattgctg ataaatctgg agccggtgag cgtgggtctc gcggtatcat    4800
tgcagcactg gggccagatg gtaagccctc ccgtatcgta gttatctaca cgacggggag    4860
tcaggcaact atggatgaac gaaatagaca gatcgctgag ataggtgcct cactgattaa    4920
gcattggtaa ctgtcagacc aagtttactc atatatactt tagattgatt taaaacttca    4980
tttttaattt aaaaggatct aggtgaagat cctttttgat aatctcatga ccaaaatccc    5040
ttaacgtgag ttttcgttcc actgagcgtc agaccccgta gaaaagatca aaggatcttc    5100
```

-continued

```
ttgagatcct ttttttctgc gcgtaatctg ctgcttgcaa acaaaaaaac caccgctacc      5160
agcggtggtt tgtttgccgg atcaagagct accaactctt tttccgaagg taactggctt      5220
cagcagagcg cagataccaa atactgttct tctagtgtag ccgtagttag gccaccactt      5280
caagaactct gtagcaccgc ctacatacct cgctctgcta atcctgttac cagtggctgc      5340
tgccagtggc gataagtcgt gtcttaccgg gttggactca agacgatagt taccggataa      5400
ggcgcagcgg tcgggctgaa cggggggttc gtgcacacag cccagcttgg agcgaacgac      5460
ctacaccgaa ctgagatacc tacagcgtga gctatgagaa agcgccacgc ttcccgaagg      5520
gagaaaggcg gacaggtatc cggtaagcgg cagggtcgga acaggagagc gcacgaggga      5580
gcttccaggg ggaaacgcct ggtatcttta tagtcctgtc gggtttcgcc acctctgact      5640
tgagcgtcga ttttttgtgat gctcgtcagg ggggcggagc ctatggaaaa acgccagcaa      5700
cgcggccttt ttacggttcc tggccttttg ctggccttt t gctcacatgt tctttcctgc      5760
gttatcccct gattctgtgg ataaccgtat taccgccttt gagtgagctg ataccgctcg      5820
ccgcagccga acgaccgagc gcagcgagtc agtgagcgag gaagcggaag agcgcccaat      5880
acgcaaaccg cctctccccg cgcgttggcc gattcattaa tgcagctggc acgacaggtt      5940
tcccgactgg aaagcgggca gtgagcgcaa cgcaattaat gtgagttagc tcactcatta      6000
ggcaccccag gctttacact ttatgcttcc ggctcgtatg ttgtgtggaa ttgtgagcgg      6060
ataacaattt cacacaggaa acagctatga ccatgattac gccaagcgcg caattaaccc      6120
tcactaaagg gaacaaaagc tggagctgca agcttaatgt agtcttatgc aatactcttg      6180
tagtcttgca acatggtaac gatgagttag caacatgcct tacaaggaga aaaaagcac       6240 cgtgcatgcc gattggtgga agtaaggtgg tacgatcgtg ccttattagg aaggcaacag      6300
acgggtctga catggattgg acgaaccact gaattgccgc attgcagaga tattgtattt      6360
aagtgcctag ctcgatacat aaacgggtct ctctggttag accagatctg agcctgggag      6420
ctctctggct aactagggaa cccactgctt aagcctcaat aaagcttgcc ttgagtgctt      6480
caagtagtgt gtgcccgtct gttgtgtgac tctggtaact agagatccct cagacccttt      6540
tagtcagtgt ggaaaatctc tagcagtggc gcccgaacag ggacttgaaa gcgaaaggga      6600
aaccagagga gctctctcga cgcaggactc ggcttgctga agcgcgcacg gcaagaggcg      6660
aggggcggcg actggtgagt acgccaaaaa ttttgactag cggaggctag aaggagagag      6720
atgggtgcga gagcgtcagt attaagcggg ggagaattag atcgcgatgg gaaaaaattc      6780
ggttaaggcc agggggaaag aaaaaatata aattaaaaca tatagtatgg gcaagcaggg      6840
agctagaacg attcgcagtt aatcctggcc tgttagaaac atcagaaggc tgtagacaaa      6900
tactgggaca gctacaacca tcccttcaga caggatcaga agaacttaga tcattatata      6960
atacagtagc aaccctctat tgtgtgcatc aaaggataga gataaaagac accaaggaag      7020
ctttagacaa gatagaggaa gagcaaaaca aaagtaagac caccgcacag caagcggccg      7080
ctgatcttca gacctggagg aggagatatg agggacaatt ggagaagtga attatataaa      7140
tataaagtag taaaaattga accattagga gtagcaccca ccaaggcaaa gagaagagtg      7200
gtgcagagag aaaaaagagc agtgggaata ggagctttgt ccttgggtt cttgggagca      7260 gcaggaagca ctatgggcgc agcgtcaatg acgctgacgg tacaggccag acaattattg      7320
tctggtatag tgcagcagca gaacaatttg ctgagggcta ttgaggcgca acagcatctg      7380
ttgcaactca cagtctgggg catcaagcag ctccaggcaa gaatcctggc tgtgaaaaga      7440
tacctaaagg atcaacagct cctggggatt tggggttgct ctggaaaact catttgcacc      7500
```

```
actgctgtgc cttggaatgc tagttggagt aataaatctc tggaacagat ttggaatcac    7560
acgacctgga tggagtggga cagagaaatt aacaattaca caagcttaat acactcctta    7620
attgaagaat cgcaaaacca gcaagaaaag aatgaacaag aattattgga attagataaa    7680
tgggcaagtt tgtggaattg gtttaacata acaaattggc tgtggtatat aaaattattc    7740
ataatgatag taggaggctt ggtaggttta agaatagttt ttgctgtact ttctatagtg    7800
aatagagtta ggcagggata ttcaccatta tcgtttcaga cccacctccc aaccccgagg    7860
ggacccagag agggcctatt tcccatgatt ccttcatatt tgcatatacg atacaaggct    7920
gttagagaga taattagaat taatttgact gtaaacacaa agatattagt acaaaatacg    7980
tgacgtagaa agtaataatt tcttgggtag tttgcagttt taaaattatg ttttaaaatg    8040
gactatcata tgcttaccgt aacttgaaag tatttcgatt tcttggcttt atatatcttg    8100
tggaaaggac gaaacaccgg agacggacgt ctctgtttta gagctagaaa tagcaagtta    8160
aaataaggct agtccgttat caacttgaaa aagtggcacc gagtcggtgc ttttttaagc    8220
ttggcgtaac tagatcttga gacaaatggc agtattcatc cacaatttta aaagaaaagg    8280
ggggattggg gggtacagtg caggggaaag aatagtagac ataatagcaa cagacataca    8340
aactaaagaa ttacaaaaac aaattacaaa aattcaaaat tttcgggttt attacaggga    8400
cagcagagat ccactttggc gccggctcga ggggg                              8435
```